United States Patent
Huang et al.

(10) Patent No.: US 9,315,579 B2
(45) Date of Patent: Apr. 19, 2016

(54) ANTIGEN BINDING PROTEINS THAT BIND CCR2

(71) Applicant: Sorrento Therapeutics Inc., San Diego, CA (US)

(72) Inventors: Dingqiu Huang, San Diego, CA (US); Barbara A. Swanson, Encinitas, CA (US); John Dixon Gray, San Diego, CA (US); Heyue Zhou, San Diego, CA (US); Guodi Lu, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 211 days.

(21) Appl. No.: 13/924,501

(22) Filed: Jun. 21, 2013

(65) Prior Publication Data

US 2013/0344070 A1    Dec. 26, 2013

Related U.S. Application Data

(60) Provisional application No. 61/663,496, filed on Jun. 22, 2012.

(51) Int. Cl.

| | |
|---|---|
| C07K 16/00 | (2006.01) |
| C12P 21/08 | (2006.01) |
| C07K 16/28 | (2006.01) |
| A61K 39/00 | (2006.01) |

(52) U.S. Cl.
CPC ....... *C07K 16/2866* (2013.01); *A61K 2039/505* (2013.01); *C07K 2317/21* (2013.01); *C07K 2317/33* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,406,694 B1 | 6/2002 | LaRosa | |
| 8,710,191 B2 * | 4/2014 | Gladue et al. | 530/388.22 |
| 2002/0012664 A1 | 1/2002 | LaRosa | |
| 2004/0047860 A1 | 3/2004 | Hiestand et al. | |
| 2005/0260139 A1 | 11/2005 | Pairnet | |
| 2007/0021466 A1 | 1/2007 | Ungashe | |
| 2011/0274696 A1 | 11/2011 | Glaude | |

FOREIGN PATENT DOCUMENTS

| | | |
|---|---|---|
| EP | 2135619 | 12/2009 |
| WO | 2005060368 | 7/2005 |

OTHER PUBLICATIONS

Paul, Fundamental Immunology, 3rd Edition, 1993, pp. 292-295, under the heading Fv Structure and Diversity in Three Dimensions.*
Rudikoff et al Proc. Natl. Acad. Sci.USA, 79(6):1979-1983, Mar. 1982.*
Colman P. M. Research in Immunology, 145:33-36, 1994).*
Barrios et al J Molecular Recognition 17: 332-338, 2004.*
Piatesi et al ChemBio Chem 5: 460-466, 2004.*
Kunik et al. 2012. PLoS Computational Biol. 8:1-12.*
Sela-Culang et al. 2013. Frontiers in Immunology. 4:1-13.*
Sohy et al., "Allosteric Transinhibition by Specific Antagonists in CCR2/CXCR4 Heterodimers" J. Biol. Chem. 282:30062-30069, 2007.
Zhao, "Dual targeting of CCR2 and CCR5: therapeutic potential for immunologic and cardiovascular diseases" J. Leukocyte Biol. 88:41-55, 2010.
Brodmerkel et al. "Discovery and Pharmacological Characterization of a Novel Rodent-Active CCR2 Antagonist, INCB3344" J. Immunology 175:5370-5378, 2005.
Haringman et al., "A Randomized Controlled Trial With an Anti-CCL2 (Anti-Monocyte Chemotactic Protein 1) Monoclonal Antibody in Patients With Rheumatoid Arthritis" Arthritis & Rheumatism, 54, No. 8, Aug. 2006, pp. 2387-2392.
Qian et al., "CCL2 recruits inflammatory monocytes to facilitate breast tumor metastasis" Nature, 475:222-225, 2012.
Rafei et al., "A MCP1 fusokine with CCR2-specific tumoricidal activity" Mol. Cancer, 10:121, 2011.
Sullivan et al. "Characterization of CCX140-B, an orally bioavailable antagonist of the CCR2 chemokine receptor, for the treatment of type 2 diabetes and associated complications" DOI:10.1124/jpet.111.190918, 2012.
Popivanova et al. "Blockade of a Chemokine, CCL2, Reduces Chronic Colitis-Associated Carcinogenesis in Mice" Cancer Res. 69:7884-7892, 2009.
Mellado et al., "Chemokine Receptor 2 Blockade Prevents Asthma in a Cynomolgus Monkey Model" J. Pharm. Exp. Ther. 324:769-775, 2008.
Moore et al. "Protection from Pulmonary Fibrosis in the Absence of CCR2 Signaling" J Immunol 167:4368-4377, 2001.
Lu et al. "Chemokine (C-C Motif) Ligand 2 Engages CCR2 Stromal Cells of Monocytic Origin to Promote Breast Cancer Metastasis to Lung and Bone" The Journal of Biological Chemistry vol. 284, No. 42, pp. 29087-29096, Oct. 16, 2009.
Vergunst et al., "Modulation of CCR2 in Rheumatoid Arthritis" Arthritis & Rheumatism vol. 58, No. 7, pp. 1931-1939, 2008.

(Continued)

*Primary Examiner* — Shulamith H Shafer
(74) *Attorney, Agent, or Firm* — McCarter & English, LLP; Danielle L. Herritt; Crisitin H. Cowles

(57) ABSTRACT

There is disclosed compositions and methods relating to or derived from anti-CCR2 antibodies. More specifically, there is disclosed fully human antibodies that bind CCR2, CCR2-binding fragments and derivatives of such antibodies, and CCR2-binding polypeptides comprising such fragments. Further still, there is disclosed nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having CCR2 related disorders or conditions.

8 Claims, 11 Drawing Sheets

(56) References Cited

OTHER PUBLICATIONS

Weisenberg et al. "CCR2 modulates inflammatory and metabolic effects of high-fat feeding" J. Clin. Investigation 116:115-124, 2006.
Lu et al. (2) "Cloning and functional characterization of the rabbit C-C chemokine receptor 2" BMC Immunology 2005, 6:15.
Yamasaki et al. "Role of CCR2 in immunobiology and neurobiology" Clin. Exp. Neuroimmunol. doi: 10.1111/ j.1759-1961.2011.
Lebre et al., "Why CCR2 and CCR5 Blockade Failed and Why CCR1 Blockade Might Still Be Effective in the Treatment of Rheumatoid Arthritis" Plos ONE 6(7):e21772, 2011.
Semple et al., "Role of chemokines in CNS health and pathology: a focus on the CCL2/CCR2 and CXCL8/CXCR2 networks" ournal of Cerebral Blood Flow & Metabolism (2010) 30, 459-473, 2010.
Wang et al. "CCR2 and CXCR4 regulate peripheral blood monocyte pharmacodynamics and link to efficacy in experimental autoimmune encephalomyelitis" Journal of Inflammation 2009, 6:32 doi:10.1186/1476-9255-6-32, 2009.
Salanga et al., "Modulation of Chemokine Receptor Activity through Dimerization and Crosstalk" Cell Mol Life Sci. Apr. 2009; 66(8): 1370-1386. doi:10.1007/s00018-008-8666-1.

\* cited by examiner

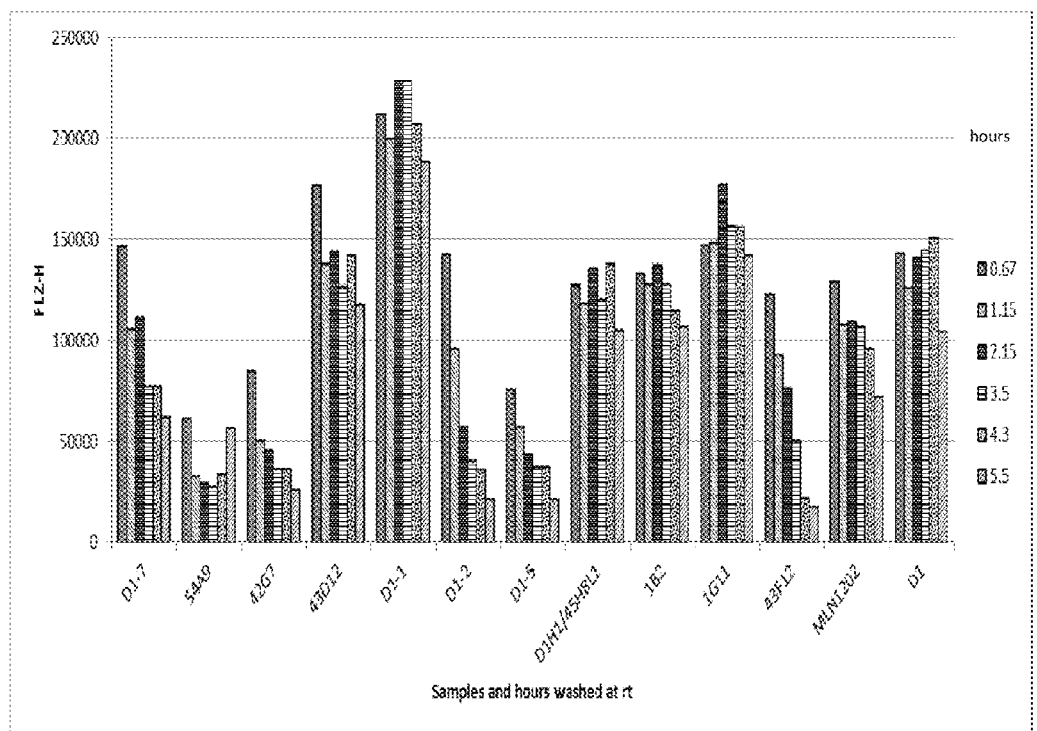
Figure 13: Off-rate of CCR2 IgG1 clones from CHO-huCCR2 cells

ANTIGEN BINDING PROTEINS THAT BIND CCR2

CROSS REFERENCE TO RELATED APPLICATION

This patent application claims priority from U.S. provisional patent application 61/663,496 filed 22 Jun. 2012.

TECHNICAL FIELD

The present disclosure provides compositions and methods relating to or derived from anti-CCR2 antibodies. More specifically, the present disclosure provides human antibodies that bind CCR2, CCR2-binding fragments and derivatives of such antibodies, and CCR2-binding polypeptides comprising such fragments. Further still, the present disclosure provides nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having CCR2 related disorders or conditions, including CCR2 mediated disorder is selected from the group consisting of autoimmune disorders, cardiovascular disorders, inflammatory disorders, immune disorders, proliferative disorders, fibrotic disorders, viral infections, neurological disorders and metabolic disorders.

BACKGROUND

CC-Chemokine Receptor 2 (CCR2) is expressed on the surface of several leukocyte subsets, such as monocytes, dendritic cells and memory T-cells, and appears to be expressed in two slightly different forms (CCR2α and CCR2β) due to alternative splicing of the mRNA encoding the carboxy-terminal region (Charo et al., *Proc. Natl. Acad. Sci. USA* 91:2752-2756 (1994)). CCR2 is the primary receptor for Chemokine Ligand CCL2 (Monocyte Chemoattractant Protein 1 (MCP-1)) and also binds CCL8 (MCP-2), CCL7 (MCP-3), CCL13 (MCP-4), CCL12 (MCP-5) and HIV. A substantial body of evidence, in both animal models and man, supports the involvement of CCR2 and CCL2 in the pathogenesis of atherosclerosis and other CCR2 mediated disorders. CCL2 is expressed in atherosclerotic lesions in human arteries and is associated with macrophage-rich regions (Nelken et al. (1991) *J. Clin. Invest.* 88(4):1121-7; Yla-Hertuala et al. (1991) *Proc. Natl. Acad. Sci. USA.* 88(12):5252-6; and Seino et al. (1995) *Cytokine* 7(6):575-9). In animals, elimination of CCR-2 expression by genetic manipulation in knockout models results in reduced atheroma generation in apolipoprotein E (ApoE) deletion mouse models of atherosclerosis (Boring et al. (1998) *Nature* 394(6696):894-7; and Dawson et al. (1999) *Atherosclerosis* 143(1):205-11). Similarly, genetic disruption of the gene encoding CCL2, truncation of CCL2, or expression of dominant negative CCL2 reduced atherosclerotic lesion formation in multiple mouse models of atherosclerosis (Ni et al. (2001) *Circulation* 103 (16):2096-2101; Gu L. et al. (1998) Mol. Cell. 2(2):275-81; Gosling et al. (1999) *J. Clin. Invest.* 103(6):773-778; and Inoue et al. (2002) *Circulation* 106(21):2700-6). Alternatively, overexpression of CCL2, either locally in the carotid artery (Namiki et al. (2002) *Arterioscler. Thromb. Vasc. Biol.* 22(1):115-20) or in blood monocytes derived from transplanted transgenic overexpressing bone marrow from syngeneic mice (Aiello et al. (1999) *Arterioscler. Thromb. Vasc. Biol.* 19(6):1518-25), drives increased atheroma formation in susceptible animal models.

Thus, CCR2 antagonists, CCL2 antagonists or agents which interfere with the binding of CCR2 to its natural ligands represent a class of important therapeutic agents.

In addition to the mammalian chemokine receptors, mammalian cytomegaloviruses, herpesviruses and pox viruses have been shown to express, in infected cells, proteins with the binding properties of chemokine receptors (Wells et al., *Curr. Opin. Biotech.* 1997, 8, 741-748). Human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases; as well as autoimmune pathologies, such as rheumatoid arthritis and multiple sclerosis; and metabolic diseases, such as atherosclerosis and diabetes (reviewed in: Charo et al., *New Eng. J. Med.* 2006, 354, 610-621; Gao et al., *Chem. Rev.* 2003, 103, 3733; Carter, *Curr. Opin. Chem. Biol.* 2002, 6, 510; Trivedi et al., *Ann. Reports Med. Chem.* 2000, 35, 191; Saunders et al., *Drug Disc. Today* 1999, 4, 80; Premack et al., *Nature Medicine* 1996, 2, 1174). For example, the chemokine monocyte chemoattractant-1 (MCP-1) and its receptor CC Chemokine Receptor 2 (CCR2) play a pivotal role in attracting leukocytes to sites of inflammation and in subsequently activating these cells. When the chemokine MCP-1 binds to CCR2, it induces a rapid increase in intracellular calcium concentration, increased expression of cellular adhesion molecules, and the promotion of leukocyte migration. Demonstration of the importance of the MCP-1/CCR-2 interaction has been provided by experiments with genetically modified mice.

MCP-1-/-mice were unable to recruit monocytes into sites of inflammation after several different types of immune challenge (Lu et al., *J. Exp. Med.* 1998, 187, 601) Likewise, CCR2-/-mice were unable to recruit monocytes or produce interferon-γ when challenged with various exogenous agents; moreover, the leukocytes of CCR2 null mice did not migrate in response to MCP-1 (Boring et al., *J. Clin. Invest.* 1997, 100, 2552), thereby demonstrating the specificity of the MCP-1/CCR-2 interaction. Two other groups have independently reported equivalent results with different strains of CCR-2-/-mice (Kuziel et al., *Proc. Natl. Acad. Sci. USA* 1997, 94, 12053, and Kurihara et al., *J. Exp. Med.* 1997, 186, 1757). The viability and generally normal health of the MCP-1-/- and CCR-2-/-animals is noteworthy, in that disruption of the MCP-1/CCR-2 interaction does not induce physiological crisis. Taken together, these data lead one to the conclusion that molecules that block the actions of MCP-1/CCR2 would be useful in treating a number of inflammatory and autoimmune disorders (Feria et al., *Exp. Opin. Ther. Patents* 2006, 16, 49; and Dawson et al., *Exp. Opin. Ther. Targets* 2003, 7, 35). This hypothesis has now been validated in a number of different animal disease models, as described below.

It is known that MIP-1α is elevated in the synovial fluid and blood of patients with rheumatoid arthritis (Koch et al., *J. Clin. Invest.* 1994, 93, 921-928). Moreover, several studies have demonstrated the potential therapeutic value of antagonism of the MIP-1α/CCR1 interaction in treating rheumatoid arthritis (Pease et al., *Expert Opin. Invest. Drugs* 2005, 14, 785-796). An antibody to MIP-1α was shown to ameliorate experimental autoimmune encepahlomytis (EAE), a model of multiple sclerosis, in mice (Karpus et al., *J. Immun.* 1995, 5003-5010). Likewise, inflammatory disease symptoms could be controlled via direct administration of antibodies for MIP-1α to mice with collagen-induced arthritis (Lukacs et al., 1995, 95, 2868-2876).

MCP-1 is upregulated in patients who develop bronchiolitis obliterans syndrome after lung transplantation (Reynaud-Gaubert et al., *J. Heart Lung Transplant.*, 2002, 21, 721-730; Belperio et al., *J. Clin. Invest.* 2001, 108, 547-556). In a murine model of bronchiolitis obliterans syndrome, administration of an antibody to MCP-1 led to attenuation of airway obliteration; likewise, CCR2−/−mice were resistant to airway obliteration in this same model (Belperio et al., *J. Clin. Invest.* 2001, 108, 547-556). These data suggest that antagonism of MCP-1/CCR2 may be beneficial in treating rejection of organs following transplantation. In addition, studies have shown that disruption of MCP-1/CCR2 axis was able to prolong the survival of islet transplant (Lee et al., *J. Immunol.* 2003, 171, 6929; Abdi et al., *J. Immunol.* 2004, 172, 767). In rat graft models, CCR2 and MCP-1 was shown to be upregulated in grafts that develop graft vasculopathy (Horiguchi et al., *J. Heart Lung Transplant.* 2002, 21, 1090). In another study, anti-MCP-1 gene therapy attenuated graft vasculopathy (Saiura et al., *Arterioscler. Thromb. Vasc. Biol.* 2004, 24, 1886). One study described inhibition of experimental vein graft neointimal formation by blockage of MCP-1 (Tatewaki et al., *J. Vasc. Surg.* 2007, 45, 1236).

Other studies have demonstrated the potential therapeutic value of antagonism of the MCP-1/CCR2 interaction in treating asthma. Sequestration of MCP-1 with a neutralizing antibody in ovalbumin-challenged mice resulted in marked decrease in bronchial hyperresponsiveness and inflammation (Gonzalo et al., *J. Exp. Med.* 1998, 188, 157). It proved possible to reduce allergic airway inflammation in *Schistosoma mansoni* egg-challenged mice through the administration of antibodies for MCP-1 (Lukacs et al., *J. Immunol.* 1997, 158, 4398). Consistent with this, MCP-1−/− mice displayed a reduced response to challenge with *Schistosoma mansoni* egg (Lu et al., *J. Exp. Med.* 1998, 187, 601).

Other studies have demonstrated the potential therapeutic value of antagonism of the MCP-1/CCR2 interaction in treating kidney disease. Administration of antibodies for MCP-1 in a murine model of glomerulamephritis resulted in a marked decrease in glomerular crescent formation and deposition of type I collagen (Lloyd et al., *J. Exp. Med.* 1997, 185, 1371). In addition, MCP-1−/−mice with induced nephrotoxic serum nephritis showed significantly less tubular damage than their MCP-1+/+counterparts (Tesch, G. H. et al., *J. Clin. Invest.* 1999, 103, 73).

Several studies have demonstrated the potential therapeutic value of antagonism of the MCP-1/CCR2 interaction in treating systemic lupus erythematosus. CCR2−/−mice exhibited prolonged survival and reduced renal disease relative to their WT counterparts in a murine model of systemic lupus erythematosus (Perez de Lema et al. *J. Am. Soc. Neph.* 2005, 16, 3592). These data are consistent with the disease-modifying activity found in recent studies on genetic deletion of MCP-1 (Shimizu, S. et al. *Rheumatology* (Oxford) 2004, 43, 1121; Tesch et al., *J. Exp. Med.* 1999, 190, 1813) or administration of a peptide antagonist of CCR2 (Hasegawa et al. *Arthritis & Rheumatism* 2003, 48, 2555) in rodent models of lupus.

A remarkable 30-fold increase in CCR2$^+$ lamina propria lymphocytes was observed in the small bowels from Crohn's patients relative to non-diseased ileum (Connor et al., *Gut* 2004, 53, 1287). Also of note, there was an expansion in the subset of circulating CCR2$^+$/CD14$^+$/CD56$^+$ monocytes in patients with active Crohn's disease relative to controls. Several rodent studies have demonstrated the potential therapeutic value of antagonism of the MCP-1/CCR2 interaction in treating Crohn's disease/colitis. CCR-2−/−mice were protected from the effects of dextran sodium sulfate-induced colitis (Andres et al., *J. Immunol.* 2000, 164, 6303). Administration of a small molecule antagonist of CCR2, CCR5, and CXCR3 (murine binding affinities=24, 236, and 369 nM, respectively) also protected against dextran sodium sulfate-induced colitis (Tokuyama et al., *Int. Immunol.* 2005, 17, 1023). Finally, MCP-1−/−mice showed substantially reduced colonic damage (both macroscopic and histological) in a hapten-induced model of colitis (Khan et al., *Am. J. Physiol. Gastrointest. Liver Physiol.* 2006, 291, G803).

Two reports described the overexpression of MCP-1 in the intestinal epithelial cells and bowel mucosa of patients with inflammatory bowel disease (Reinecker et al., *Gastroenterology* 1995, 108, 40, and Grimm et al., *J. Leukoc. Biol.* 1996, 59, 804). One study described the association of promoter polymorphism in the MCP-1 gene with scleroderma (systemic sclerosis) (Karrer et al., *J. Invest. Dermatol.* 2005, 124, 92). In related models of tissue fibrosis, inhibition of CCR2/MCP-1 axis reduced fibrosis in skin (Yamamoto et al., *J. Invest. Dermatol.* 2003, 121, 510; Ferreira et al., *J. Invest. Dermatol.* 2006, 126, 1900), lung (Okuma et al., *J. Pathol.* 2004, 204, 594; Gharaee-Kermani et al., *Cytokine* 2003, 24, 266), kidney (Kitagawa et al., *Am. J. Pathol.* 2004, 165, 237; Wada et al., *J. Am. Soc. Nephrol.* 2004, 15, 940), heart (Hayashidani et al., *Circulation* 2003, 108, 2134), and liver (Tsuruta et al., *Int. J. Mol. Med.* 2004, 14, 837).

One study has demonstrated the potential therapeutic value of antagonism of the MCP-1/CCR2 interaction in treating alveolitis. When rats with IgA immune complex lung injury were treated intravenously with antibodies raised against rat MCP-1 (JE), the symptoms of alveolitis were partially alleviated (Jones et al., *J. Immunol.* 1992, 149, 2147). Several studies have shown the potential therapeutic value of antagonism of the MCP-1/CCR2 interaction in treating cancer (reviewed in: Craig et al., *Cancer Metastasis Rev.* 2006, 25, 611; Conti, *Seminars in Cancer Biology* 2004, 14, 149; Giles, *Curr. Cancer Drug Targets* 2006, 6, 659). When immunodeficient mice bearing human breast carcinoma cells were treated with an anti-MCP-1 antibody, inhibition of lung micrometastases and increases in survival were observed (Salcedo et al., *Blood* 2000, 96, 34-40). Using human clinical tumor specimens, CCR2 expression was associated with prostrate cancer progression (Lu et al., *J. Cell. Biochem.* 2007, 101, 676). In vitro, MCP-1 expression has been shown to mediate prostrate cancer cell growth and invasion (Lu et al., *Prostate* 2006, 66, 1311); furthermore, MCP-1 expressed by prostrate cancer cells induced human bone marrow progenitors for bone resorption (Lu et al., *Cancer Res.* 2007, 67, 3646).

Multiple studies have described the potential therapeutic value of antagonism of the MCP-1/CCR2 interaction in treating restenosis. In humans, MCP-1 levels correlate directly with risk for restenosis (Cipollone et al., *Arterioscler. Thromb. Vasc. Biol.* 2001, 21, 327). Mice deficient in CCR2 or in MCP-1 showed reductions in the intimal area and in the intima/media ratio (relative to wildtype littermates) after arterial injury (Roque et al., *Arterioscler. Thromb. Vasc. Biol.* 2002, 22, 554; Schober et al., *Circ. Res.* 2004, 95, 1125; Kim et al., *Biochem Biophys. Res. Commun.* 2003, 310, 936). In mice, transfection of a dominant negative inhibitor of MCP-1 in the skeletal muscle (Egashira et al., *Circ. Res.* 2002, 90, 1167) also reduced intimal hyperplasia after arterial injury.

Blockade of CCR2 using a neutralizing antibody reduced neointimal hyperplasia after stenting in primates (Horvath et al., *Circ. Res.* 2002, 90, 488).

Two reports describe the overexpression of MCP-1 rats with induced brain trauma (King et al., *J. Neuroimmunol.* 1994, 56, 127, and Berman et al., *J. Immunol.* 1996, 156, 3017). In addition, studies have shown that both CCR2−/− (Dimitrijevic et al., *Stroke* 2007, 38, 1345) and MCP-1−/− mice (Hughes et al., *J. Cereb. Blood Flow Metab.* 2002, 22, 308) are partially protected from ischemia/reperfusion injury.

Monocytes/macrophages play an important role in the development of neuropathic pain (Liu et al., *Pain* 2000, 86, 25). Consistent with this notion, a potential role for CCR2 in the treatment of both inflammatory and neuropathic pain has been described recently. CCR2−/−mice showed altered responses to inflammatory pain relative to their WT counterparts, including reduced pain behavior after intraplantar formalin injection and slightly reduced mechanical allodynia after intraplantar CFA injection (Abbadie et al., *Proc. Natl. Acad. Sci., USA* 2003, 100, 7947). In addition, CCR2−/−mice did not display significant mechanical allodynia after sciatic nerve injury. Likewise, a small molecule CCR2 antagonist reduced mechanical allodynia to 80% of pre-injury levels after oral administration (WO 2004/110376).

One study described the critical role of MCP-1 in ischemic cardiomyopathy (Frangogiannis et al., *Circulation* 2007, 115, 584). Another study described the attenuation of experimental heart failure following inhibition of MCP-1 (Hayashidani et al., *Circulation* 2003, 108, 2134). Other studies have provided evidence that MCP-1 is overexpressed in various disease states not mentioned above. These reports provide correlative evidence that MCP-1 antagonists could be useful therapeutics for such diseases. Another study has demonstrated the overexpression of MCP-1 in rodent cardiac allografts, suggesting a role for MCP-1 in the pathogenesis of transplant arteriosclerosis (Russell et al., *Proc. Natl. Acad. Sci. USA* 1993, 90, 6086). The overexpression of MCP-1 has been noted in the lung endothelial cells of patients with idiopathic pulmonary fibrosis (Antoniades et al., *Proc. Natl. Acad. Sci. USA* 1992, 89, 5371). Similarly, the overexpression of MCP-1 has been noted in the skin from patients with psoriasis (Deleuran et al., *J. Dermatol. Sci.* 1996, 13, 228, and Gillitzer et al., *J. Invest. Dermatol.* 1993, 101, 127); correlative findings with predominance of CCR2+ cells have also been reported (Vestergaard et al., *Acta Derm. Venerol.* 2004, 84, 353). Finally, a recent report has shown that MCP-1 is overexpressed in the brains and cerebrospinal fluid of patients with HIV-1-associated dementia (WO 99/46991).

In addition, CCR2 polymorphism has been shown to be associated with sarcoidosis at least in one subset of patients (Spagnolo et al., *Am. J. Respir. Crit. Care Med.* 2003, 168, 1162).

It should also be noted that CCR2 has been implicated as a co-receptor for some strains of HIV (Doranz et al., *Cell* 1996, 85, 1149). It has also been determined that the use of CCR2 as an HIV co-receptor can be correlated with disease progression (Connor et al., *J. Exp. Med.* 1997, 185, 621). This finding is consistent with the recent finding that the presence of a CCR2 mutant, CCR2-64I, is positively correlated with delayed onset of HIV in the human population (Smith et al., *Science* 1997, 277, 959). Although MCP-1 has not been implicated in these processes, it may be that MCP-1 antagonists that act via binding to CCR2 may have beneficial therapeutic effects in delaying the disease progression to AIDS in HIV-infected patients.

SUMMARY

The present disclosure provides a fully human antibody of an IgG class that binds to a CCR2 epitope with a binding affinity of at least $10^{-6}$M, which has a heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, and combinations thereof, that has a light chain variable domain sequence that is at least 95% identical to the amino acid sequence consisting of SEQ ID NO. 2, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called D1 herein), SEQ ID NO. 3/SEQ ID NO. 2 (called 1A2 herein), SEQ ID NO. 4/SEQ ID NO. 2 (called 1B11 herein), SEQ ID NO. 5/SEQ ID NO. 2 (called 1G11 herein), SEQ ID NO. 6/SEQ ID NO. 2 (called 1H5 herein), SEQ ID NO. 7/SEQ ID NO. 2 (called 1B2 herein), SEQ ID NO. 8/SEQ ID NO. 2 (called D1-1 herein), SEQ ID NO. 9/SEQ ID NO. 2 (called D1-2 herein), SEQ ID NO. 10/SEQ ID NO. 2 (called D1-3 herein), SEQ ID NO. 11/SEQ ID NO. 2 (called D1-4 herein), SEQ ID NO. 12/SEQ ID NO. 2 (called D1-5 herein), SEQ ID NO. 13/SEQ ID NO. 2 (called D1-6 herein), SEQ ID NO. 14/SEQ ID NO. 2 (called D1-7 herein), SEQ ID NO. 15/SEQ ID NO. 2 (called D1-8 herein), SEQ ID NO. 8/SEQ ID NO. 16 (called D1-1A herein), SEQ ID NO. 9/SEQ ID NO. 16 (called D1-2A herein), SEQ ID NO. 10/SEQ ID NO. 16 (called D1-3A herein), SEQ ID NO. 11/SEQ ID NO. 16 (called D1-4A herein), SEQ ID NO. 12/SEQ ID NO. 16 (called D1-5A herein), SEQ ID NO. 13/SEQ ID NO. 16 (called D1-6A herein), SEQ ID NO. 14/SEQ ID NO. 16 (called D1-7A herein), SEQ ID NO. 15/SEQ ID NO. 16 (called D1-8A herein), SEQ ID NO. 8/SEQ ID NO. 32 (called D1-1B herein), SEQ ID NO. 9/SEQ ID NO. 32 (called D1-2B herein), SEQ ID NO. 10/SEQ ID NO. 32 (called D1-3B herein), SEQ ID NO. 11/SEQ ID NO. 32 (called D1-4B herein), SEQ ID NO. 12/SEQ ID NO. 32 (called D1-5B herein), SEQ ID NO. 13/SEQ ID NO. 32 (called D1-6B herein), SEQ ID NO. 14/SEQ ID NO. 32 (called D1-7A herein), SEQ ID NO. 15/SEQ ID NO. 32 (called D1-8B herein), SEQ ID NO. 17/SEQ ID NO. 18 (called 42A0 herein), SEQ ID NO. 19/SEQ ID NO. 20 (called 42D4 herein), SEQ ID NO. 21/SEQ ID NO. 22 (called 42E8 herein), SEQ ID NO. 23/SEQ ID NO. 24 (called 42F1 herein), SEQ ID NO. 25/SEQ ID NO. 26 (called 42G7 herein), SEQ ID NO. 27/SEQ ID NO. 28 (called 43G12 herein), SEQ ID NO. 29/SEQ ID NO. 30 (called 43F12 herein), SEQ ID NO. 31/SEQ ID NO. 32 (called 45H8 herein), SEQ ID NO. 33/SEQ ID NO. 34 (called 44A4 herein), SEQ ID NO. 35/SEQ ID NO. 36 (called 45D7 herein), SEQ ID NO. 37/SEQ ID NO. 38 (called 54A9 herein), SEQ ID NO. 39/SEQ ID NO. 40 (called 54C1 herein), SEQ ID NO. 41/SEQ ID NO. 42 (called 4255E40 herein), SEQ ID NO. 43/SEQ ID NO. 44 (called 55F5 herein), and combinations thereof.

The present disclosure provides a Fab fully human antibody fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, and combinations thereof, and that has a light chain variable domain sequence that is at least 95% identical to the amino acid sequence consisting of SEQ ID NO. 2, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, and combinations thereof. Preferably, the fully human antibody Fab fragment has both a heavy chain variable domain region and a light chain variable domain region wherein the antibody has a heavy chain/light chain variable domain sequence selected from the group consisting SEQ ID NO. 1/SEQ ID NO. 2, SEQ ID NO. 3/SEQ ID NO. 2, SEQ ID NO. 4/SEQ ID NO. 2, SEQ ID NO. 5/SEQ ID NO. 2, SEQ ID NO. 6/SEQ ID NO. 2, SEQ ID NO. 7/SEQ ID NO. 2, SEQ ID NO. 8/SEQ ID NO. 2, SEQ ID NO. 9/SEQ ID NO. 2, SEQ ID NO. 10/SEQ ID NO. 2, SEQ ID NO. 11/SEQ ID NO. 2, SEQ ID NO. 12/SEQ ID NO. 2, SEQ ID NO. 13/SEQ ID NO. 2, SEQ ID NO. 14/SEQ ID NO. 2, SEQ ID NO. 15/SEQ ID NO. 2, SEQ ID NO. 8/SEQ ID NO. 16, SEQ ID NO. 9/SEQ ID NO. 16, SEQ ID NO. 10/SEQ ID NO. 16, SEQ ID NO. 11/SEQ ID NO. 16, SEQ ID NO. 12/SEQ ID NO. 16, SEQ ID NO. 13/SEQ ID NO. 16, SEQ ID NO. 14/SEQ ID NO. 16, SEQ ID NO. 15/SEQ ID NO. 16, SEQ ID NO. 8/SEQ ID NO. 32, SEQ ID NO. 9/SEQ ID NO. 32, SEQ ID NO. 10/SEQ ID NO. 32, SEQ ID NO. 11/SEQ ID NO. 32, SEQ ID NO. 12/SEQ ID NO. 32, SEQ ID NO. 13/SEQ ID NO. 32, SEQ ID NO. 14/SEQ ID NO. 32, SEQ ID NO. 15/SEQ ID NO. 32, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, and that has a light chain variable domain sequence that is at least 95% identical to the amino acid sequence consisting of SEQ ID NO. 2, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 2, SEQ ID NO. 4/SEQ ID NO. 2, SEQ ID NO. 5/SEQ ID NO. 2, SEQ ID NO. 6/SEQ ID NO. 2, SEQ ID NO. 7/SEQ ID NO. 2, SEQ ID NO. 8/SEQ ID NO. 2, SEQ ID NO. 9/SEQ ID NO. 2, SEQ ID NO. 10/SEQ ID NO. 2, SEQ ID NO. 11/SEQ ID NO. 2, SEQ ID NO. 12/SEQ ID NO. 2, SEQ ID NO. 13/SEQ ID NO. 2, SEQ ID NO. 14/SEQ ID NO. 2, SEQ ID NO. 15/SEQ ID NO. 2, SEQ ID NO. 8/SEQ ID NO. 16, SEQ ID NO. 9/SEQ ID NO. 16, SEQ ID NO. 10/SEQ ID NO. 16, SEQ ID NO. 11/SEQ ID NO. 16, SEQ ID NO. 12/SEQ ID NO. 16, SEQ ID NO. 13/SEQ ID NO. 16, SEQ ID NO. 14/SEQ ID NO. 16, SEQ ID NO. 15/SEQ ID NO. 16, SEQ ID NO. 8/SEQ ID NO. 32, SEQ ID NO. 9/SEQ ID NO. 32, SEQ ID NO. 10/SEQ ID NO. 32, SEQ ID NO. 11/SEQ ID NO. 32, SEQ ID NO. 12/SEQ ID NO. 32, SEQ ID NO. 13/SEQ ID NO. 32, SEQ ID NO. 14/SEQ ID NO. 32, SEQ ID NO. 15/SEQ ID NO. 32, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, and combinations thereof.

The present disclosure further provides a method for treating a broad spectrum of mammalian cancers or a broad-spectrum of inflammatory diseases and autoimmune diseases, comprising administering an effective amount of an anti-CCR2 polypeptide, wherein the anti-CCR2 polypeptide is selected from the group consisting of a fully human antibody of an IgG class that binds to a CCR2 epitope with a binding affinity of at least $10^{-6}$M, a Fab fully human antibody fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, and combinations thereof, and that has a light chain variable domain sequence that is at least 95% identical to the amino acid consisting of SEQ ID NO. 2, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, and combinations thereof;

wherein the Fab fully human antibody fragment has the heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, and combinations thereof, and that has the light chain variable domain sequence that is at least 95% identical to the amino acid sequence consisting of SEQ ID NO. 2, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, and combinations thereof, and that has the light chain variable domain sequence that is at least 95% identical to the amino acid sequence consisting of SEQ ID NO. 2, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2, SEQ ID NO. 3/SEQ ID NO. 2, SEQ ID NO. 4/SEQ ID NO. 2, SEQ ID NO. 5/SEQ ID NO. 2, SEQ ID NO. 6/SEQ ID NO. 2, SEQ ID NO. 7/SEQ ID NO. 2, SEQ ID NO. 8/SEQ ID NO. 2, SEQ ID NO. 9/SEQ ID NO. 2, SEQ ID NO. 10/SEQ ID NO. 2, SEQ ID NO. 11/SEQ ID NO. 2, SEQ ID NO. 12/SEQ ID NO. 2, SEQ ID NO. 13/SEQ ID NO. 2, SEQ ID NO. 14/SEQ ID NO. 2, SEQ ID NO. 15/SEQ ID NO. 2, SEQ ID NO. 8/SEQ ID NO. 16, SEQ ID NO. 9/SEQ ID NO. 16, SEQ ID NO. 10/SEQ ID NO. 16, SEQ ID NO. 11/SEQ ID NO. 16, SEQ ID NO. 12/SEQ ID NO. 16, SEQ ID NO. 13/SEQ ID NO. 16, SEQ ID NO. 14/SEQ ID NO. 16, SEQ ID NO. 15/SEQ ID NO. 16, SEQ ID NO. 8/SEQ ID NO. 32, SEQ ID NO. 9/SEQ ID NO. 32, SEQ ID NO. 10/SEQ ID NO. 32, SEQ ID NO. 11/SEQ ID NO. 32, SEQ ID NO. 12/SEQ ID NO. 32, SEQ ID NO. 13/SEQ ID NO. 32, SEQ ID NO. 14/SEQ ID NO. 32, SEQ ID NO. 15/SEQ ID NO. 32, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 2, SEQ ID NO. 4/SEQ ID NO. 2, SEQ ID NO. 5/SEQ ID NO. 2, SEQ ID NO. 6/SEQ ID NO. 2, SEQ ID NO. 7/SEQ ID NO. 2, SEQ ID NO. 8/SEQ ID NO. 2, SEQ ID NO. 9/SEQ ID NO. 2, SEQ ID NO. 10/SEQ ID NO. 2, SEQ ID NO. 11/SEQ ID NO. 2, SEQ ID NO. 12/SEQ ID NO. 2, SEQ ID NO. 13/SEQ ID NO. 2, SEQ ID NO. 14/SEQ ID NO. 2, SEQ ID NO. 15/SEQ ID NO. 2, SEQ ID NO. 8/SEQ ID NO. 16, SEQ ID NO. 9/SEQ ID NO. 16, SEQ ID NO. 10/SEQ ID NO. 16, SEQ ID NO. 11/SEQ ID NO. 16, SEQ ID NO. 12/SEQ ID NO. 16, SEQ ID NO. 13/SEQ ID NO. 16, SEQ ID NO. 14/SEQ ID NO. 16, SEQ ID NO. 15/SEQ ID NO. 16, SEQ ID NO. 8/SEQ ID NO. 32, SEQ ID NO. 9/SEQ ID NO. 32, SEQ ID NO. 10/SEQ ID NO. 32, SEQ ID NO. 11/SEQ ID NO. 32, SEQ ID NO. 12/SEQ ID NO. 32, SEQ ID NO. 13/SEQ ID NO. 32, SEQ ID NO. 14/SEQ ID NO. 32, SEQ ID NO. 15/SEQ ID NO. 32, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 2, SEQ ID NO. 4/SEQ ID NO. 2, SEQ ID NO. 5/SEQ ID NO. 2, SEQ ID NO. 6/SEQ ID NO. 2, SEQ ID NO. 7/SEQ ID NO. 2, SEQ ID NO. 8/SEQ ID NO. 2, SEQ ID NO. 9/SEQ ID NO. 2, SEQ ID NO. 10/SEQ ID NO. 2, SEQ ID NO. 11/SEQ ID NO. 2, SEQ ID NO. 12/SEQ ID NO. 2, SEQ ID NO. 13/SEQ ID NO. 2, SEQ ID NO. 14/SEQ ID NO. 2, SEQ ID NO. 15/SEQ ID NO. 2, SEQ ID NO. 8/SEQ ID NO. 16, SEQ ID NO. 9/SEQ ID NO. 16, SEQ ID NO. 10/SEQ ID NO. 16, SEQ ID NO. 11/SEQ ID NO. 16, SEQ ID NO. 12/SEQ ID NO. 16, SEQ ID NO. 13/SEQ ID NO. 16, SEQ ID NO. 14/SEQ ID NO. 16, SEQ ID NO. 15/SEQ ID NO. 16, SEQ ID NO. 8/SEQ ID NO. 32, SEQ ID NO. 9/SEQ ID NO. 32, SEQ ID NO. 10/SEQ ID NO. 32, SEQ ID NO. 11/SEQ ID NO. 32, SEQ ID NO. 12/SEQ ID NO. 32, SEQ ID NO. 13/SEQ ID NO. 32, SEQ ID NO. 14/SEQ ID NO. 32, SEQ ID NO. 15/SEQ ID NO. 32, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, and combinations thereof.

Preferably, the broad spectrum of mammalian cancers to be treated is selected from the group consisting of the osteosarcoma, rhabdomyosarcoma, neuroblastoma, any pediatric cancer, kidney cancer, leukemia, renal transitional cell cancer, Werner-Morrison syndrome, acromegaly, bladder cancer, Wilm's cancer, ovarian cancer, pancreatic cancer, benign prostatic hyperplasia, breast cancer, prostate cancer, bone cancer, lung cancer, gastric cancer, colorectal cancer, cervical cancer, synovial sarcoma, diarrhea associated with metastatic carcinoid, vasoactive intestinal peptide secreting tumors, gigantism, psoriasis, atherosclerosis, smooth muscle restenosis of blood vessels and inappropriate microvascular proliferation, head and neck cancer, squamous cell carcinoma, multiple myeloma, solitary plasmacytoma, renal cell cancer, retinoblastoma, germ cell tumors, hepatoblastoma, hepatocellular carcinoma, melanoma, rhabdoid tumor of the kidney, Ewing Sarcoma, chondrosarcoma, haemotological malignancy, chronic lymphoblastic leukemia, chronic myelomonocytic leukemia, acute lymphoblastic leukemia, acute lymphocytic leukemia, acute myelogenous leukemia, acute myeloblastic leukemia, chronic myeloblastic leukemia, Hodgekin's disease, non-Hodgekin's lymphoma, chronic lymphocytic leukemia, chronic myelogenous leukemia, myelodysplastic syndrome, hairy cell leukemia, mast cell leukemia, mast cell neoplasm, follicular lymphoma, diffuse large cell lymphoma, mantle cell lymphoma, Burkitt Lymphoma, mycosis fungoides, seary syndrome, cutaneous T-cell lymphoma, chronic myeloproliferative disorders, a central nervous system tumor, brain cancer, glioblastoma, non-glioblastoma brain cancer, meningioma, pituitary adenoma, vestibular schwannoma, a primitive neuroectodermal tumor, medulloblastoma, astrocytoma, anaplastic astrocytoma, oligodendroglioma, ependymoma and choroid plexus papilloma, a myeloproliferative disorder, polycythemia vera, thrombocythemia, idiopathic myelfibrosis, soft tissue sarcoma, thyroid cancer, endometrial cancer, carcinoid cancer, germ cell tumors, liver cancer, gigantism, psoriasis, atherosclerosis, smooth muscle restenosis of blood vessels, inappropriate microvascular proliferation, acromegaly, gigantism, psoriasis, atherosclerosis, smooth muscle restenosis of blood vessels or inappropriate microvascular proliferation, Grave's disease, multiple sclerosis, systemic lupus erythematosus, Hashimoto's Thyroiditis, Myasthenia Gravis, auto-immune thyroiditis and Bechet's disease.

Preferably, the method for treating a CCR2 mediated disorder is selected from the group consisting of inflammatory, immune disorders; cardiovascular disorders; proliferative disorders; graft rejections; fibrotic diseases; viral infections; neurological disorders; and metabolic disorders. More preferably, the method for treating a CCR2 mediated disorder is an inflammatory or immune disorders selected from the group consisting of asthma, allergic rhinitis, hypersensitivity lung diseases, and hypersensitivity pneumonitis; anaphylaxis or hypersensitivity responses; drug allergies, insect sting allergies; allergic contact dermatitis; vasculitis, histamine and IgE-mediated allergic reactionsity pneumonitis, interstitial lung diseases (ILD), idiopathic pulmonary fibrosis, ILD associated with rheumatoid arthritis, systemic lupus erythematosus, ankylosing spondylitis, systemic sclerosis, Sjogren's syndrome, polymyositis, dermatomyositis, inflammatory bowel diseases, Crohn's disease, ulcerative colitis; spondyloarthropathies; scleroderma; psoriasis and inflammatory dermatoses, dermatitis, eczema, atopic dermatitis, urticaria; vasculitis, necrotizing, cutaneous, and hypersensitivity vasculitis; inflammatory glomerulopathies, arthritis, rheumatoid arthritis, psoriatic arthritis, multiple sclerosis; systemic lupus erythematosus; myasthenia gravis; juvenile onset diabetes; nephritides, glomerulonephritis; autoimmune thyroiditis; acquired immune deficiency syndrome (AIDS) and Behcet's disease.

More preferably, the method for treating a CCR2 mediated disorder is a cardiovascular disorder selected from the group consisting of atherogenesis; atherosclerosis; coronary artery disease; myocardial infarction; stroke; acute coronary syndrome; thrombosis; peripheral vascular disease of atherosclerotic origin; hypertension; and dyslipidemia.

More preferably, the method for treating a CCR2 mediated disorder is a proliferative disorder selected from the group consisting of a liquid or solid tumor type, myelomas, leukemias, chronic lymphocytic leukemia, lymphomas, B-cell lymphomas, non-Hodgkins lymphoma, lung cancer, breast cancer, prostate cancer, ovary cancer, colon cancer, kidney cancer, liver cancer, carcinomas, squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, squamous cell carcinoma of the neck and head region; sarcomas, fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, myelomas, leukemias, acute myelogenous leukemia, chronic lymphocytic leukemia, granulocytic leukemia, monocytic leukemia, lymphocytic leukemia, lymphomas, follicular lymphoma, mantle cell lymphoma, diffuse large B-cell lymphoma, malignant lymphoma, plasmocytoma, reticulum cell sarcoma, Hodgkins disease, tumors of the nervous system, glioma, meningoma, medulloblastoma, schwannoma, and epidymoma.

Preferably, the method for treating a CCR2 mediated disorder is a graft rejection, such as an allograft rejection or graft-versus-host disease, or is a fibrotic diseases such as scleroderma. Preferably, the method for treating a CCR2 mediated disorder is a neurological disorder selected from the group consisting of AIDS related dementia and pain, and neuropathic pain. Preferably, the method for treating a CCR2 mediated disorder is a metabolic diseases such as diabetes. Preferably, the method for treating a CCR2 mediated disorder is another disease selected from the group consisting of reperfusion injury; certain hematologic malignancies; cytokine-induced toxicity, septic shock, endotoxic shock, polymyositis; dermatomyositis; and sarcoidosis.

BRIEF DESCRIPTION OF THE FIGURES

FIG. 3A represents Mean±S.D. (n=3). (B). $IC_{50}$ determination of D1: THP-1 cells ($0.3 \times 10^5$ cells in 25 µl of the assay buffer) were pre-incubated with serial diluted doses of D1 for 20 min at room temperature. 25 µl of the pre-incubated cells were added to 25 µl of Calcium 4 Assay kit including probenecid to achieve the final indicated concentrations of D1. After 1 h incubation at 37° C., 5% $CO_2$ in a Poly-D-Lysine 384-well plate followed by 15 minutes at room temperature and centrifugation, 10 nM MCP-1 (final concentration in the 384-well plate) was added as challenge agonist during detection on the FlexStation3. FIG. 3B represents Mean±S.D. (n=3) and one of two independent experiments which had similar results.

FIG. 4A represents one of two independent experiments which had similar results. (B). $IC_{50}$ determination of D1: THP-1 cells (8,000 cells in 25 µl assay buffer) were pre-incubated with serial diluted doses of D1 for 20 min at room temperature. 25 µl of the pre-incubated cells were added to 25 µl of Calcium 4 Assay including probenecid to achieve the final indicated concentrations of D1. After 1 h incubation at 37° C. 5% $CO_2$ in a Poly-D-Lysine 384-well plate followed by 15 minutes at room temperature and centrifugation, 10 nM MCP-1 (final concentration in the 384-well plate) was added as challenge agonist during detection on the FlexStation3. FIG. 4B represents one of two independent experiments which had similar results.

In FIG. 5A is an $EC_{50}$ determination of MCP-1: Serial diluted concentrations of MCP-1 (indicated in FIG. 5A) in 29 of HBSS+0.1% BSA were loaded in the wells of plate in the lower chambers, whereas THP-1 cells ($0.1 \times 10^6$ cells in 25 µl of HBSS+0.1% BSA) were loaded on each site on top of 5 µm pore membrane. After 2 hour incubation at 37° C., 5% $CO_2$, the un-migrated cells on top of membrane were blotted and the membrane was removed. The migrated cells in wells of plate were counted by Cedex and EC50 of MCP-1 was calculated by Prism 5. FIG. 5A represents one of two independent experiments (Mean±SE, n=3). In FIG. 5B is an $IC_{50}$ determination of D1: Serial diluted concentrations of D1 (indicated in FIG. 5B) were pre-incubated with THP-1 cells ($0.1 \times 10^6$ cells in 25 µl) at room temperature for 20 min. MCP-1 at 3 nM was loaded in the wells of plate in the lower chambers, whereas the pre-incubated cells with D1 were loaded on top of membrane. After 2 h incubation at 37° C., 5% $CO_2$, migrated cells were collected, counted and calculated as the procedures in A. FIG. 5B represents Mean±S.D. (n=3) and one of three independent experiments which each had similar results.

FIG. 6 represents Mean±S.D (n=2) from two independent experiments which used primary human monocytes isolated from two separate donors.

FIG. 8 shows A comparison of antibodies D1 and MLN1202 for chemotaxis.

FIG. 13 shows the off-rate of various CCR2 IgG1 clones on CHO-huCCR2 cells.

DETAILED DESCRIPTION

Figure 1:
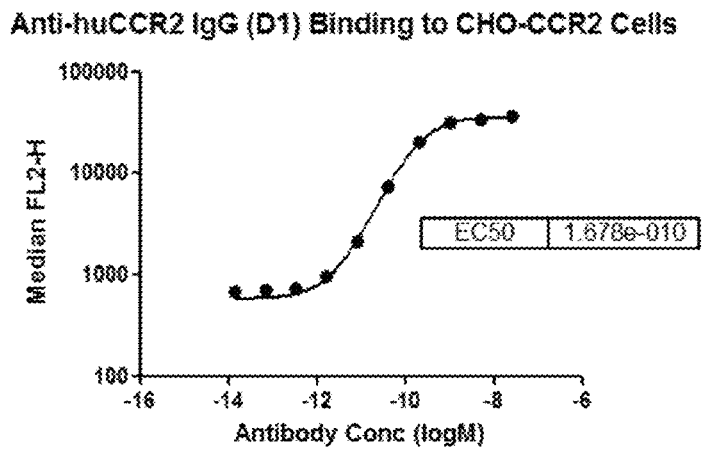
FIG. 1 shows cellular binding $EC_{50}$ for the anti-CCR2 D1 antibody. The cellular binding $EC_{50}$ for the anti-CCR2 D1 antibody was determined to be 168 pM as shown in FIG. 1.

The present disclosure provides a fully human antibody of an IgG class that binds to a CCR2 epitope with a binding affinity of $10^{-6}$M or less, that has a heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, and combinations thereof, and that has a light chain variable domain sequence that is at least 95% identical to the amino acid sequence consisting of SEQ ID NO. 2, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called D1 herein), SEQ ID NO. 3/SEQ ID NO. 2 (called 1A2 herein), SEQ ID NO. 4/SEQ ID NO. 2 (called 1B11 herein), SEQ ID NO. 5/SEQ ID NO. 2 (called 1G11 herein), SEQ ID NO. 6/SEQ ID NO. 2 (called 1H5 herein), SEQ ID NO. 7/SEQ ID NO. 2 (called 1B2 herein), SEQ ID NO. 8/SEQ ID NO. 2 (called D1-1 herein), SEQ ID NO. 9/SEQ ID NO. 2 (called D1-2 herein), SEQ ID NO. 10/SEQ ID NO. 2 (called D1-3 herein), SEQ ID NO. 11/SEQ ID NO. 2 (called D1-4 herein), SEQ ID NO. 12/SEQ ID NO. 2 (called D1-5 herein), SEQ ID NO. 13/SEQ ID NO. 2 (called D1-6 herein), SEQ ID NO. 14/SEQ ID NO. 2 (called D1-7 herein), SEQ ID NO. 15/SEQ ID NO. 2 (called D1-8 herein), SEQ ID NO. 8/SEQ ID NO. 16 (called D1-1A herein), SEQ ID NO. 9/SEQ ID NO. 16 (called D1-2A herein), SEQ ID NO. 10/SEQ ID NO. 16 (called D1-3A herein), SEQ ID NO. 11/SEQ ID NO. 16 (called D1-4A herein), SEQ ID NO. 12/SEQ ID NO. 16 (called D1-5A herein), SEQ ID NO. 13/SEQ ID NO. 16 (called D1-6A herein), SEQ ID NO. 14/SEQ ID NO. 16 (called D1-7A herein), SEQ ID NO. 15/SEQ ID NO. 16 (called D1-8A herein), SEQ ID NO. 8/SEQ ID NO. 32 (called D1-1B herein), SEQ ID NO. 9/SEQ ID NO. 32 (called D1-2B herein), SEQ ID NO. 10/SEQ ID NO. 32 (called D1-3B herein), SEQ ID NO. 11/SEQ ID NO. 32 (called D1-4B herein), SEQ ID NO. 12/SEQ ID NO. 32 (called D1-5B herein), SEQ ID NO. 13/SEQ ID NO. 32 (called D1-6B herein), SEQ ID NO. 14/SEQ ID NO. 32 (called D1-7A herein), SEQ ID NO. 15/SEQ ID NO. 32 (called D1-8B herein), SEQ ID NO. 17/SEQ ID NO. 18 (called 42A0 herein), SEQ ID NO. 19/SEQ ID NO. 20 (called 42D4 herein), SEQ ID NO. 21/SEQ ID NO. 22 (called 42E8 herein), SEQ ID NO. 23/SEQ ID NO. 24 (called 42F1 herein), SEQ ID NO. 25/SEQ ID NO. 26 (called 42G7 herein), SEQ ID NO. 27/SEQ ID NO. 28 (called 43G12 herein), SEQ ID NO. 29/SEQ ID NO. 30 (called 43F12 herein), SEQ ID NO. 31/SEQ ID NO. 32 (called 45H8 herein), SEQ ID NO. 33/SEQ ID NO. 34 (called 44A4 herein), SEQ ID NO. 35/SEQ ID NO. 36 (called 45D7 herein), SEQ ID NO. 37/SEQ ID NO. 38 (called 54A9 herein), SEQ ID NO. 39/SEQ ID NO. 40 (called 54C1 herein), SEQ ID NO. 41/SEQ ID NO. 42 (called 4255E40 herein), SEQ ID NO. 43/SEQ ID NO. 44 (called 55F5 herein), and combinations thereof.

The present disclosure provides a Fab fully human antibody fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, and combinations thereof, and that has a light chain variable domain sequence that is at least 95% identical to the amino acid sequence consisting of SEQ ID NO. 2, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 2, SEQ ID NO. 4/SEQ ID NO. 2, SEQ ID NO. 5/SEQ ID NO. 2, SEQ ID NO. 6/SEQ ID NO. 2, SEQ ID NO. 7/SEQ ID NO. 2, SEQ ID NO. 8/SEQ ID NO. 2, SEQ ID NO. 9/SEQ ID NO. 2, SEQ ID NO. 10/SEQ ID NO. 2, SEQ ID NO. 11/SEQ ID NO. 2, SEQ ID NO. 12/SEQ ID NO. 2, SEQ ID NO. 13/SEQ ID NO. 2, SEQ ID NO. 14/SEQ ID NO. 2, SEQ ID NO. 15/SEQ ID NO. 2, SEQ ID NO. 8/SEQ ID NO. 16, SEQ ID NO. 9/SEQ ID NO. 16, SEQ ID NO. 10/SEQ ID NO. 16, SEQ ID NO. 11/SEQ ID NO. 16, SEQ ID NO. 12/SEQ ID NO. 16, SEQ ID NO. 13/SEQ ID NO. 16, SEQ ID NO. 14/SEQ ID NO. 16, SEQ ID NO. 15/SEQ ID NO. 16, SEQ ID NO. 8/SEQ ID NO. 32, SEQ ID NO. 9/SEQ ID NO. 32, SEQ ID NO. 10/SEQ ID NO. 32, SEQ ID NO. 11/SEQ ID NO. 32, SEQ ID NO. 12/SEQ ID NO. 32, SEQ ID NO. 13/SEQ ID NO. 32, SEQ ID NO. 14/SEQ ID NO. 32, SEQ ID NO. 15/SEQ ID NO. 32, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, and combinations thereof, and that has a light chain variable domain sequence that is at least 95% identical to the amino acid sequence consisting of SEQ ID NO. 2, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 2, SEQ ID NO. 4/SEQ ID NO. 2, SEQ ID NO. 5/SEQ ID NO. 2, SEQ ID NO. 6/SEQ ID NO. 2, SEQ ID NO. 7/SEQ ID NO. 2, SEQ ID NO. 8/SEQ ID NO. 2, SEQ ID NO. 9/SEQ ID NO. 2, SEQ ID NO. 10/SEQ ID NO. 2, SEQ ID NO. 11/SEQ ID NO. 2, SEQ ID NO. 12/SEQ ID NO. 2, SEQ ID NO. 13/SEQ ID NO. 2, SEQ ID NO. 14/SEQ ID NO. 2, SEQ ID NO. 15/SEQ ID NO. 2, SEQ ID NO. 8/SEQ ID NO. 16, SEQ ID NO. 9/SEQ ID NO. 16, SEQ ID NO. 10/SEQ ID NO. 16, SEQ ID NO. 11/SEQ ID NO. 16, SEQ ID NO. 12/SEQ ID NO. 16, SEQ ID NO. 13/SEQ ID NO. 16, SEQ ID NO. 14/SEQ ID NO. 16, SEQ ID NO. 15/SEQ ID NO. 16, SEQ ID NO. 8/SEQ ID NO. 32, SEQ ID NO. 9/SEQ ID NO. 32, SEQ ID NO. 10/SEQ ID NO. 32, SEQ ID NO. 11/SEQ ID NO. 32, SEQ ID NO. 12/SEQ ID NO. 32, SEQ ID NO. 13/SEQ ID NO. 32, SEQ ID NO. 14/SEQ ID NO. 32, SEQ ID NO. 15/SEQ ID NO. 32, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, and combinations thereof.

The present disclosure further provides a method for treating a broad spectrum of mammalian cancers or inflammatory diseases or autoimmune diseases, comprising administering an effective amount of an anti-CCR2 polypeptide, wherein the anti-CCR2 polypeptide is selected from the group consisting of a fully human antibody of an IgG class that binds to a CCR2 epitope with a binding affinity of at least $10^{-6}$M, a Fab fully human antibody fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of and combinations thereof, and that has a light chain variable domain sequence that is at least 95% identical to the amino acid sequences selected from the group consisting of SEQ ID NO. 2, SEQ ID NO. 4, and combinations thereof;

wherein the Fab fully human antibody fragment has the heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, and combinations thereof, and that has the light chain variable domain sequence that is at least 95% identical to the amino acid sequence consisting of SEQ ID NO. 2, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, and combinations thereof, and that has the light chain variable domain sequence that is at least 95% identical to the amino acid sequence consisting of SEQ ID NO. 2, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2, SEQ ID NO. 3/SEQ ID NO. 2, SEQ ID NO. 4/SEQ ID NO. 2, SEQ ID NO. 5/SEQ ID NO. 2, SEQ ID NO. 6/SEQ ID NO. 2, SEQ ID NO. 7/SEQ ID NO. 2, SEQ ID NO. 8/SEQ ID NO. 2, SEQ ID NO. 9/SEQ ID NO. 2, SEQ ID NO. 10/SEQ ID NO. 2, SEQ ID NO. 11/SEQ ID NO. 2, SEQ ID NO. 12/SEQ ID NO. 2, SEQ ID NO. 13/SEQ ID NO. 2, SEQ ID NO. 14/SEQ ID NO. 2, SEQ ID NO. 15/SEQ ID NO. 2, SEQ ID NO. 8/SEQ ID NO. 16, SEQ ID NO. 9/SEQ ID NO. 16, SEQ ID NO. 10/SEQ ID NO. 16, SEQ ID NO. 11/SEQ ID NO. 16, SEQ ID NO. 12/SEQ ID NO. 16, SEQ ID NO. 13/SEQ ID NO. 16, SEQ ID NO. 14/SEQ ID NO. 16, SEQ ID NO. 15/SEQ ID NO. 16, SEQ ID NO. 8/SEQ ID NO. 32, SEQ ID NO. 9/SEQ ID NO. 32, SEQ ID NO. 10/SEQ ID NO. 32, SEQ ID NO. 11/SEQ ID NO. 32, SEQ ID NO. 12/SEQ ID NO. 32, SEQ ID NO. 13/SEQ ID NO. 32, SEQ ID NO. 14/SEQ ID NO. 32, SEQ ID NO. 15/SEQ ID NO. 32, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 2, SEQ ID NO. 4/SEQ ID NO. 2, SEQ ID NO. 5/SEQ ID NO. 2, SEQ ID NO. 6/SEQ ID NO. 2, SEQ ID NO. 7/SEQ ID NO. 2, SEQ ID NO. 8/SEQ ID NO. 2, SEQ ID NO. 9/SEQ ID NO. 2, SEQ ID NO. 10/SEQ ID NO. 2, SEQ ID NO. 11/SEQ ID NO. 2, SEQ ID NO. 12/SEQ ID NO. 2, SEQ ID NO. 13/SEQ ID NO. 2, SEQ ID NO. 14/SEQ ID NO. 2, SEQ ID NO. 15/SEQ ID NO. 2, SEQ ID NO. 8/SEQ ID NO. 16, SEQ ID NO. 9/SEQ ID NO. 16, SEQ ID NO. 10/SEQ ID NO. 16, SEQ ID NO. 11/SEQ ID NO. 16, SEQ ID NO. 12/SEQ ID NO. 16, SEQ ID NO. 13/SEQ ID NO. 16, SEQ ID NO. 14/SEQ ID NO. 16, SEQ ID NO. 15/SEQ ID NO. 16, SEQ ID NO. 8/SEQ ID NO. 32, SEQ ID NO. 9/SEQ ID NO. 32, SEQ ID NO. 10/SEQ ID NO. 32, SEQ ID NO. 11/SEQ ID NO. 32, SEQ ID NO. 12/SEQ ID NO. 32, SEQ ID NO. 13/SEQ ID NO. 32, SEQ ID NO. 14/SEQ ID NO. 32, SEQ ID NO. 15/SEQ ID NO. 32, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 2, SEQ ID NO. 4/SEQ ID NO. 2, SEQ ID NO. 5/SEQ ID NO. 2, SEQ ID NO. 6/SEQ ID NO. 2, SEQ ID NO. 7/SEQ ID NO. 2, SEQ ID NO. 8/SEQ ID NO. 2, SEQ ID NO. 9/SEQ ID NO. 2, SEQ ID NO. 10/SEQ ID NO. 2, SEQ ID NO. 11/SEQ ID NO. 2, SEQ ID NO. 12/SEQ ID NO. 2, SEQ ID NO. 13/SEQ ID NO. 2, SEQ ID NO. 14/SEQ ID NO. 2, SEQ ID NO. 15/SEQ ID NO. 2, SEQ ID NO. 8/SEQ ID NO. 16, SEQ ID NO. 9/SEQ ID NO. 16, SEQ ID NO. 10/SEQ ID NO. 16, SEQ ID NO. 11/SEQ ID NO. 16, SEQ ID NO. 12/SEQ ID NO. 16, SEQ ID NO. 13/SEQ ID NO. 16, SEQ ID NO. 14/SEQ ID NO. 16, SEQ ID NO. 15/SEQ ID NO. 16, SEQ ID NO. 8/SEQ ID NO. 32, SEQ ID NO. 9/SEQ ID NO. 32, SEQ ID NO. 10/SEQ ID NO. 32, SEQ ID NO. 11/SEQ ID NO. 32, SEQ ID NO. 12/SEQ ID NO. 32, SEQ ID NO. 13/SEQ ID NO. 32, SEQ ID NO. 14/SEQ ID NO. 32, SEQ ID NO. 15/SEQ ID NO. 32, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, and combinations thereof.

Preferably, the broad spectrum of mammalian cancers to be treated is selected from the group consisting of ovarian, colon, breast, lung cancers, myelomas, neuroblastic-derived CNS tumors, monocytic leukemias, B-cell derived leukemias, T-cell derived leukemias, B-cell derived lymphomas, T-cell derived lymphomas, mast cell derived tumors, and combinations thereof. Preferably, the autoimmune disease or inflammatory disease is selected from the group consisting of intestinal mucosal inflammation, wasting disease associated with colitis, multiple sclerosis, systemic lupus erythematosus, viral infections, rheumatoid arthritis, osteoarthritis, psoriasis, Cohn's disease, and inflammatory bowel disease.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics, Volume* 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, $5^{th}$ Ed., US Dept. of Health and Human Services, PHS, NIH, NIH Publication no. 91-3242, 1991. Other numbering systems for the amino acids in immunoglobulin chains include IMGT® (international ImMunoGeneTics information system; Lefranc et al, *Dev. Comp. Immunol.* 29:185-203; 2005) and AHo (Honegger and Pluckthun, *J. Mol. Biol.* 309(3):657-670; 2001).

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific." Monospecfic antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or VL domain (U.S. Pat. Nos. 6,846,634; 6,696,245, U.S. application Pub. Ser. No. 20/0202512; 2004/0202995; 2004/0038291; 2004/0009507; 2003/0039958, and Ward et al., *Nature* 341:544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, *Science* 242:423-26 and Huston et al., 1988, *Proc. Natl. Acad. Sci. USA* 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, *Proc. Natl. Acad. Sci. USA* 90:6444-48, and Poljak et al., 1994, *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. supra; Lefranc et al., supra and/or Honegger and Pluckthun, supra. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-CCR2 antibody. In another embodiment, all of the CDRs are derived from a human anti-CCR2 antibody. In another embodiment, the CDRs from more than one human anti-CCR2 antibodies are mixed and matched in a chimeric antibody. For instance, a chimeric antibody may comprise a CDR1 from the light chain of a first human anti-PAR-2 antibody, a CDR2 and a CDR3 from the light chain of a second human anti-CCR2 antibody, and the CDRs from the heavy chain from a third anti-CCR2 antibody. Other combinations are possible.

Further, the framework regions may be derived from one of the same anti-CCR2 antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody(-ies) from another species or belonging to another antibody class or subclass. Also included are fragments of such antibodies that exhibit the desired biological activity (i.e., the ability to specifically bind CCR2).

A "neutralizing antibody" or an "inhibitory antibody" is an antibody that inhibits the proteolytic activation of CCR2 when an excess of the anti-CCR2 antibody reduces the amount of activation by at least about 20% using an assay such as those described herein in the Examples. In various embodiments, the antigen binding protein reduces the amount of amount of proteolytic activation of CCR2 by at least 30%, 40%, 50%, 60%, 70%, 75%, 80%, 85%, 90%, 95%, 97%, 99%, and 99.9%.

Fragments or analogs of antibodies can be readily prepared by those of ordinary skill in the art following the teachings of this specification and using techniques known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, Bowie et al., 1991, *Science* 253:164.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human CCR2) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: *Methods in Enzymology* 185, Academic Press, San Diego, Calif. and Baron et al., 1995, *Nucleic Acids Res.* 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, *Cytotechnology* 28:31) or CHO strain DX-B11, which is deficient in DHFR (see Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (see McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Preferably, the mammalian cancer to be treated is selected from the group consisting of the osteosarcoma, rhabdomyosarcoma, neuroblastoma, any pediatric cancer, kidney cancer, leukemia, renal transitional cell cancer, Werner-Morrison syndrome, acromegaly, bladder cancer, Wilm's cancer, ovarian cancer, pancreatic cancer, benign prostatic hyperplasia, breast cancer, prostate cancer, bone cancer, lung cancer, gastric cancer, colorectal cancer, cervical cancer, synovial sarcoma, diarrhea associated with metastatic carcinoid, vasoactive intestinal peptide secreting tumors, gigantism, psoriasis, atherosclerosis, smooth muscle restenosis of blood vessels and inappropriate microvascular proliferation, head and neck cancer, squamous cell carcinoma, multiple myeloma, solitary plasmacytoma, renal cell cancer, retinoblastoma, germ cell tumors, hepatoblastoma, hepatocellular carcinoma, melanoma, rhabdoid tumor of the kidney, Ewing Sarcoma, chondrosarcoma, haemotological malignancy, chronic lymphoblastic leukemia, chronic myelomonocytic leukemia, acute lymphoblastic leukemia, acute lymphocytic leukemia, acute myelogenous leukemia, acute myeloblastic leukemia, chronic myeloblastic leukemia, Hodgekin's disease, non-Hodgekin's lymphoma, chronic lymphocytic leukemia, chronic myelogenous leukemia, myelodysplastic syndrome, hairy cell leukemia, mast cell leukemia, mast cell neoplasm, follicular lymphoma, diffuse large cell lymphoma, mantle cell lymphoma, Burkitt Lymphoma, mycosis fungoides, seary syndrome, cutaneous T-cell lymphoma, chronic myeloproliferative disorders, a central nervous system tumor, brain cancer, glioblastoma, non-glioblastoma brain cancer, meningioma, pituitary adenoma, vestibular schwannoma, a primitive neuroectodermal tumor, medulloblastoma, astrocytoma, anaplastic astrocytoma, oligodendroglioma, ependymoma and choroid plexus papilloma, a myeloproliferative disorder, polycythemia vera, thrombocythemia, idiopathic myelfibrosis, soft tissue sarcoma, thyroid cancer, endometrial cancer, carcinoid cancer, germ cell tumors, liver cancer, gigantism, psoriasis, atherosclerosis, smooth muscle restenosis of blood vessels, inappropriate microvascular proliferation, acromegaly, gigantism, psoriasis, atherosclerosis, smooth muscle restenosis of blood vessels or inappropriate microvascular proliferation, Grave's disease, multiple sclerosis, systemic lupus erythematosus, Hashimoto's Thyroiditis, Myasthenia Gravis, auto-immune thyroiditis and Bechet's disease.

As used herein, a "CCR2 mediated disorder" refers to a disorder involving the movement, e.g., recruitment from one site to another site, infiltration from one site to another site, proliferation, differentiation, and/or function of cells expressing CCR2. Cells expressing CCR2 include, for example, monocytes, dendritic cells, macrophages, T-cells, lymphocytes, basophils, mast cells, endothelial cells and fibroblasts. Examples of CCR2 mediated disorders include, but are not limited to, i) inflammatory or immune disorders; ii) cardiovascular disorders; iii) proliferative disorders; iv) graft rejections; v) fibrotic diseases; vi) viral infections; vii) neurological disorders; and viii) metabolic disorders.

Inflammatory disorders and conditions can be chronic or acute. Examples of inflammatory or immune disorders include, but are not limited to, respiratory diseases such as asthma, rhinitis, hypersensitivity lung diseases, hypersensitivity pneumonitis, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); inflammatory bowel diseases, such as Crohn's disease and ulcerative colitis; spondyloarthropathies; scleroderma; psoriasis and inflammatory dermatoses such as dermatitis, eczema, atopic dermatitis, urticaria; vasculitis (e.g., necrotizing, cutaneous, and hypersensitivity vasculitis); and inflammatory glomerulopathies.

Other examples of inflammatory or immune disorders include autoimmune disorders, such as arthritis (e.g., rheumatoid arthritis, psoriatic arthritis); multiple sclerosis; systemic lupus erythematosus; myasthenia gravis; juvenile onset diabetes; nephritides such as glomerulonephritis; autoimmune thyroiditis; acquired immune deficiency syndrome (AIDS) and Behcet's disease.

Still other examples of inflammatory or immune disorders include allergic diseases and conditions, such as respiratory allergic diseases such as asthma, allergic rhinitis, hypersensitivity lung diseases, and hypersensitivity pneumonitis; anaphylaxis or hypersensitivity responses; drug allergies (e.g., to penicillin, cephalosporins); insect sting allergies; allergic contact dermatitis; vasculitis (e.g., hypersensitivity vasculitis); and histamine and IgE-mediated allergic reactions.

Cardiovascular disorders include, but are not limited to atherogenesis; atherosclerosis; coronary artery disease; myocardial infarction; stroke; acute coronary syndrome; thrombosis; peripheral vascular disease of atherosclerotic origin; hypertension; and dyslipidemia.

Proliferative disorders include, but are not limited to cancers or tumors. "Cancer" or "tumor" is intended to include any neoplastic growth in a patient, including an initial tumor and any metastases. The cancer can be a cancer with leukocyte infiltration of the skin or organs. The cancer can be of the liquid or solid tumor type. Liquid tumors include tumors of hematological origin, including, e.g., myelomas (multiple myeloma), leukemias (e.g., Waldenstrom's syndrome, chronic lymphocytic leukemia, other leukemias), and lymphomas (e.g., B-cell lymphomas, non-Hodgkins lymphoma). Solid tumors can originate in organs, and include cancers such as lung, breast, prostate, ovary, colon, kidney, and liver. As used herein, cancer cells, including tumor cells, refer to cells that divide at an abnormal (increased) rate. Cancer cells include, but are not limited to, carcinomas, such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), and lymphomas (e.g., follicular lymphoma, mantle cell lymphoma, diffuse large Bcell lymphoma, malignant lymphoma, plasmocytoma, reticulum cell sarcoma, or Hodgkins disease); and tumors of the nervous system including glioma, meningoma, medulloblastoma, schwannoma or epidymoma.

Graft rejection (e.g., in transplantation) include but are not limited to allograft rejection or graft-versus-host disease.

Fibrotic diseases include, but are not limited to scleroderma.

Neurological disorders include, but are not limited to AIDS related dementia and pain (e.g. neuropathic pain).

Metabolic disorders include, but are not limited to diabetes.

Other diseases or conditions (including CCR2-mediated diseases or conditions) in which undesirable inflammatory responses are to be inhibited, include, but are not limited to, reperfusion injury; certain hematologic malignancies; cytokine-induced toxicity (e.g., septic shock, endotoxic shock); polymyositis; dermatomyositis; and granulomatous diseases including sarcoidosis.

Polypeptides of the present disclosure can be produced using any standard methods known in the art. In one example, the polypeptides are produced by recombinant DNA methods by inserting a nucleic acid sequence (e.g., a cDNA) encoding the polypeptide into a recombinant expression vector and expressing the DNA sequence under conditions promoting expression.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA.* 2003 100(2):438-42; Sinclair et al. *Protein Expr. Purif.* 2002 (1):96-105; Connell N D.

*Curr. Opin. Biotechnol.* 2001 12(5):446-9; Makrides et al. *Microbiol. Rev.* 1996 60(3):512-38; and Sharp et al. *Yeast.* 1991 7(7):657-78.

General techniques for nucleic acid manipulation are described for example in Sambrook et al., *Molecular Cloning: A Laboratory Manual*, Vols. 1-3, Cold Spring Harbor Laboratory Press, 2 ed., 1989, or F. Ausubel et al., *Current Protocols in Molecular Biology* (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, (Elsevier, N.Y., 1985).

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (*Bio/Technology*, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

CCR2-binding polypeptides can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See Raju et al. *Biochemistry.* 2001 31; 40(30):8868-76. Effects of such non-amino acid elements on the functionality of a polypeptide may be tested for its antagonizing role in CCR2 function.

In one specific embodiment, modified forms of the subject soluble polypeptides comprise linking the subject soluble polypeptides to nonproteinaceous polymers. In one specific embodiment, the polymer is polyethylene glycol ("PEG"), polypropylene glycol, or polyoxyalkylenes, in the manner as set forth in U.S. Pat. No. 4,640,835; 4,496,689; 4,301,144; 4,670,417; 4,791,192 or 4,179,337. Examples of the modified polypeptide include PEGylated VK-B8.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X-O(CH_2CH_2O)_n-1CH_2CH_2OH$ (1), where n is 20 to 2300 and X is H or a terminal modification, e.g., a $C_{1-4}$ alkyl. In one embodiment, the PEG of the invention terminates on one end with hydroxy or methoxy, i.e., X is H or $CH_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., *Bioconjugate Chem.* 6 (1995) 62-69).

Although PEG is well-known, this is, to our knowledge, the first demonstration that a pegylated$^{10F}$n3 polypeptide can be pegylated and retain ligand binding activity. In a preferred embodiment, the pegylated$^{10F}$n3 polypeptide is produced by site-directed pegylation, particularly by conjugation of PEG to a cysteine moiety at the N- or C-terminus. Accordingly, the present disclosure provides a target-binding $^{10F}$n3 polypeptide with improved pharmacokinetic properties, the polypeptide comprising: a $^{10F}$n3 domain having from about 80 to about 150 amino acids, wherein at least one of the loops of said $^{10F}$n3 domain participate in target binding; and a covalently bound PEG moiety, wherein said $^{10F}$n3 polypeptide binds to the target with a $K_D$ of less than 100 nM and has a clearance rate of less than 30 mL/hr/kg in a mammal. The PEG moiety may be attached to the $^{10F}$n3 polypeptide by site directed pegylation, such as by attachment to a Cys residue, where the Cys residue may be positioned at the N-terminus of the $^{0F}$n3 polypeptide or between the N-terminus and the most N-terminal beta or beta-like strand or at the C-terminus of the $^{10F}$n3 polypeptide or between the C-terminus and the most C-terminal beta or beta-like strand. A Cys residue may be situated at other positions as well, particularly any of the loops that do not participate in target binding. A PEG moiety may also be attached by other chemistry, including by conjugation to amines.

PEG conjugation to peptides or proteins generally involves the activation of PEG and coupling of the activated PEG-intermediates directly to target proteins/peptides or to a linker, which is subsequently activated and coupled to target proteins/peptides (see Abuchowski et al., *J. Biol. Chem.,* 252, 3571 (1977) and *J. Biol. Chem.,* 252, 3582 (1977), Zalipsky, et al., and Harris et. al., in: *Poly(ethylene glycol) Chemistry: Biotechnical and Biomedical Applications*; (J. M. Harris ed.) Plenum Press: New York, 1992; Chap. 21 and 22). It is noted that a binding polypeptide containing a PEG molecule is also known as a conjugated protein, whereas the protein lacking an attached PEG molecule can be referred to as unconjugated.

A variety of molecular mass forms of PEG can be selected, e.g., from about 1,000 Daltons (Da) to 100,000 Da (n is 20 to 2300), for conjugating to CCR2-binding polypeptides. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270).

In a specific embodiment of the disclosure an CCR2 binding polypeptide is covalently linked to one poly(ethylene glycol) group of the formula: $—CO—(CH_2)_x—(OCH_2CH_2)_m—OR$, with the —CO (i.e. carbonyl) of the poly(ethylene glycol) group forming an amide bond with one of the amino groups of the binding polypeptide; R being lower alkyl; x being 2 or 3; m being from about 450 to about 950; and n and m being chosen so that the molecular weight of the conjugate minus the binding polypeptide is from about 10 to 40 kDa. In one embodiment, a binding polypeptide's 6-amino group of a lysine is the available (free) amino group.

The above conjugates may be more specifically presented by formula (II): $P—NHCO—(CH_2)_x—(OCH_2CH_2)_m—OR$ (II), wherein P is the group of a binding polypeptide as described herein, (i.e. without the amino group or amino groups which form an amide linkage with the carbonyl shown in formula (II); and wherein R is lower alkyl; x is 2 or 3; m is from about 450 to about 950 and is chosen so that the molecular weight of the conjugate minus the binding polypeptide is from about 10 to about 40 kDa. As used herein, the given ranges of "m" have an orientational meaning. The ranges of "m" are determined in any case, and exactly, by the molecular weight of the PEG group.

One skilled in the art can select a suitable molecular mass for PEG, e.g., based on how the pegylated binding polypeptide will be used therapeutically, the desired dosage, circulation time, resistance to proteolysis, immunogenicity, and other considerations. For a discussion of PEG and its use to enhance the properties of proteins, see Katre, *Advanced Drug Delivery Reviews* 10: 91-114 (1993).

In one embodiment, PEG molecules may be activated to react with amino groups on a binding polypeptide, such as with lysines (Bencham et al., *Anal. Biochem.,* 131, 25 (1983); Veronese et al., *Appl. Biochem.,* 11, 141 (1985); Zalipsky et al., *Polymeric Drugs and Drug Delivery Systems*, adrs 9-110 ACS Symposium Series 469 (1999); Zalipsky et al., *Europ. Polym. J.,* 19, 1177-1183 (1983); Delgado et al., *Biotechnology and Applied Biochemistry,* 12, 119-128 (1990)).

In one specific embodiment, carbonate esters of PEG are used to form the PEG-binding polypeptide conjugates. N,N'-disuccinimidylcarbonate (DSC) may be used in the reaction with PEG to form active mixed PEG-succinimidyl carbonate that may be subsequently reacted with a nucleophilic group of a linker or an amino group of a binding polypeptide (see U.S. Pat. Nos. 5,281,698 and 5,932,462). In a similar type of reaction, 1,1'-(dibenzotriazolyl)carbonate and di-(2-pyridyl) carbonate may be reacted with PEG to form PEG-benzotriazolyl and PEG-pyridyl mixed carbonate (U.S. Pat. No. 5,382, 657), respectively.

Pegylation of a $^{10F}$n3 polypeptide can be performed according to the methods of the state of the art, for example by reaction of the binding polypeptide with electrophilically active PEGs (supplier: Shearwater Corp., USA, www.shearwatercorp.com). Preferred PEG reagents of the present invention are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini et al., *Bioconjugate Chem.* 6 (1995) 62-69). Such methods may used to pegylated at an f-amino group of a binding polypeptide lysine or the N-terminal amino group of the binding polypeptide.

In another embodiment, PEG molecules may be coupled to sulfhydryl groups on a binding polypeptide (Sartore et al., *Appl. Biochem. Biotechnol.,* 27, 45 (1991); Morpurgo et al., *Biocon. Chem.,* 7, 363-368 (1996); Goodson et al., *Bio/Technology* (1990) 8, 343; U.S. Pat. No. 5,766,897). U.S. Pat. Nos. 6,610,281 and 5,766,897 describes exemplary reactive PEG species that may be coupled to sulfhydryl groups.

In some embodiments where PEG molecules are conjugated to cysteine residues on a binding polypeptide, the cysteine residues are native to the binding polypeptide, whereas in other embodiments, one or more cysteine residues are engineered into the binding polypeptide. Mutations may be introduced into a binding polypeptide coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein. Alternatively, surface residues may be predicted by comparing the amino acid sequences of binding polypeptides, given that the crystal structure of the framework based on which binding polypeptides are designed and evolved has been solved (see Himanen et al., *Nature*. (2001) 20-27; 414(6866):933-8) and thus the surface-exposed residues identified. In one embodiment, cysteine residues are introduced into binding polypeptides at or near the N- and/or C-terminus, or within loop regions.

In some embodiments, the pegylated binding polypeptide comprises a PEG molecule covalently attached to the alpha amino group of the N-terminal amino acid. Site specific N-terminal reductive amination is described in Pepinsky et al., (2001) *JPET,* 297, 1059, and U.S. Pat. No. 5,824,784. The use of a PEG-aldehyde for the reductive amination of a protein utilizing other available nucleophilic amino groups is described in U.S. Pat. No. 4,002,531, in Wieder et al., (1979) *J. Biol. Chem.* 254,12579, and in Chamow et al., (1994) *Bioconjugate Chem.* 5, 133.

In another embodiment, pegylated binding polypeptide comprises one or more PEG molecules covalently attached to a linker, which in turn is attached to the alpha amino group of the amino acid residue at the N-terminus of the binding polypeptide. Such an approach is disclosed in U.S. Patent Publication 2002/0044921 and in WO094/01451.

In one embodiment, a binding polypeptide is pegylated at the C-terminus. In a specific embodiment, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., *Bioconjug. Chem.* 2004; 15(5):1005-1009.

Monopegylation of a binding polypeptide can also be produced according to the general methods described in WO 94/01451. WO 94/01451 describes a method for preparing a recombinant polypeptide with a modified terminal amino acid alpha-carbon reactive group. The steps of the method involve forming the recombinant polypeptide and protecting it with one or more biologically added protecting groups at the N-terminal alpha-amine and C-terminal alpha-carboxyl. The polypeptide can then be reacted with chemical protecting agents to selectively protect reactive side chain groups and thereby prevent side chain groups from being modified. The polypeptide is then cleaved with a cleavage reagent specific for the biological protecting group to form an unprotected terminal amino acid alpha-carbon reactive group. The unprotected terminal amino acid alpha-carbon reactive group is modified with a chemical modifying agent. The side chain protected terminally modified single copy polypeptide is then deprotected at the side chain groups to form a terminally modified recombinant single copy polypeptide. The number and sequence of steps in the method can be varied to achieve selective modification at the N- and/or C-terminal amino acid of the polypeptide.

The ratio of a binding polypeptide to activated PEG in the conjugation reaction can be from about 1:0.5 to 1:50, between from about 1:1 to 1:30, or from about 1:5 to 1:15. Various aqueous buffers can be used in the present method to catalyze the covalent addition of PEG to the binding polypeptide. In one embodiment, the pH of a buffer used is from about 7.0 to 9.0. In another embodiment, the pH is in a slightly basic range, e.g., from about 7.5 to 8.5. Buffers having a pKa close to neutral pH range may be used, e.g., phosphate buffer.

Conventional separation and purification techniques known in the art can be used to purify PEGylated binding polypeptide, such as size exclusion (e.g. gel filtration) and ion exchange chromatography. Products may also be separated using SDS-PAGE. Products that may be separated include mono-, di-, tri- poly- and un-pegylated binding polypeptide, as well as free PEG. The percentage of mono-PEG conjugates can be controlled by pooling broader fractions around the elution peak to increase the percentage of mono-PEG in the composition. About ninety percent mono-PEG conjugates represents a good balance of yield and activity. Compositions in which, for example, at least ninety-two percent or at least ninety-six percent of the conjugates are mono-PEG species may be desired. In an embodiment of this invention the percentage of mono-PEG conjugates is from ninety percent to ninety-six percent.

In one embodiment, PEGylated binding polypeptide of the invention contain one, two or more PEG moieties. In one embodiment, the PEG moiety(ies) are bound to an amino acid residue which is on the surface of the protein and/or away from the surface that contacts the target ligand. In one embodiment, the combined or total molecular mass of PEG in PEG-binding polypeptide is from about 3,000 Da to 60,000 Da, optionally from about 10,000 Da to 36,000 Da. In a one embodiment, the PEG in pegylated binding polypeptide is a substantially linear, straight-chain PEG.

In one embodiment of the invention, the PEG in pegylated binding polypeptide is not hydrolyzed from the pegylated amino acid residue using a hydroxylamine assay, e.g., 450 mM hydroxylamine (pH 6.5) over 8 to 16 hours at room temperature, and is thus stable. In one embodiment, greater than 80% of the composition is stable mono-PEG-binding polypeptide, more preferably at least 90%, and most preferably at least 95%.

In another embodiment, the pegylated binding polypeptides of the invention will preferably retain at least 25%, 50%, 60%, 70%, 80%, 85%, 90%, 95% or 100% of the biological activity associated with the unmodified protein. In one embodiment, biological activity refers to its ability to bind to CCR2, as assessed by KD, $k_{on}$ or $k_{off}$. In one specific embodiment, the pegylated binding polypeptide protein shows an increase in binding to CCR2 relative to unpegylated binding polypeptide.

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life ($t_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal.

Therapeutic Formulations and Modes of Administration

The present disclosure features methods for treating conditions or preventing pre-conditions which respond to an inhibition of CCR2 biological activity. Preferred examples are conditions that are characterized by inflammation or cellular hyperproliferation. Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

The composition can be in the form of a pill, tablet, capsule, liquid, or sustained release tablet for oral administration; or a liquid for intravenous, subcutaneous or parenteral administration; gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 µg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary, and will be ascertainable with routine experimentation by those skilled in the art.

Exemplary Uses

The CCR2 binding proteins described herein and their related variants are useful in a number of therapeutic and diagnostic applications. These include the inhibition of the biological activity of CCR2 by competing for or blocking the binding to a CCR2 as well as the delivery of cytotoxic or imaging moieties to cells, preferably cells expressing CCR2. The small size and stable structure of these molecules can be particularly valuable with respect to manufacturing of the drug, rapid clearance from the body for certain applications where rapid clearance is desired or formulation into novel delivery systems that are suitable or improved using a molecule with such characteristics.

On the basis of their efficacy as inhibitors of CCR2 biological activity, the polypeptides of this disclosure are effective against a number of cancer conditions as well as complications arising from cancer, such as pleural effusion and ascites. Preferably, the CCR2-binding polypeptides of the disclosure can be used for the treatment of prevention of hyperproliferative diseases or cancer and the metastatic spread of cancers. Preferred indications for the disclosed anti-CCR2 antibodies include colorectal cancers, head and neck cancers, small cell lung cancer, non-small cell lung cancer (NSCLC) and pancreatic cancer. Non-limiting examples of cancers include bladder, blood, bone, brain, breast, cartilage, colon kidney, liver, lung, lymph node, nervous tissue, ovary, pancreatic, prostate, skeletal muscle, skin, spinal cord, spleen, stomach, testes, thymus, thyroid, trachea, urogenital tract, ureter, urethra, uterus, or vaginal cancer.

In addition, various inflammatory disorders can be treated with the disclosed anti-CCR2 binding polypeptides disclosed herein. Such inflammatory disorders include, for example, intestinal mucosa inflammation wasting diseases associated with colitis, multiple sclerosis, systemic lupus erythematosus, viral infections, rheumatoid arthritis, osteoarthritis, psoriasis, and Crohn's disease.

A CCR2 binding polypeptide can be administered alone or in combination with one or more additional therapies such as chemotherapy radiotherapy, immunotherapy, surgical intervention, or any combination of these. Long-term therapy is equally possible as is adjuvant therapy in the context of other treatment strategies, as described above.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject anti-CCR2 antibodies agents of the invention can be used alone. Alternatively, the subject agents may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present disclosure recognizes that the effectiveness of conventional cancer therapies (e.g., chemotherapy, radiation therapy, phototherapy, immunotherapy, and surgery) can be enhanced through the use of a subject polypeptide therapeutic agent.

A wide array of conventional compounds have been shown to have anti-neoplastic activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a polypeptide therapeutic agent of the present invention is administered in combination with another conventional anti-neoplastic agent, either concomitantly or sequentially, such therapeutic agent may be found to enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

Certain chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes—dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); antiangiogenic compounds (TNP-470, genistein) and growth factor inhibitors (e.g., VEGF inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

Depending on the nature of the combinatory therapy, administration of the polypeptide therapeutic agents may be continued while the other therapy is being administered and/or thereafter. Administration of the polypeptide therapeutic agents may be made in a single dose, or in multiple doses. In some instances, administration of the polypeptide therapeutic agents is commenced at least several days prior to the conventional therapy, while in other instances, administration is begun either immediately before or at the time of the administration of the conventional therapy.

In one example of a diagnostic application, a biological sample, such as serum or a tissue biopsy, from a patient suspected of having a condition characterized by inappropriate angiogenesis is contacted with a detectably labeled polypeptide of the disclosure to detect levels of CCR2. The levels of CCR2 detected are then compared to levels of CCR2 detected in a normal sample also contacted with the labeled polypeptide. An increase of at least 10%, 20%, 30%, 40%, 50%, 60%, 70%, 80%, or 90% in the levels of the CCR2 may be considered a diagnostic indicator.

In certain embodiments, the CCR2 binding polypeptides are further attached to a label that is able to be detected (e.g., the label can be a radioisotope, fluorescent compound, enzyme or enzyme co-factor). The active moiety may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{125}$I, $^{131}$I, $^{132}$I, or $^{99}$Tc. A binding agent affixed to such a moiety may be used as an imaging agent and is administered in an amount effective for diagnostic use in a mammal such as a human and the localization and accumulation of the imaging agent is then detected. The localization and accumulation of the imaging agent may be detected by radio scintigraphy, nuclear magnetic resonance imaging, computed tomography or positron emission tomography. Immunoscintigraphy using CCR2 binding polypeptides directed at CCR2 may be used to detect and/or diagnose cancers and vasculature. For example, any of the binding polypeptide against a CCR2 marker labeled with $^{99}$Technetium, $^{111}$Indium, or $^{125}$Iodine may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, preferably 1-10 millicuries, most often 2-5 millicuries are administered. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

The CCR2 binding polypeptides can also be used to deliver additional therapeutic agents (including but not limited to drug compounds, chemotherapeutic compounds, and radiotherapeutic compounds) to a cell or tissue expressing CCR2. In one example, the CCR2 binding polypeptide is fused to a chemotherapeutic agent for targeted delivery of the chemotherapeutic agent to a tumor cell or tissue expressing CCR2.

The CCR2 binding polypeptides are useful in a variety of applications, including research, diagnostic and therapeutic applications. For instance, they can be used to isolate and/or purify receptor or portions thereof, and to study receptor structure (e.g., conformation) and function.

In certain aspects, the various binding polypeptides can be used to detect or measure the expression of CCR2, for example, on endothelial cells (e.g., venous endothelial cells), or on cells transfected with a CCR2 gene. Thus, they also have utility in applications such as cell sorting and imaging (e.g., flow cytometry, and fluorescence activated cell sorting), for diagnostic or research purposes.

In certain embodiments, the binding polypeptides of fragments thereof can be labeled or unlabeled for diagnostic purposes. Typically, diagnostic assays entail detecting the formation of a complex resulting from the binding of a binding polypeptide to CCR2. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides of the present invention can be utilized in enzyme immunoassays, wherein the subject polypeptides are conjugated to an enzyme. When a biological sample comprising a CCR2 protein is combined with the subject binding polypeptides, binding occurs between the binding polypeptides and the CCR2 protein. In one embodiment, a sample containing cells expressing a CCR2 protein (e.g., endothelial cells) is combined with the subject antibodies, and binding occurs between the binding polypeptides and cells bearing a CCR2 protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labeled polypeptide (e.g., an antibody) can be added which recognizes the subject binding polypeptide.

In certain aspects, kits for use in detecting the presence of a CCR2 protein in a biological sample can also be prepared. Such kits will include a CCR2 binding polypeptide which binds to a CCR2 protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the binding polypeptides and/or antibodies can be provided as a lyophilized mixture with the adjunct ingredients, or the adjunct ingredients can be separately provided for combination by the user. Generally these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

Similarly, the present disclosure also provides a method of detecting and/or quantitating expression of CCR2, wherein a composition comprising a cell or fraction thereof (e.g., membrane fraction) is contacted with a binding polypeptide which binds to a CCR2 or portion of the receptor under conditions appropriate for binding thereto, and the binding is monitored. Detection of the binding polypeptide, indicative of the formation of a complex between binding polypeptide and CCR2 or a portion thereof, indicates the presence of the receptor. Binding of a polypeptide to the cell can be determined by standard methods, such as those described in the working examples. The method can be used to detect expression of CCR2 on cells from an individual. Optionally, a quantitative expression of CCR2 on the surface of endothelial cells can be evaluated, for instance, by flow cytometry, and the staining intensity can be correlated with disease susceptibility, progression or risk.

The present disclosure also provides a method of detecting the susceptibility of a mammal to certain diseases. To illustrate, the method can be used to detect the susceptibility of a mammal to diseases which progress based on the amount of CCR2 present on cells and/or the number of CCR2-positive cells in a mammal.

Polypeptide sequences are indicated using standard one- or three-letter abbreviations. Unless otherwise indicated, each polypeptide sequence has amino termini at the left and a carboxy termini at the right; each single-stranded nucleic acid sequence, and the top strand of each double-stranded nucleic acid sequence, has a 5' termini at the left and a 3' termini at the right. A particular polypeptide sequence also can be described by explaining how it differs from a reference sequence.

The following terms, unless otherwise indicated, shall be understood to have the following meanings:

The terms "CCR2 inhibitor" and "CCR2 antagonist" are used interchangeably. Each is a molecule that detectably inhibits at least one function of CCR2. Conversely, a "CCR2 agonist" is a molecule that detectably increases at least one function of CCR2. The inhibition caused by a CCR2 inhibitor need not be complete so long as it is detectable using an assay. Any assay of a function of CCR2 can be used, examples of which are provided herein. Examples of functions of CCR2 that can be inhibited by a CCR2 inhibitor, or increased by a CCR2 agonist, include cancer cell growth or apoptosis (programmed cell death), and so on. Examples of types of CCR2 inhibitors and CCR2 agonists include, but are not limited to, CCR2 binding polypeptides such as antigen binding proteins (e.g., CCR2 inhibiting antigen binding proteins), antibodies, antibody fragments, and antibody derivatives.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

A "variant" of a polypeptide (for example, an antibody) comprises an amino acid sequence wherein one or more amino acid residues are inserted into, deleted from and/or substituted into the amino acid sequence relative to another polypeptide sequence. Disclosed variants include, for example, fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Preferably, the anti-CCR2 antibodies disclosed herein are characterized by their variable domain region sequences in the heavy $V_H$ and light $V_L$ amino acid sequences. The preferred antibody is A6 which is a kappa IgG antibody. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site such that an intact immunoglobulin has two binding sites.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human CCR2) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

A "host cell" is a cell that can be used to express a nucleic acid. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (Rasmussen et al., 1998, *Cytotechnology* 28:31) or CHO strain DX-B11, which is deficient in DHFR (Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (McMahan et al., 1991, *EMBO J.* 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Antigen Binding Proteins

Antigen binding proteins (e.g., antibodies, antibody fragments, antibody derivatives, antibody muteins, and antibody variants) are polypeptides that bind to CCR2, (preferably, human CCR2). Antigen binding proteins include antigen binding proteins that inhibit a biological activity of CCR2.

Oligomers that contain one or more antigen binding proteins may be employed as CCR2 antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have CCR2 binding activity.

In one embodiment, an oligomer is prepared using polypeptides derived from immunoglobulins. Preparation of Fusion Proteins Comprising Certain Heterologous Polypeptides Fused to Various Portions of antibody-derived polypeptides (including the Fc domain) has been described, e.g., by Ashkenazi et al., 1991, *Proc. Natl. Acad. Sci. USA* 88:10535; Byrn et al., 1990, *Nature* 344:677; and Hollenbaugh et al., 1992 "Construction of Immunoglobulin Fusion Proteins", in *Current Protocols in Immunology*, Suppl. 4, pages 10.19.1-10.19.11.

One embodiment is directed to a dimer comprising two fusion proteins created by fusing a CCR2 binding fragment of an anti-CCR2 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al., 1994, *FEBS Letters* 344:191. The use of a modified leucine zipper that allows for stable trimerization of a heterologous protein fused thereto is described in Fanslow et al., 1994, *Semin. Immunol.* 6:267-78. In one approach, recombinant fusion proteins comprising an anti-CCR2 antibody fragment or derivative fused to a leucine zipper peptide are expressed in suitable host cells, and the soluble oligomeric anti-CCR2 antibody fragments or derivatives that form are recovered from the culture supernatant.

Antigen-binding fragments of antigen binding proteins of the invention may be produced by conventional techniques. Examples of such fragments include, but are not limited to, Fab and $F(ab')_2$ fragments.

The present disclosure provides monoclonal antibodies that bind to CCR2. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4

1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Antigen binding proteins directed against CCR2 can be used, for example, in assays to detect the presence of CCR2 polypeptides, either in vitro or in vivo. The antigen binding proteins also may be employed in purifying CCR2 proteins by immunoaffinity chromatography. Blocking antigen binding proteins can be used in the methods disclosed herein. Such antigen binding proteins that function as CCR2 antagonists may be employed in treating any CCR2-induced condition, including but not limited to various cancers.

Antigen binding proteins may be employed in an in vitro procedure, or administered in vivo to inhibit CCR2-induced biological activity. Disorders caused or exacerbated (directly or indirectly) by the proteolytic activation of CCR2, examples of which are provided herein, thus may be treated. In one embodiment, the present invention provides a therapeutic method comprising in vivo administration of a CCR2 blocking antigen binding protein to a mammal in need thereof in an amount effective for reducing an CCR2-induced biological activity.

Antigen binding proteins include fully human monoclonal antibodies that inhibit a biological activity of CCR2.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, *Cell* 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, *EMBO J.* 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of CCR2 bound thereto. Polypeptides contemplated for use herein include substantially homogeneous recombinant mammalian anti-CCR2 antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-CCR2 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544, de Graaf et al., 2002, *Methods Mol. Biol.* 178:379-87.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, *Methods Mol. Biol.* 178:303-16). Moreover, if an IgG4 is desired, it may also be desired to introduce a point mutation (CPSCP→CPPCP) in the hinge region (Bloom et al., 1997, *Protein Science* 6:407) to alleviate a tendency to form intra-H chain disulfide bonds that can lead to heterogeneity in the IgG4 antibodies.

In particular embodiments, antigen binding proteins of the present invention have a binding affinity ($K_a$) for CCR2 of at least $10^6$. In other embodiments, the antigen binding proteins exhibit a $K_a$ of at least $10^7$, at least $10^8$, at least $10^9$, or at least $10^{10}$. In another embodiment, the antigen binding protein exhibits a $K_a$ substantially the same as that of an antibody described herein in the Examples.

In another embodiment, the present disclosure provides an antigen binding protein that has a low dissociation rate from CCR2. In one embodiment, the antigen binding protein has a $K_{off}$ of $1 \times 10^{-4}$ to $^{-1}$ or lower. In another embodiment, the $K_{off}$ is $5 \times 10^{-5}$ to $^{-1}$ or lower. In another embodiment, the $K_{off}$ is substantially the same as an antibody described herein. In another embodiment, the antigen binding protein binds to CCR2 with substantially the same $K_{off}$ as an antibody described herein.

In another aspect, the present disclosure provides an antigen binding protein that inhibits an activity of CCR2. In one embodiment, the antigen binding protein has an $IC_{50}$ of 1000 nM or lower. In another embodiment, the $IC_{50}$ is 100 nM or lower; in another embodiment, the $IC_{50}$ is 10 nM or lower. In another embodiment, the $IC_{50}$ is substantially the same as that of an antibody described herein in the Examples. In another embodiment, the antigen binding protein inhibits an activity of CCR2 with substantially the same $IC_{50}$ as an antibody described herein.

In another aspect, the present disclosure provides an antigen binding protein that binds to human CCR2 expressed on the surface of a cell and, when so bound, inhibits CCR2 signaling activity in the cell without causing a significant reduction in the amount of CCR2 on the surface of the cell. Any method for determining or estimating the amount of CCR2 on the surface and/or in the interior of the cell can be used. In other embodiments, binding of the antigen binding protein to the CCR2-expressing cell causes less than about 75%, 50%, 40%, 30%, 20%, 15%, 10%, 5%, 1%, or 0.1% of the cell-surface CCR2 to be internalized.

In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO00/09560, incorporated by reference herein.

The present disclosure further provides multi-specific antigen binding proteins, for example, bispecific antigen binding protein, e.g., antigen binding protein that bind to two different epitopes of CCR2, or to an epitope of CCR2 and an epitope of another molecule, via two different antigen binding sites or regions. Moreover, bispecific antigen binding protein as disclosed herein can comprise a CCR2 binding site from one of the herein-described antibodies and a second CCR2 binding region from another of the herein-described antibodies, including those described herein by reference to other publications. Alternatively, a bispecific antigen binding protein may comprise an antigen binding site from one of the herein described antibodies and a second antigen binding site from another CCR2 antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, *Nature* 305:537, and chemical coupling of antibody fragments (Brennan et al., 1985, *Science* 229:81; Glennie et al., 1987, *J. Immunol.* 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, *J. Immunol.* 148:1547) or other lock and key interactive domain structures as described in U.S. Pat. No. 5,582,996. Additional useful techniques include those described in U.S. Pat. Nos. 5,959,083; and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly (n-vinyl pyurrolidone), polyethylene glycols, propropylene glycol homopolymers, polypropylene oxide/ethylene oxide co-polymers, polyoxyethylated polyols and polyvinyl alcohols.

The following terms, unless otherwise indicated, shall be understood to have the following meanings:

Indications

In one aspect, the present disclosure provides methods of treating a subject. The method can, for example, have a generally salubrious effect on the subject, e.g., it can increase the subject's expected longevity. Alternatively, the method can, for example, treat, prevent, cure, relieve, or ameliorate ("treat") a disease, disorder, condition, or illness ("a condition"). Among the conditions to be treated are conditions characterized by inappropriate expression or activity of CCR2. In some such conditions, the expression or activity level is too high, and the treatment comprises administering a CCR2 antagonist as described herein. The disorders or conditions are cancer-related. In particular, those cancers include, but are not limited to, lung, ovarian and colon carcinoma and various myelomas.

Specific medical conditions and diseases that are treatable or preventable with the antigen binding proteins of this disclosure include various cancers.

Therapeutic Methods and Administration of Antigen Binding Proteins

Certain methods provided herein comprise administering a CCR2 binding antigen binding protein to a subject, thereby reducing a CCR2-induced biological response that plays a role in a particular condition. In particular embodiments, methods of the invention involve contacting endogenous CCR2 with a CCR2 binding antigen binding protein, e.g., via administration to a subject or in an ex vivo procedure.

The term "treatment" encompasses alleviation or prevention of at least one symptom or other aspect of a disorder, or reduction of disease severity, and the like. An antigen binding protein need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient.

One embodiment of the invention is directed to a method comprising administering to a patient a CCR2 antagonist in an amount and for a time sufficient to induce a sustained improvement over baseline of an indicator that reflects the severity of the particular disorder.

As is understood in the pertinent field, pharmaceutical compositions comprising the antibodies and fragments thereof of the disclosure are administered to a subject in a manner appropriate to the indication. Pharmaceutical compositions may be administered by any suitable technique, including but not limited to, parenterally, topically, or by inhalation. If injected, the pharmaceutical composition can be administered, for example, via intra-articular, intravenous, intramuscular, intralesional, intraperitoneal or subcutaneous routes, by bolus injection, or continuous infusion. Localized administration, e.g. at a site of disease or injury is contemplated, as are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including pills, syrups, lozenges or chewing gum; and topical preparations such as lotions, gels, sprays, and ointments.

Use of antigen binding proteins in ex vivo procedures also is contemplated. For example, a patient's blood or other bodily fluid may be contacted with an antigen binding protein that binds CCR2 ex vivo. The antigen binding protein may be bound to a suitable insoluble matrix or solid support material.

Advantageously, antigen binding proteins are administered in the form of a composition comprising one or more additional components such as a physiologically acceptable carrier, excipient or diluent. Optionally, the composition additionally comprises one or more physiologically active agents, for example, a second inflammation- or immune-inhibiting substance, an anti-angiogenic substance, an analgesic substance, etc., non-exclusive examples of which are provided herein. In various particular embodiments, the composition comprises one, two, three, four, five, or six physiologically active agents in addition to a CCR2 binding antigen binding protein Combination Therapy In another aspect, the present disclosure provides a method of treating a subject with a CCR2 inhibiting antigen binding protein and one or more other treatments. In one embodiment, such a combination therapy achieves synergy or an additive effect by, for example, attacking multiple sites or molecular targets in a tumor. Types of combination therapies that can be used in connection with the present invention include inhibiting or activating (as appropriate) multiple nodes in a single disease-related pathway, multiple pathways in a target cell, and multiple cell types within a target tissue.

In another embodiment, a combination therapy method comprises administering to the subject two, three, four, five, six, or more of the CCR2 agonists or antagonists described herein. In another embodiment, the method comprises administering to the subject two or more treatments that together inhibit or activate (directly or indirectly) CCR2-mediated signal transduction. Examples of such methods include using combinations of two or more CCR2 inhibiting antigen binding proteins, of a CCR2 inhibiting antigen binding protein and one or more other therapeutic moiety having anti-cancer properties (for example, cytotoxic agents, and/or immunomodulators), or of a CCR2 inhibiting antigen binding protein and one or more other treatments (e.g., surgery, or radiation). Furthermore, one or more anti-CCR2 antibodies or antibody derivatives can be used in combination with one or more molecules or other treatments, wherein the other molecule(s) and/or treatment(s) do not directly bind to or affect CCR2, but which combination is effective for treating or preventing the condition being treated. In one embodiment, one or more of the molecule(s) and/or treatment(s) treats or prevents a condition that is caused by one or more of the other molecule(s) or treatment(s) in the course of therapy, e.g., nausea, fatigue, alopecia, cachexia, insomnia, etc. In every case where a combination of molecules and/or other treatments is used, the individual molecule(s) and/or treatment(s) can be administered in any order, over any length of time, which is effective, e.g., simultaneously, consecutively, or alternately. In one embodiment, the method of treatment comprises completing a first course of treatment with one molecule or other treatment before beginning a second course of treatment. The length of time between the end of the first course of treatment and beginning of the second course of treatment can be any length of time that allows the total course of therapy to be effective, e.g., seconds, minutes, hours, days, weeks, months, or even years.

In another embodiment, the method comprises administering one or more of the CCR2 antagonists described herein and one or more other treatments (e.g., a therapeutic or palliative treatment). Where a method comprises administering more than one treatment to a subject, it is to be understood that the order, timing, number, concentration, and volume of the administrations is limited only by the medical requirements and limitations of the treatment, i.e., two treatments can be administered to the subject, e.g., simultaneously, consecutively, alternately, or according to any other regimen.

Example 1

This example shows a cellular binding assay to determine the $EC_{50}$ for anti-CCR2 antibodies. The data in FIG. 1 illustrates in vitro data for cellular binding $EC_{50}$ measurements. This example shows the binding characteristics for these antibodies in terms of the maximal cell binding and the concentration at which 50% binding saturation ($EC_{50}$) is reached. In this example, CHO-CCR2 cells were lifted from culture flasks using non-enzymatic Cell Dissociation Buffer—PBS based (Life Technologies #13151-014). Cells were resuspended in FACS Buffer (2% Fetal Bovine Serum in PBS) at $1\times10^6$ cells/ml and 100 µl ($1\times10^5$ cells) were aliquoted into the wells of a 96-well plate. Plated cells were spun down and the supernatant discarded. Cells were resuspended in 50 µl FACS Buffer containing the indicated concentrations of CCR2 D1 IgG in triplicate (FIG. 1). Plates were incubated for 1 hr at 4° C., then washed 1× with FACS Buffer. Cells were resuspended in 50 µl goat anti-human IgG (γ-chain specific)-PE conjugated secondary antibody (Southern Biotech #2040-09) diluted 1:500 in FACS Buffer. Cells were further incubated for 30 min at 4° C. and then washed 1× with FACS Buffer. The cells were resuspended in a final volume of 25 µl FACS Buffer and analyzed using the Intellicyt Flow Cytometer. Median fluorescence in the FL-2H channel was determined using FlowJo software and $EC_{50}$ value was determined by plotting the data in GraphPad Prism and analyzing using a variable slope non-linear regression.

Results: The cellular binding $EC_{50}$ for the anti-CCR2 antibodies are shown in Table 1.

TABLE 1

| Antibody | $EC_{50}$ (nM) CHO-huCCR2 |
|---|---|
| D1 | 0.17 |
| D1-1/LO | 0.13 |
| D1-1/45H8L1 | 0.15 |

TABLE 1-continued

| Antibody | $EC_{50}$ (nM) CHO-huCCR2 |
|---|---|
| D1-2/LO | 16 |
| D1-4/LO | 1.6 |
| D1-6/LO | 3.5 |
| D1-7/LO | 0.08 |
| 1A2 | 2.9 |
| 1B2 | 0.36 |
| 1B11 | 2.3 |
| 1G11 | 0.34 |
| 1H5 | 1.3 |
| 42G7 | 15 |
| 43D12 | 1.8 |
| 54A9 | 0.53 |

Example 2

Example 2 shows in vitro data for cellular binding $EC_{50}$ measurements of anti-CCR2 antibodies against murine CCR2. This example shows whether these antibodies directed against human CCR2 can cross react with murine CCR2 as well as demonstrating the binding characteristic for these antibodies in terms of the maximal cell binding and the concentration at which 50% binding saturation ($EC_{50}$) is reached. In this example, WEHI 274.1 cells were resuspended in FACS Buffer (2% Fetal Bovine Serum in PBS) at $1\times10^6$ cells and 50 µl ($1\times10^5$ cells) of cell suspension was aliquoted into the wells of a 96-well plate. Plated cells were spun down and the supernatant discarded. Cells were resuspended in 30 µl FACS Buffer containing serially diluted anti-CCR2 IgGs in triplicate. Plates were incubated for 1 hr at 4° C., then washed 2× with FACS Buffer. Cells were resuspended in 50 µl goat anti-human IgG (γ-chain specific)-PE conjugated secondary antibody (Southern Biotech #2040-09) diluted 1:500 in FACS Buffer, incubated for 30 min at 4° C. and then washed 1× with FACS Buffer. The cells were resuspended in a final volume of 30 µl FACS Buffer and analyzed using the Intellicyt Flow Cytometer. Median fluorescence in the FL-2H channel was determined using FlowJo software and $EC_{50}$ values were determined by plotting the data in GraphPad Prism and analyzed using a variable slope non-linear regression. The results are shown in Table 2.

TABLE 2

| Antibody | $EC_{50}$ (nM) murine CCR2 |
|---|---|
| D1 | 1.5 |
| D1-1/LO | 4.8 |
| D1-1/45H8L1 | 2.0 |
| D1-2/LO | 81 |

Example 3

This example shows a calcium influx assay on THP-1 cells (human monocyte cell line). To measure $IC_{50}$ of D1 on MCP-1 induced THP-1 calcium mobilization, we first set up a MCP-1 induced THP-1 calcium flux assay to determine $EC_{50}$ of MCP-1. Under the assay conditions used for measuring $EC_{50}$ of MCP-1 described in the methods (calcium influx assay), $EC_{50}$ value 3.3 nM on MCP-1-induced calcium flux was obtained. We then used 10 nM of human MCP-1 (PROSPEC # CHM-271) (about $EC_{80}$) to conducted a calcium flux assay for determination of D1 $IC_{50}$ on MCP-1 induced THP-1 calcium mobilization.

Figure 2:
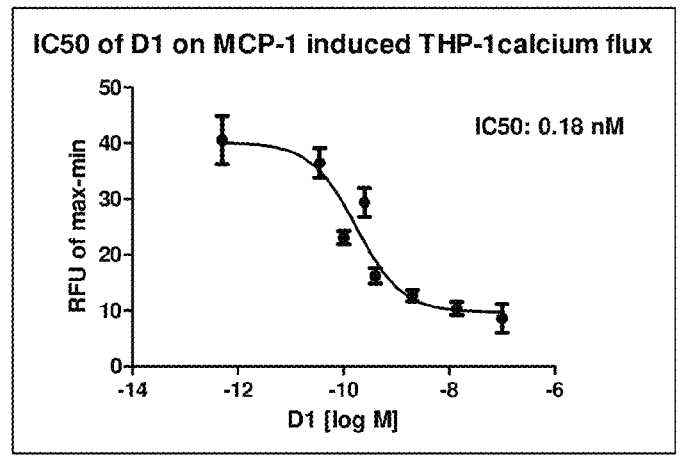
FIG. 2 shows cellular binding $EC_{50}$ for D1 against murine CCR2-expressing cells. The only anti-CCR2 antibody to bind to murine CCR2 was D1; all others antibodies showed no cellular staining. The cellular binding $EC_{50}$ for D1 against murine CCR2-expressing cells is approximately 17 nM (FIG. 2).

Results: Under the assay condition used for $IC_{50}$ of D1 described in the methods (calcium influx assay), an $IC_{50}$ value 4.7 nM of D1 on MCP-1-induced calcium flux was obtained from two independent experiments. Mean±S.D. of trilicate assays are presented in FIG. 2.

Example 4

This example provides primary human monocytes to measure $IC_{50}$ of D1 on MCP-1 induced primary human monocyte calcium mobilization. We first set up a MCP-1 induced primary human monocyte calcium flux assay to determine the $EC_{50}$ of MCP-1. Calcium influx assays were set up using a FLIPR calcium 4 assay kit and changes in intracellular $Ca^{2+}$ were measured with a FlexStation3 scanning fluorometer (Molecular Devices, Sunnyvale, Calif.). To determine the $EC_{50}$ of chemokine MCP-1, THP-1 cells or primary human monocytes in 25 µL of assay buffer (HBSS+20 mM HEPES) were loaded into a Poly-D-Lysine coated 384-well black wall, clear-bottom assay plate (Greiner) together with 25 µl of FLIPR calcium 4 assay kit (R8142, Molecular Devices) containing probenecid 3 mM (final in-well working concentration), and then incubated for 1 h at 37° C., 5% $CO_2$. After the incubation the assay plate was centrifuged 4 min at 1,000 rpm and incubated at room temperature for 10 min. A separate plate containing various doses of MCP-1 was set up. Both plates were then loaded into the FlexStation for automated addition of MCP-1 to the fluorescently labeled cells. Baseline fluorescence was established before MCP-1 were added to cells at 17 seconds. Quantitation of calcium release over time was determined by the SoftMax Pro software that powers the FlexStation3. Fold response was calculated by dividing the maximum-minimum fluorescence value for each MCP-1 concentration by the maximum-minimum fluorescence for buffer vehicle. $EC_{50}$ values of MCP-1 were calculated in GraphPad Prism 5 by plotting the fold responses for increasing MCP-1 concentrations and using the sigmoidal dose-response analysis.

To determinate $IC_{50}$ of D1, the cells were incubated with different doses of D1 in the HBSS+20 mM HEPES buffer for 20 min at room temperature prior to the loading 25 µl cells into the 384 well plate together with 25 µl of the FLIPR calcium 4 assay kit. Other procedures were the same as the ones in above $EC_{50}$ determination of chemokine MCP-1.

The detailed information of the assay conditions such as cell number, concentration of MCP-1 and D1, assay parameters and etc. are indicated in the figure legends. Under the assay conditions used for measuring $EC_{50}$ of MCP-1 described in the methods (calcium influx assay), the $EC_{50}$ value 3.79 nM on MCP-1-induced calcium flux was obtained. We then used 10 nM of MCP-1 (about $EC_{80}$) to conducted a calcium flux assay for determination of D1 $IC_{50}$ on MCP-1 induced primary human monocyte calcium mobilization.

Figure 3:
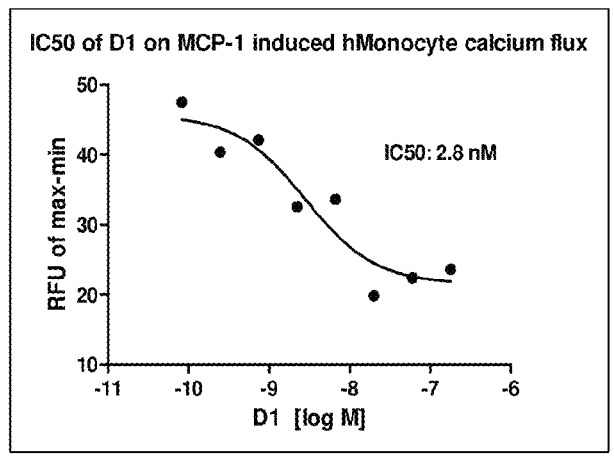
FIG. 3 shows a calcium assay using THP-1 cells. (A). $EC_{50}$ determination of MCP-1: THP-1 cells ($0.3 \times 10^5$ cells in 25 µl of the assay buffer) were incubated with 25 µl of Calcium 4 Assay kit including probenecid in a Poly-D-Lysine 384-well plate for 1 h at 37° C. 5% $CO_2$ followed by 15 minutes at room temperature and centrifugation. A 5× dose response of MCP-1 was added (12.5 µl/well) to achieve the final indicated concentrations.

Results: Under the assay condition used for $IC_{50}$ of D1 described in the methods (calcium influx assay), an $IC_{50}$ value 2.8 nM of D1 on MCP-1-induced calcium flux was obtained. Mean±S.D. of triplicate assays are presented in FIG. 3.

Example 5

This example shows a chemotaxis assay using THP-1 (human monocyte cell line) to measure the $IC_{50}$ of D1 on MCP-1 induced THP-1 cell migration. We first set up a MCP-1 induced THP-1 cell migration assay to determine $EC_{50}$ of MCP-1. Under the assay condition used for measuring $EC_{50}$ of MCP-1 described herein (chemotaxis assay), an $EC_{50}$ value 0.8 nM was achieved on MCP-1-induced chemotaxis.

We then used 3 nM of MCP-1 (about $EC_{80}$) to conduct a chemotaxis assay to determine an $IC_{50}$ of D1 on MCP-1 induced THP-1 cell migration.

Chemotaxis assays were set up using 96-well chemotaxis chamber (ChemoTX; NeuroProbe, Gaithersburg, Md.) with the 2 compartments separated by a 5-1 μm polycarbonate membrane. To determinate the $EC_{50}$ of chemokine MCP-1, 29 μl of assay buffer containing different doses of MCP-1 (shown in Figures) were added to the lower compartments. Membrane was aligned with wells and snapped into place. THP-1 or primary human monocyte cells resuspended in 25 μl of the assay buffer were added to the upper chamber wells. The lid was replaced and the plate is incubated at 37° C. 5% $CO_2$. After the incubation, the non-migrated cells remaining on the upper side of the membrane were blotted by filter paper and the membrane was detached from microplate and cell number in each well of the lower chamber was counted with Cedex. MCP-1 induced dose dependent curve and $EC_{50}$ value of MCP-1 was calculated by Prism5.

Figure 4:
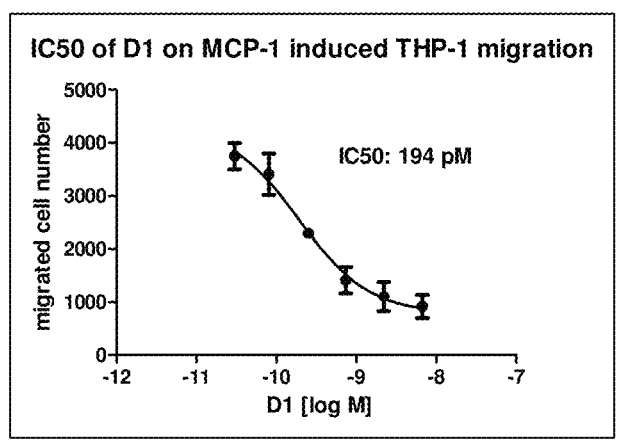
FIG. 4 shows a calcium assay using primary human monocytes. (A). $EC_{50}$ determination of MCP-1: human primary monocytes ($0.3 \times 10^5$ cells in 25 µl of the assay buffer) were incubated with 25 µl of Calcium 4 Assay kit including probenecid in a Poly-D-Lysine 384-well plate for 1 h at 37° C. 5% $CO_2$ followed by 15 minutes at room temperature and centrifugation. A 5× dose response of MCP-1 was added (12.5 µl/well) to achieve the final indicated concentrations.

Results: Under the assay condition used D1 had an $IC_{50}$ value 194 pM on MCP-1-induced chemotaxis. FIG. 4 represents one of three independent experiments to determine the D1 $IC_{50}$. An $IC_{50}$ value of D1 was similar in each of the three independent experiments.

Example 6

This example provides an $IC_{50}$ assay of D1 on MCP-1 induced primary human monocyte migration. We first set up a MCP-1 induced primary human monocyte migration assay to determine $EC_{50}$ of MCP-1. Under the assay condition used for measuring $EC_{50}$ of MCP-1 described in the methods (chemotaxis assay). We obtained an $EC_{50}$ value 0.389 nM on MCP-1-induced chemotaxis. We then used 1 nM of MCP-1 (about $EC_{80}$) to conduct a chemotaxis assay to determine a D1 $IC_{50}$ on MCP-1 induced primary human monocyte cell migration.

Figure 5:
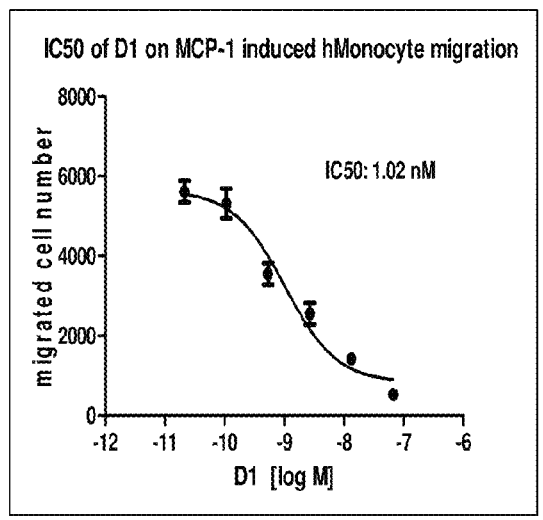
FIG. 5 shows a chemotaxis assay using THP-1 cells.
Figure 6:
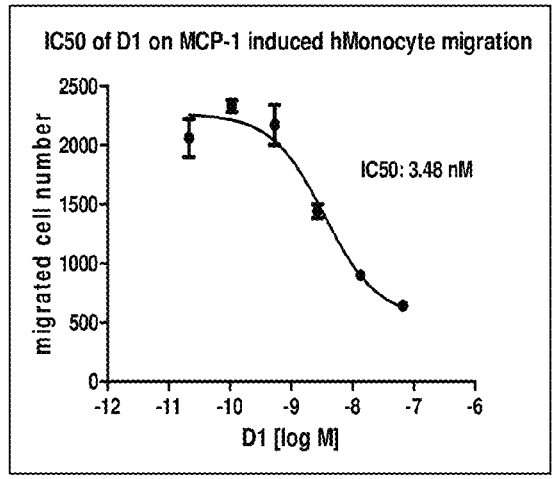
FIG. 6 shows a chemotaxis assay using primary human monocyte cells and is an $IC_{50}$ determination of D1: Different concentrations of D1 (0.03-6.7 nM) were pre-incubated with primary human monocyte cells ($0.1 \times 10^6$ cells in 25 µl per site) at room temperature for 20 min. MCP-1 at 1 nM was loaded in the wells of plate in the lower chambers, whereas the pre-incubated cells with D1 were loaded on top of membrane. After 1 h and 45 min incubation at 37° C., 5% $CO_2$, migrated cells were collected, counted and calculated using Prism 5.

Results: Under the assay condition used for $IC_{50}$ of D1 described herein (chemotaxis assay), an $IC_{50}$ value 1.02 nM for D1 on MCP-1-induced chemotaxis was obtained from monocytes isolated from a donor (FIG. 5) and an $IC_{50}$ value 3.48 nM for D1 on MCP-1-induced chemotaxis was obtained from monocytes isolated from another donor (FIG. 6).

Example 7

This example provides an $IC_{50}$ determination of D1 on mMCP-1 (mouse MCP-1) induced WEHI 274.1 (mouse monocyte cell line) cell migration assay. We first set up a mMCP-1 induced WEHI 274.1 cell migration assay to determine an $EC_{50}$ of mMCP-1.

Chemotaxis of WEHI 274.1 toward MCP-1 was performed with a fluorescent method. The cells ($5\times10^6$/ml) were labeled with 2 μM calcein-AM for 30 minutes at 37° C., 5% CO2 protected from light. Subsequently, cells were washed with HBSS and the cells resuspended in 25 μl of the assay buffer were added to the upper chamber wells. The assay procedures described above for THP-1 and primary human monocytes were followed. After the incubation at 37° C. 5% for migration, the non-migrated cells remaining on the upper side of the membrane were blotted by filter paper and top of the membrane was washed with PBS. The membrane was detached from plate and the fluorescence of the wells was measured from bottom of the membrane in a fluorescent plate reader (FlexStation3, Molecular Device) with excitation at 485 nm and emission at 530 nm.

Under the assay conditions used for measuring the $EC_{50}$ of mMCP-1 (described above), an $EC_{50}$ value of 0.12 nM on mMCP-1-induced chemotaxis was obtained. We then used 0.25 nM (~$EC_{80}$) of MCP-1 to conducted a chemotaxis assay for determination of an $IC_{50}$ for D1 using a mMCP-1 induced WEHI 274.1 cell migration assay.

Figure 7:
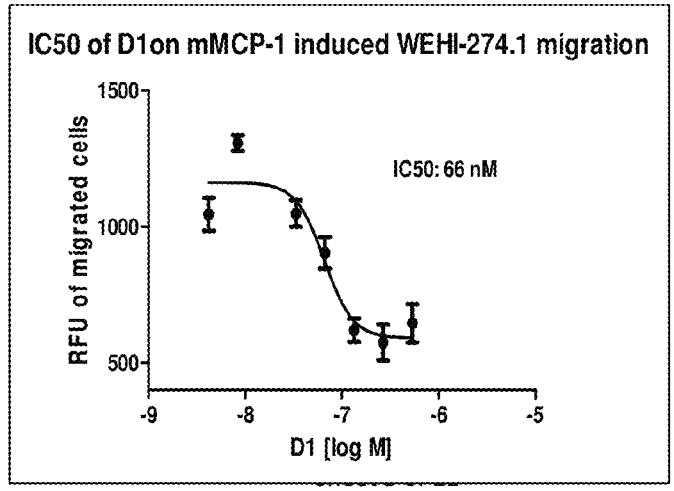
FIG. 7 shows a chemotaxis assay using WEHI 274.1 cells and is an $IC_{50}$ determination for D1. Different concentrations of D1 (4.0-534 nM) were pre-incubated with WEHI cells ($0.1 \times 10^6$ cells in 25 µl per site) at room temperature for 20 min. mMCP-1 at 2.5 nM was loaded in the wells of plate in the lower chambers, whereas the pre-incubated cells with D1 were loaded on top of membrane. After 2 h incubation at 37° C., 5% $CO_2$, migrated cells were collected, counted and calculated.
Figure 8A:
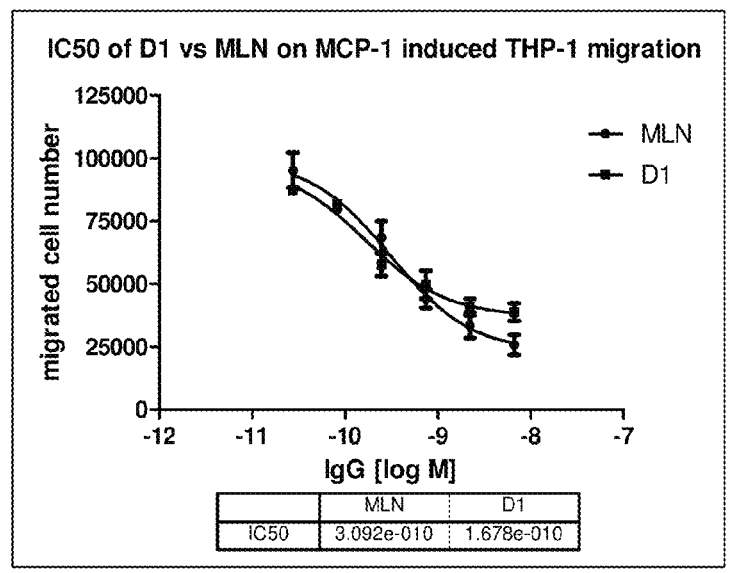
In FIG. 8A is an $IC_{50}$ determination of D1 versus MLN1202 on MCP-1 induced THP-1 cell migration.
Figure 8B:
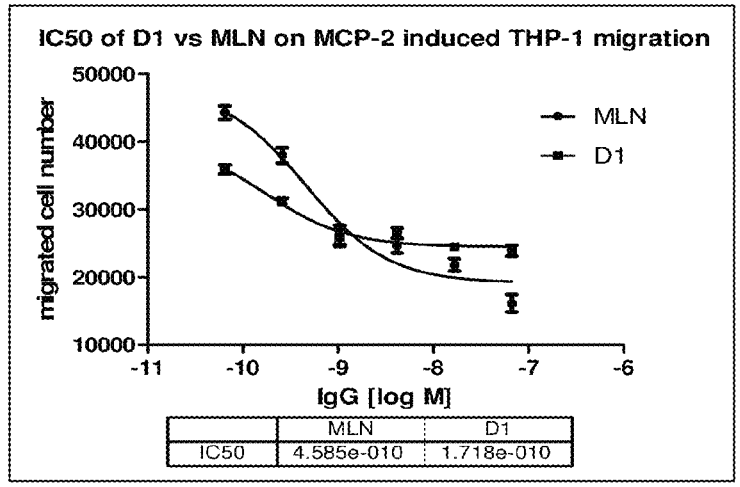
In FIG. 8B is an $IC_{50}$ determination of D1 versus MLN1202 on MCP-2 induced THP-1 cell migration.
Figure 8C:
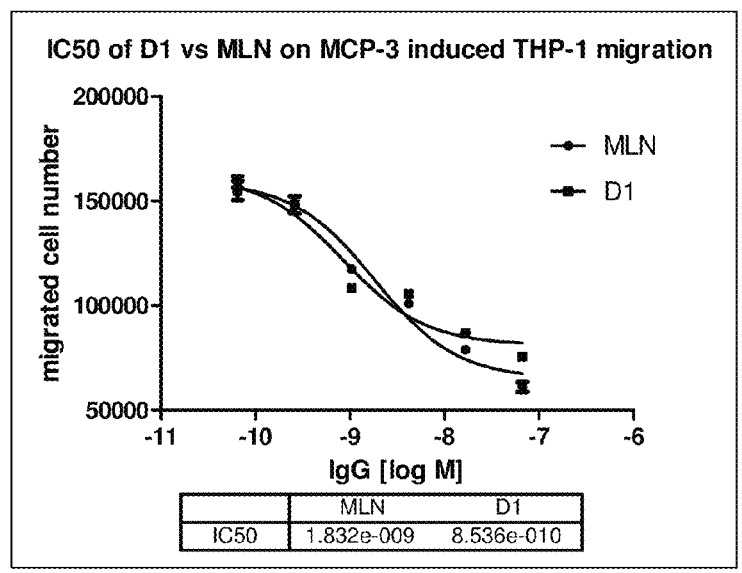
In FIG. 8C is an $IC_{50}$ determination of D1 versus MLN1202 on MCP-3 induced THP-1 cell migration.
Figure 8D:
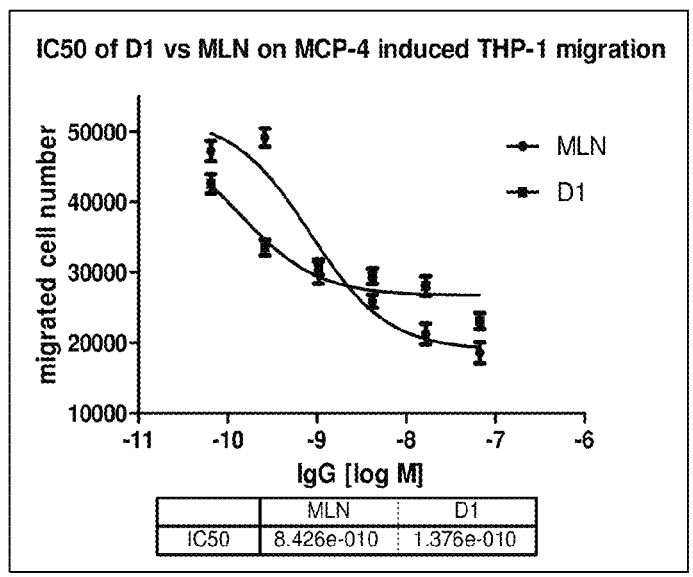
In FIG. 8D is an $IC_{50}$ determination of D1 versus MLN1202 on MCP-4 induced THP-1 cell migration.
Figure 8E:
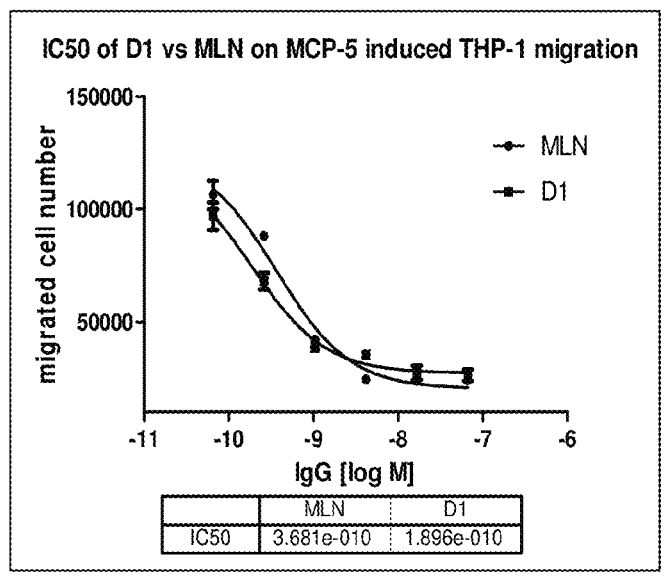
In FIG. 8E is an $IC_{50}$ determination of D1 versus MLN1202 on mouse MCP-5 induced THP-1 cell migration.

Results: Under the assay condition used for $IC_{50}$ of D1 described in the methods (chemotaxis assay), an $IC_{50}$ value of 66 nM was obtained for D1 (FIG. 7).

Example 8

This example provides a comparison of functional activity between D1 and MLN1202 with chemotaxis. MLN1202 (Millennium) is a humanized monoclonal antibody with high specificity to CCR2, which interrupts MCP-1 binding to CCR2. MLN1202 is being evaluated in clinical trials. To compare functional activity between D1 and MLN1202, we performed a chemotaxis assay with the CCR2 chemokines (MCP-1, MCP-2, MCP-3, MCP-4 and MCP-5) on induced THP-1 cell migration.

Chemotaxis assays were set up using 96-well chemotaxis chamber (ChemoTX; NeuroProbe, Gaithersburg, Md.) with the 2 compartments separated by a 5-1 μm polycarbonate membrane. To determinate the $EC_{50}$ of chemokine MCP-1, 29 μl of assay buffer containing different doses of MCP-1 (shown in Figures) were added to the lower compartments. The membrane was aligned with wells and snapped into place. THP-1 or primary human monocyte cells resuspended in 25 μl of the assay buffer were added to the upper chamber wells. The lid was replaced and the plate is incubated at 37° C. 5% $CO_2$. After the incubation, the non-migrated cells remaining on the upper side of the membrane were blotted by filter paper and the membrane was detached from microplate and cell number in each well of the lower chamber was counted with Cedex. The MCP-1 induced dose dependent curve and $EC_{50}$ value of MCP-1 was calculated by Prism5.

To determine the $IC_{50}$ of D1, the cells were incubated with different doses of D1 in the assay buffer for 20 min at room temperature prior to adding cells in 25 μl of the assay buffer to the upper chamber wells and one concentration of MCP-1 (around the $EC_{80}$) was added to the lower compartment. Other procedures were the same as the ones in the above $EC_{50}$ determination of chemokine MCP-1.

The $IC_{50}$ values of D1 and MLN1202 are indicated in FIGS. 8A, 8B, 8C, 8D and 8E. A comparison of the $IC_{50}$ values is shown in Table 3 below.

Results: The data in the FIGS. 8A-E as well as in Table 3 demonstrate that D1 was more potent than MLN1202 in the inhibition of these five CCR2 chemokine-induced THP-1 cell migration.

TABLE 3

$IC_{50}$ (in pM) comparison of D1 versus MLN1202 on MCPs induced THP-1 cell migration

|  | MCP-1 | MCP-2 | MCP-3 | MCP-4 | MCP-5 |
| --- | --- | --- | --- | --- | --- |
| $IC_{50}$ of D1 | 168 | 172 | 854 | 138 | 190 |
| $IC_{50}$ of MLN1202 | 309 | 459 | 1832 | 843 | 368 |

Example 9

Figure 9:
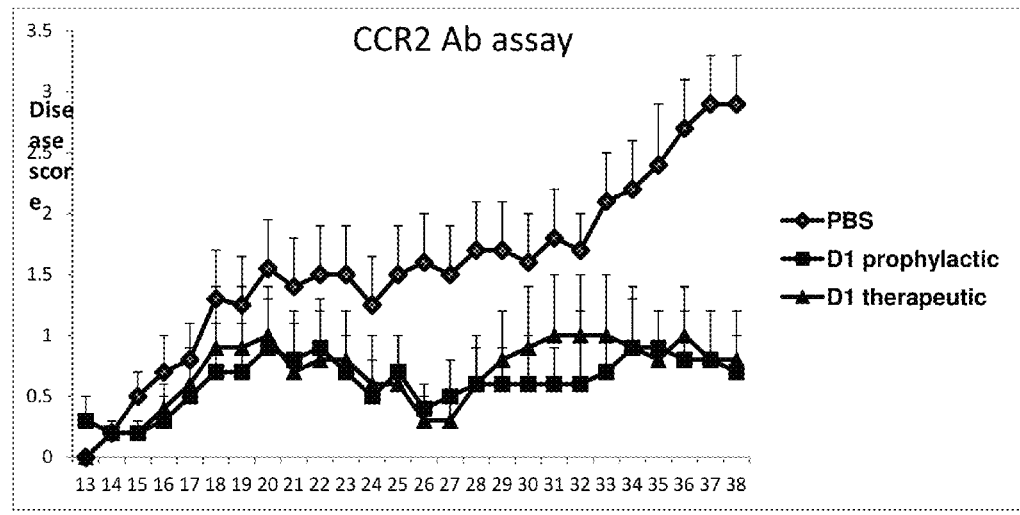
FIG. 9 shows the beneficial effect of anti-CCR2 antibody D1 in vivo in a murine EAE model for multiple sclerosis.

This example shows an in vivo EAE model for the D1 antibody. The ability of an antibody against CCR2 to influence the development of disease was tested by inducing experimental autoimmune encephalomyelitis (EAE) in C57B1/6 mice. This was achieved using a kit from Hooke laboratories (Lawrence, Mass.) whereby mice were injected with myelin oligodendrocyte glycoprotein (MOG) and pertussis toxin to promote neurological symptoms. EAE is a murine model of multiple sclerosis (MS) that replicates numerous key etiological components of the human disease. Mice were treated with the D1 antibody in one of two ways. In one treatment protocol mice were treated one day after disease induction (prophylactic) with the D1 antibody (0.1 mg) given every second day intraperitoneally. In the second treatment protocol (therapeutic) the antibody (0.1 mg) was given intraperitoneally when the mice showed evidence of disease (limp tail). This treatment was then given every second day. Throughout the experiment, mice were assessed every day and the disease score recorded. From FIG. 9 it is evident that the D1 treatment, either prophylactically or therapeutically, reduced the severity of disease.

Example 10

This example provides cellular binding $IC_{50}$ for antibodies 1G11, 1B2 and 1H5. The chemotaxis assay methods used for these antibodies were the same as the ones used for D1. To measure the $IC_{50}$ of the antibodies on MCPs induced THP-1 cell migration, we first set up the THP-1 cell migration assay to determine $EC_{50}$ of the MCP ligands. Under the assay condition used for measuring the $EC_{50}$ of MCP-1 described above (chemotaxis assay), an $EC_{50}$ value was determined (data not showed).

We then used the $EC_{80}$ concentrations of each MCP to conduct a chemotaxis assay for determining the $IC_{50}$ of the CCR2 antibodies 1G11, 1B2 and 1H5 on MCPs induced THP-1 cell migration.

Figure 10A:
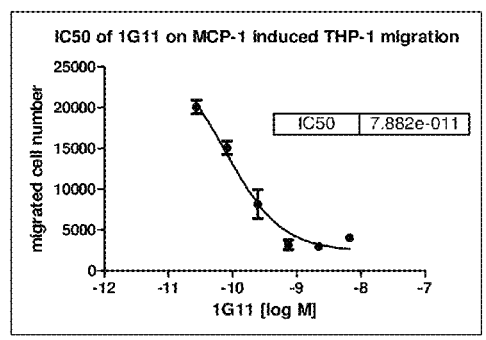
FIGS. 10-12 show various IC50 results for antibodies 1G11, 1B2, and 1H5. Specifically, $IC_{50}$ of 1G11 against MCP-1 (3 nM) was 79 pM (FIG. 10A) and against MCP-5 (6 ng/ml) was 261 pM (FIG. 10B). $IC_{50}$ of 1B2 against MCP-1 (3 nM) was 87 pM (FIG. 11A) and against MCP-5 (3 nM) was 197 pM (FIG. 11B). These $IC_{50}$ values demonstrate that 1G11 and 1B11 are more potent than D1 in MCP-1 and MCP-5 induced THP-1 migration. However, 1G11 and 1B2 do not have inhibition activities on MCP-2, 3 and 4 induced THP-1 migration (data not shown). $IC_{50}$ of 1H5 against MCP-1 (3 nM) was 109 pM (FIG. 12A) and against MCP-5 (6 ng/ml) was 349 pM (FIG. 12B). These $IC_{50}$ values are comparable to D1. 1H5 also demonstrated 1.9 nM $IC_{50}$ value against 30 ng/ml of MCP-2 (FIG. 2C), 2.6 nM $IC_{50}$ value against 6 ng/ml of MCP-3 (FIG. 12D) and 1.4 nM $IC_{50}$ against 200 ng/ml of MCP-4 (FIG. 12E).
Figure 10B:
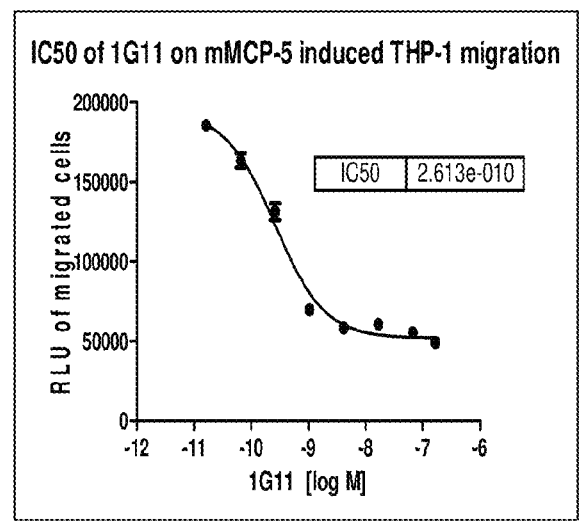
Figure 11A:
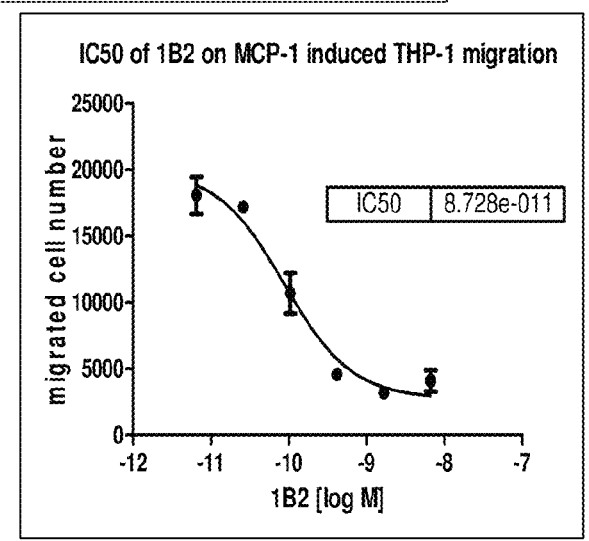
Figure 11B:
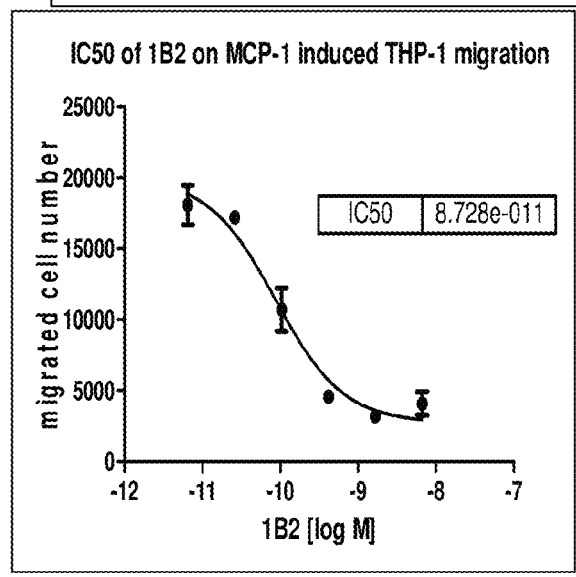
Figure 12A:
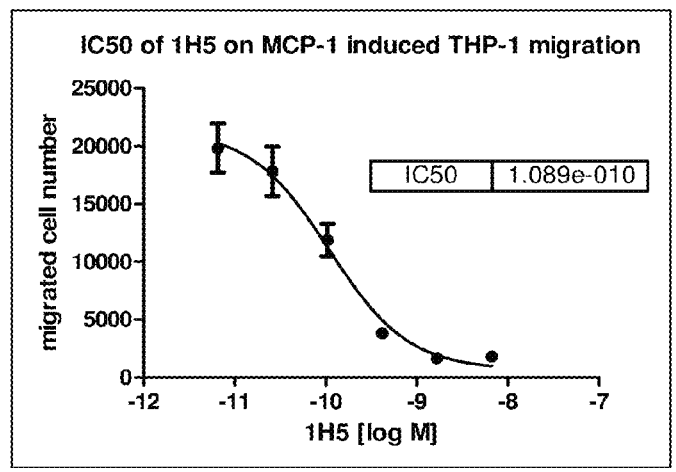
Figure 12B:
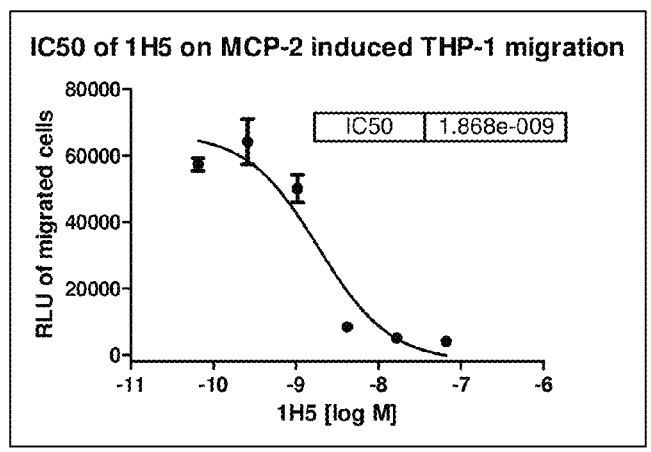
Figure 12C:
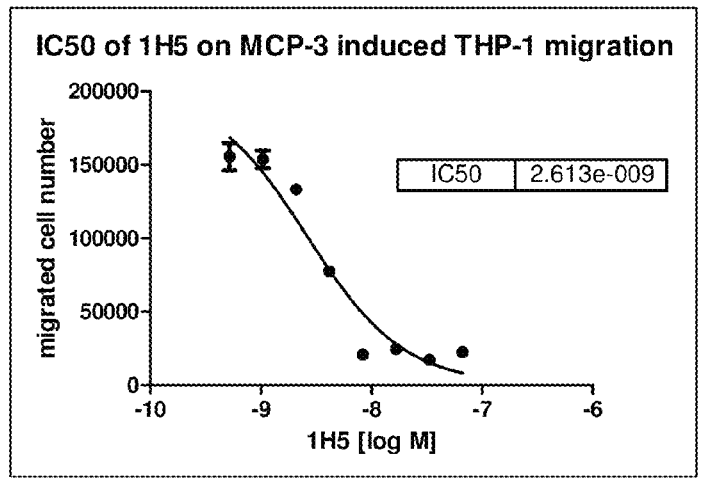
Figure 12D:
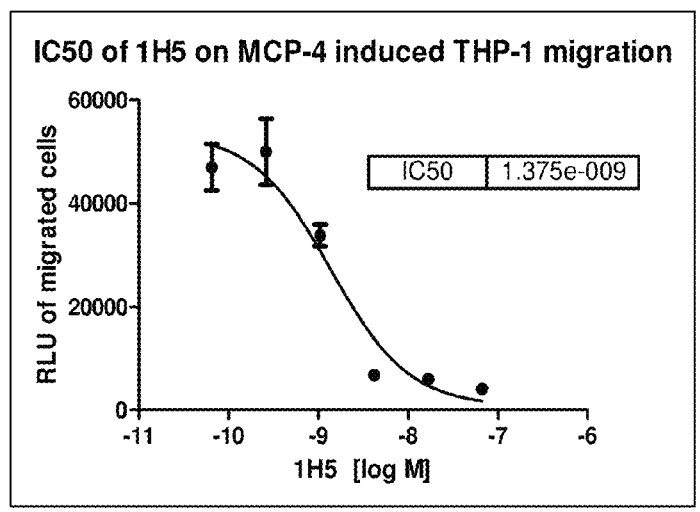
Figure 12E:
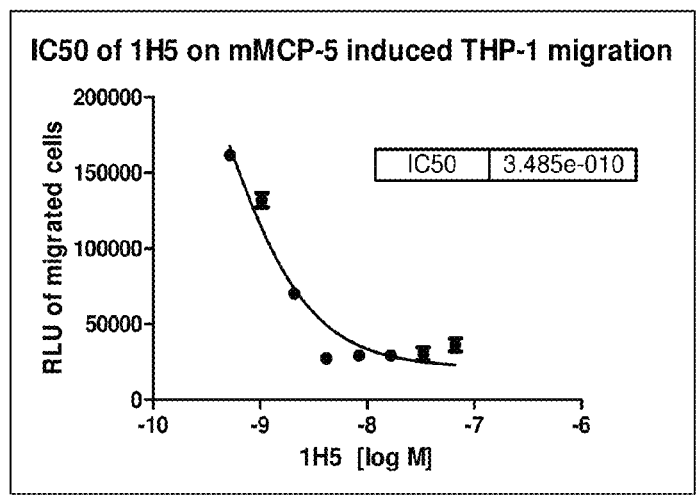

Results: $IC_{50}$ of 1G11 against MCP-1 (3 nM) was 79 pM (FIG. 10A) and against MCP-5 (6 ng/ml) was 261 pM (FIG. 10B). $IC_{50}$ of 1B2 against MCP-1 (3 nM) was 87 pM (FIG. 11A) and against MCP-5 (3 nM) was 197 pM (FIG. 11B). The $IC_{50}$ of 1H5 against MCP-1 (3 nM) was 109 pM (FIG. 12A) and against MCP-5 (6 ng/ml) was 349 pM (FIG. 12B). 1H5 also demonstrated 1.9 nM $IC_{50}$ value against 30 ng/ml of MCP-2 (FIG. 2C), 2.6 nM $IC_{50}$ value against 6 ng/ml of MCP-3 (FIG. 12D) and 1.4 nM $IC_{50}$ against 200 ng/ml of MCP-4 (FIG. 12E).

Example 11

This example shows a chemotaxis assay using THP-1 (ATCC #TIB-202) cells, a human monocyte cell line. The chemotaxis assays were set up using 96-well chemotaxis chamber (ChemoTX; NeuroProbe, Gaithersburg, Md.) with 2 compartments separated by a 5-μm polycarbonate membrane. Serial diluted concentrations of mAbs were pre-incubated with THP-1 cells ($0.1 \times 10^6$ cells in 25 μl of HBSS with 0.1% BSA) at room temperature for 20 min. Ligands in HBSS with 0.1% BSA were loaded in the wells of plate in the lower chambers, whereas the pre-incubated cells with mAbs were loaded on top of the membrane. The final concentration of ligands was 3 nM MCP-1 (PROSPEC # CHM-271), 6.7 nM of MCP-2 (PeproTech #300-15), 1.1 nM of MCP-3 (PeproTech #300-17), 35 nM of MCP-4 (PeproTech #300-24) and 0.65 nM of MCP-5 (PeproTech #250-04). After 2 h incubation at 37° C., 5% $CO_2$, non-migrated cells remaining on the upper side of the membrane were blotted by filter paper and the membrane was detached from plate in lower chamber. Migrated cells in each well of the plate in lower chamber were counted with Cedex XS cell counter (Innovatis, Roche) or transferred to an opaque white 96 well plate and treated with CellTiter GLo (Cat#G7571, Promega) for 10 min at room temperature. Luminescent signals generated by CellTiter Glo were detected by a fluorescent plate reader (FlexStation3, Molecular Device). The $IC_{50}$ value of each mAb indicated in the table was calculated by Prism5.

Results of the $IC_{50}$ of the each mAb against corresponding ligand are indicated in Table 4. Each $IC_{50}$ value represents Mean±S.D. (n=2 or n=3) and one of two or three independent experiments which had similar results. MLN1202 (Takeda) was used as a control; it is a humanized monoclonal antibody with high specificity to CCR2 and interrupts MCP-1 binding to CCR2. Disclosed mAbs (D1, 1B2, 1G11, D1-1 and D1H1/45H8L1) are human IgG1.

TABLE 4

$IC_{50}$ [pM] of mAbs in chemotaxis assay using human THP-1 cells

|  | D1 | 1B2 | 1G11 | D1-1 | D1H1/45H8L1 | MLN1202 (Takeda) |
|---|---|---|---|---|---|---|
| MCP-1 | 170 | 90 | 80 | 130 | 280 | 310 |
| MCP-2 | 170 | 60 | 160 |  |  | 460 |
| MCP-3 | 110 | 40 | 70 | 100 |  | 1830 |
| MCP-4 | 140 | 50 | 60 |  | 80 | 840 |
| MCP-5 | 190 | 200 | 260 |  |  | 370 |

Example 12

This example illustrates a calcium assay with human THP-1 cells. THP-1 cells ($0.3 \times 10^5$ cells in 25 μl of the assay buffer HBSS plus 20 mM HEPES) were pre-incubated with serial diluted doses of mAbs for 20 min at room temperature. 25 μl of the pre-incubated cells were added to 25 μl of Calcium 4 Assay kit (Molecular Device #R8142) including 5 mM probenecid (Sigma #P8761-25G) in a Poly-D-Lysine 384-well plate (Greiner #781946). After 1 h incubation at 37° C. 5% $CO_2$ followed by 15 minutes at room temperature and a brief centrifugation for the plate, a 12.5 μl of 5× concentrated ligand was added to each well of the plate as the challenge agonist during detection on the FlexStation3. The final concentration of ligands used in the assay was 2.5 nM of MCP-1 (PROSPEC # CHM-271), 22 nM of MCP-3 (PeproTech #300-17) and 0.43 nM of MCP-5 (PeproTech #250-04). $IC_{50}$ value of each mAb indicated in Table 5 was calculated by Prism5.

The results in Table 5 show the $IC_{50}$ of the each mAb against the corresponding ligand. Each $IC_{50}$ value represents Mean±S.D. (n=2) and one of two independent experiments which had similar results.

TABLE 5

$IC_{50}$ [pM] of mAbs in calcium flux assay using human THP-1 cells

|  | D1 | 1B2 | 1G11 | D1H1/45H8L1 | MLN1202 (Takeda) |
|---|---|---|---|---|---|
| MCP-1 | 180 | 920 | 750 | 370 | 250 |
| MCP-3 | 190 | 290 | 250 | 190 | 110 |
| MCP-5 | 280 | 890 | 560 | 270 | 180 |

Example 13

This example illustrates a chemotaxis assay with mouse WEHI cells. WEHI-274.1 (ATCC, CRL-1679), a mouse monocyte cell line was used in the chemotaxis assays. The chemotaxis assays were set up using 96-well chemotaxis chamber (ChemoTX; NeuroProbe, Gaithersburg, Md.) with 2 compartments separated by 8-1 µm polycarbonate membrane. Assay buffer used for chemotaxis was RPMI and HBSS at 1:1 ratio in volume plus 0.1% BSA. Serial diluted mAbs were pre-incubated with WEHI at $0.1\times10^6$ cells in 25 µl of the assay buffer for 20 min at room temperature. 0.7 nM of mouse MCP-1 (R&D, 479-JE) was loaded in the wells of plate in the lower chamber, whereas the pre-incubated cells with mAbs were loaded on top of membrane. After 2 h incubation at 37° C., 5% $CO_2$, migrated cells in the lower chamber were transferred to an opaque white 96 well plate and incubated with CellTiter GLo (Cat#G7571, Promega) for 10 min at room temperature. Luminescent signals generated from the cells in each well were detected by a fluorescent plate reader (FlexStation3, Molecular Device). The $IC_{50}$ value of each mAb indicated in Table 6 was calculated by Prism5.

The results in Table 6 show the $IC_{50}$ of each mAb against MCP-1. Each $IC_{50}$ value represents Mean±S.D. (n=2) and one of two independent experiments which had similar results. D1, D1-1 and D1H1/45H8L1 demonstrated $IC_{50}$ value 62 pM, 35 pM and 12 pM respectively.

TABLE 6

EC50 [pM] of mAbs in chemotaxis assay using mouse WEHI cells

|  | D1 | D1-1 | D1H1/45H8L1 |
|---|---|---|---|
| MCP-1 | 62 | 35 | 12 |

Example 14

In this example, CHO-CCR2 cells were lifted from culture flasks using non-enzymatic Cell Dissociation Buffer—PBS based (Life Technologies #13151-014). Cells were resuspended in FACS Buffer (2% Fetal Bovine Serum in PBS) with sodium azide at $1\times10^6$ cells/ml and 800 were aliquoted into a tube for each antibody. Antibody was added to a final concentration of 5 µg/ml and incubated at room temperature for 1 h. The samples were then placed on ice and a 105 aliquot at various time points was added to 190 µl FACS buffer in a 96-well plate and centrifuged for 3 min. Supernatant was discarded, the cells were resuspended in 105 µl of FACS buffer, aliquoted (50 µl) in duplicates into another 96-well plate containing 150 µl FACS buffer and incubated at room temperature. After all of the time points were collected, the plate was centrifuged for 3 min, supernatant discarded and the cells were resuspended in 50 µl goat anti-human IgG (γ-chain specific)-PE conjugated secondary antibody (Southern Biotech #2040-09) diluted 1:500 in FACS Buffer. Cells were further incubated for 30 min at 4° C. and then washed 1× with FACS Buffer. The cells were resuspended in a final volume of 30 µl FACS Buffer and analyzed using the Intellicyt Flow Cytometer. The off-rate of various IgG1 clones are shown in FIG. 13.

Example 15

In this example, CHO-CCR2 cells were lifted from culture flasks using non-enzymatic Cell Dissociation Buffer—PBS based (Life Technologies #13151-014). Cells were resuspended in FACS Buffer (2% Fetal Bovine Serum in PBS) at $1\times10^6$ cells/ml and 50 µl ($1\times10^5$ cells) were aliquoted into the wells of a 96-well plate. Antibody was added at one or more concentrations (typically 5, 10 and/or 20 µg/ml). Plates were incubated for 1 hr at 4° C., and then washed 1× with FACS Buffer. Cells were resuspended in 50 µl goat anti-human IgG (γ-chain specific)-PE conjugated secondary antibody (Southern Biotech #2040-09) diluted 1:500 in FACS Buffer. Cells were further incubated for 30 min at 4° C. and then washed 1× with FACS Buffer. The cells were resuspended in a final volume of 30 µl FACS Buffer and analyzed using the Intellicyt Flow Cytometer. The results of antibody binding to the cells are shown in the Table 7.

TABLE 7

| Antibody | Binding to CHO-huCCR2 |
|---|---|
| D1-3/LO | yes |
| D1-5/LO | yes |
| D1-8/LO | yes |
| 42A6 | yes |
| 42D4 | yes |
| 42 E8 | yes |
| 42F1 | yes |
| 43F12 | yes |
| 55 E4 | yes |
| 55F5 | yes |

Sequence Listing

|  | Heavy chain variable domain region | Light chain variable domain region |
|---|---|---|
| D1 | EVQLVQSGAEVKKPGASVKVSCKASGYTFTGYH MHWVRQAPGQGLEWMGWINPNSGVTKYAQ KFQGRVTMTRDTSINTAYMELSRLRFDDTDVYY CATGGFGYWGEGTLVTVSS SEQ ID NO. 1 | LPVLTQPPSVSKGLRQTATLTCTGNSNN VGNQGAAWLQQHQGQPPKLLSYRNH NRPSGVSERFSPSRSGDTSSLTITGLQPE DEADYYCLAWDSSLRAFVFGTGTKLTVL SEQ ID NO. 2 |
| 1A2 | EVQLVQSGAEVKKPGASVKVSCKASGYTFTSYY MHWVRQAPGQGLEWMGIINPSGGSTSYAQK FQGRVTMTRDTSTSTVMELSSLRSEDTAVYYC ATGSGGGTMDVWGQGTTVTVSS SEQ ID NO. 3 | LPVLTQPPSVSKGLRQTATLTCTGNSNN VGNQGAAWLQQHQGQPPKLLSYRNH NRPSGVSERFSPSRSGDTSSLTITGLQPE DEADYYCLAWDSSLRAFVFGTGTKLTVL SEQ ID NO. 2 |
| 1B11 | QVQLVESGGGVVQPGRSLRLSCAASGFTFSSYA MHWVRQAPGKGLEWVAVISYDGSNKYYADSV KGRFTISRDNSKNTLYLQMNSLKAEDTAVYYCA TAAAGPFDYWGQGTTVTVSS SEQ ID NO. 4 | LPVLTQPPSVSKGLRQTATLTCTGNSNN VGNQGAAWLQQHQGQPPKLLSYRNH NRPSGVSERFSPSRSGDTSSLTITGLQPE DEADYYCLAWDSSLRAFVFGTGTKLTVL SEQ ID NO. 2 |

| | Heavy chain variable domain region | Light chain variable domain region |
|---|---|---|
| 1G11 | EVQLVESGAEVKKPGASVKVSCKASGYIFTGYYI HWVRQAPGQGLEWMGWINPNNGVTKYAEK FQGRVTMTRDTSITTAYMDLSRLRSDDTAIYYC ATGGFEYWGQGTLVTVSS SEQ ID NO. 5 | LPVLTQPPSVSKGLRQTATLTCTGNSNN VGNQGAAWLQQHQGQPPKLLSYRNH NRPSGVSERFSPSRSGDTSSLTITGLQPE DEADYYCLAWDSSLRAFVFGTGTKLTVL SEQ ID NO. 2 |
| 1H5 | EVQLVQSGAEVKKPGASVKVSCKASGYTFTSYY MHWVRQAPGQGLEWMGIINPSGGSTSYAHK FQGRVTMTRDTSTSTVYMELSSLRSEDTAVYYC ARGGHVLRFLEWLGLEGPFDYWGQGTLVTVSS SEQ ID NO. 6 | LPVLTQPPSVSKGLRQTATLTCTGNSNN VGNQGAAWLQQHQGQPPKLLSYRNH NRPSGVSERFSPSRSGDTSSLTITGLQPE DEADYYCLAWDSSLRAFVFGTGTKLTVL SEQ ID NO. 2 |
| 1B2 | EVQLVESGAEVKKPGASVKVSCKASGYTFTYY MNWVRQAPGQGLEWMGWINPNSGGTKYA QKFQGRVTMTSDTSINTAYMELSRLRYDDTAV YYCATGGFQHWGQGTLVTVSS SEQ ID NO. 7 | LPVLTQPPSVSKGLRQTATLTCTGNSNN VGNQGAAWLQQHQGQPPKLLSYRNH NRPSGVSERFSPSRSGDTSSLTITGLQPE DEADYYCLAWDSSLRAFVFGTGTKLTVL SEQ ID NO. 2 |
| D1-1 | QVQLVQSGAEVKKPGASVKVSCKASGYTFTGY YMHWVRQAPGQGLEWMGWINPNSGVTKYA QKFQGRVTMTRDTSTSTVYMELSSLRSEDTAVY YCATGGFGYWGEGTLVTVSS SEQ ID NO. 8 | LPVLTQPPSVSKGLRQTATLTCTGNSNN VGNQGAAWLQQHQGQPPKLLSYRNH NRPSGVSERFSPSRSGDTSSLTITGLQPE DEADYYCLAWDSSLRAFVFGTGTKLTVL SEQ ID NO. 2 |
| D1-2 | QVQLVQSGAEVKKPGASVKVSCKASGYTFTGY HMHWVRQAPGQGLEWMGIINPSGGSTSYAQ KFQGRVTMTRDTSTSTVYMELSSLRSEDTAVYY CATGGFGYWGEGTLVTVSS SEQ ID NO. 9 | LPVLTQPPSVSKGLRQTATLTCTGNSNN VGNQGAAWLQQHQGQPPKLLSYRNH NRPSGVSERFSPSRSGDTSSLTITGLQPE DEADYYCLAWDSSLRAFVFGTGTKLTVL SEQ ID NO. 2 |
| D1-3 | QVQLVQSGAEVKKPGASVKVSCKASGYTFTGY HMHWVRQAPGQGLEWMGWINPNSGVTKYA QKFQGRVTMTRDTSTSTVYMELSSLRSEDTAVY YCATGSGGGTMDVWGEGTLVTVSS SEQ ID NO. 10 | LPVLTQPPSVSKGLRQTATLTCTGNSNN VGNQGAAWLQQHQGQPPKLLSYRNH NRPSGVSERFSPSRSGDTSSLTITGLQPE DEADYYCLAWDSSLRAFVFGTGTKLTVL SEQ ID NO. 2 |
| D1-4 | QVQLVQSGAEVKKPGASVKVSCKASGYTFTGY YMHWVRQAPGQGLEWMGIINPSGGSTSYAQ KFQGRVTMTRDTSTSTVYMELSSLRSEDTAVYY CATGGFGYWGEGTLVTVSS SEQ ID NO. 11 | LPVLTQPPSVSKGLRQTATLTCTGNSNN VGNQGAAWLQQHQGQPPKLLSYRNH NRPSGVSERFSPSRSGDTSSLTITGLQPE DEADYYCLAWDSSLRAFVFGTGTKLTVL SEQ ID NO. 2 |
| D1-5 | QVQLVQSGAEVKKPGASVKVSCKASGYTFTGY HMHWVRQAPGQGLEWMGWINPNGGVTSY AQKFQGRVTMTRDTSTSTVYMELSSLRSEDTA VYYCATGGFGYWGEGTLVTVSS SEQ ID NO. 12 | LPVLTQPPSVSKGLRQTATLTCTGNSNN VGNQGAAWLQQHQGQPPKLLSYRNH NRPSGVSERFSPSRSGDTSSLTITGLQPE DEADYYCLAWDSSLRAFVFGTGTKLTVL SEQ ID NO. 2 |
| D1-6 | QVQLVQSGAEVKKPGASVKVSCKASGYTFTGY HMHWVRQAPGQGLEWMGIINPSSGSTKYAQ KFQGRVTMTRDTSTSTVYMELSSLRSEDTAVYY CATGGFGYWGEGTLVTVSS SEQ ID NO. 13 | LPVLTQPPSVSKGLRQTATLTCTGNSNN VGNQGAAWLQQHQGQPPKLLSYRNH NRPSGVSERFSPSRSGDTSSLTITGLQPE DEADYYCLAWDSSLRAFVFGTGTKLTVL SEQ ID NO. 2 |
| D1-7 | QVQLVQSGAEVKKPGASVKVSCKASGYTFTGY YMHWVRQAPGQGLEWMGWINPNSGVTKYA QKFQGRVTMTRDTSTSTVYMELSSLRSEDTAVY YCATGSGGGTMDVWGEGTLVTVSS SEQ ID NO. 14 | LPVLTQPPSVSKGLRQTATLTCTGNSNN VGNQGAAWLQQHQGQPPKLLSYRNH NRPSGVSERFSPSRSGDTSSLTITGLQPE DEADYYCLAWDSSLRAFVFGTGTKLTVL SEQ ID NO. 2 |
| D1-8 | QVQLVQSGAEVKKPGASVKVSCKASGYTFTGY HMHWVRQAPGQGLEWMGIINPSGGSTSYAQ KFQGRVTMTRDTSTSTVYMELSSLRSEDTAVYY CATGSGGGTMDVWGEGTLVTVSS SEQ ID NO. 15 | LPVLTQPPSVSKGLRQTATLTCTGNSNN VGNQGAAWLQQHQGQPPKLLSYRNH NRPSGVSERFSPSRSGDTSSLTITGLQPE DEADYYCLAWDSSLRAFVFGTGTKLTVL SEQ ID NO. 2 |
| D1-1A | QVQLVQSGAEVKKPGASVKVSCKASGYTFTGY YMHWVRQAPGQGLEWMGWINPNSGVTKYA QKFQGRVTMTRDTSTSTVYMELSSLRSEDTAVY YCATGGFGYWGEGTLVTVSS SEQ ID NO. 8 | QAGLTQPPSVSKGLRQTATLTCTGNSN NVGNQGAAWLQQHQGHPPKLLSYRN HNRPSGISERFSASRSGNTASLTITGLQP EDEADYYCLAWDSSLRAFVFGGGTQLT VL SEQ ID NO. 16 |
| D1-2A | QVQLVQSGAEVKKPGASVKVSCKASGYTFTGY HMHWVRQAPGQGLEWMGIINPSGGSTSYAQ | QAGLTQPPSVSKGLRQTATLTCTGNSN NVGNQGAAWLQQHQGHPPKLLSYRN |

| | Heavy chain variable domain region | Light chain variable domain region |
|---|---|---|
| | KFQGRVTMTRDTSTSTVYMELSSLRSEDTAVYY CATGGFGYWGEGTLVTVSS SEQ ID NO. 9 | HNRPSGISERFSASRSGNTASLTITGLQP EDEADYYCLAWDSSLRAFVFGGGTQLT VL SEQ ID NO. 16 |
| D1-3A | QVQLVQSGAEVKKPGASVKVSCKASGYTFTGY HMHWVRQAPGQGLEWMGWINPNSGVTKYA QKFQGRVTMTRDTSTSTVYMELSSLRSEDTAVY YCATGSGGGTMDVWGEGTLVTVSS SEQ ID NO. 10 | QAGLTQPPSVSKGLRQTATLTCTGNSN NVGNQGAAWLQQHQGHPPKLLSYRN HNRPSGISERFSASRSGNTASLTITGLQP EDEADYYCLAWDSSLRAFVFGGGTQLT VL SEQ ID NO. 16 |
| D1-4A | QVQLVQSGAEVKKPGASVKVSCKASGYTFTGY YMHWVRQAPGQGLEWMGIINPSGGSTSYAQ KFQGRVTMTRDTSTSTVYMELSSLRSEDTAVYY CATGGFGYWGEGTLVTVSS SEQ ID NO. 11 | QAGLTQPPSVSKGLRQTATLTCTGNSN NVGNQGAAWLQQHQGHPPKLLSYRN HNRPSGISERFSASRSGNTASLTITGLQP EDEADYYCLAWDSSLRAFVFGGGTQLT VL SEQ ID NO. 16 |
| D1-5A | QVQLVQSGAEVKKPGASVKVSCKASGYTFTGY HMHWVRQAPGQGLEWMGWINPNGGVTSY AQKFQGRVTMTRDTSTSTVYMELSSLRSEDTA VYYCATGGFGYWGEGTLVTVSS SEQ ID NO. 12 | QAGLTQPPSVSKGLRQTATLTCTGNSN NVGNQGAAWLQQHQGHPPKLLSYRN HNRPSGISERFSASRSGNTASLTITGLQP EDEADYYCLAWDSSLRAFVFGGGTQLT VL SEQ ID NO. 16 |
| D1-6A | QVQLVQSGAEVKKPGASVKVSCKASGYTFTGY HMHWVRQAPGQGLEWMGIINPSSGSTKYAQ KFQGRVTMTRDTSTSTVYMELSSLRSEDTAVYY CATGGFGYWGEGTLVTVSS SEQ ID NO. 13 | QAGLTQPPSVSKGLRQTATLTCTGNSN NVGNQGAAWLQQHQGHPPKLLSYRN HNRPSGISERFSASRSGNTASLTITGLQP EDEADYYCLAWDSSLRAFVFGGGTQLT VL SEQ ID NO. 16 |
| D1-7A | QVQLVQSGAEVKKPGASVKVSCKASGYTFTGY YMHWVRQAPGQGLEWMGWINPNSGVTKYA QKFQGRVTMTRDTSTSTVYMELSSLRSEDTAVY YCATGSGGGTMDVWGEGTLVTVSS SEQ ID NO. 14 | QAGLTQPPSVSKGLRQTATLTCTGNSN NVGNQGAAWLQQHQGHPPKLLSYRN HNRPSGISERFSASRSGNTASLTITGLQP EDEADYYCLAWDSSLRAFVFGGGTQLT VL SEQ ID NO. 16 |
| D1-8A | QVQLVQSGAEVKKPGASVKVSCKASGYTFTGY HMHWVRQAPGQGLEWMGIINPSGGSTSYAQ KFQGRVTMTRDTSTSTVYMELSSLRSEDTAVYY CATGSGGGTMDVWGEGTLVTVSS SEQ ID NO. 15 | QAGLTQPPSVSKGLRQTATLTCTGNSN NVGNQGAAWLQQHQGHPPKLLSYRN HNRPSGISERFSASRSGNTASLTITGLQP EDEADYYCLAWDSSLRAFVFGGGTQLT VL SEQ ID NO. 16 |
| D1-1B | QVQLVQSGAEVKKPGASVKVSCKASGYTFTGY YMHWVRQAPGQGLEWMGWINPNSGVTKYA QKFQGRVTMTRDTSTSTVYMELSSLRSEDTAVY YCATGGFGYWGEGTLVTVSS SEQ ID NO. 8 | QAVLTQPPSVSKGLRQTATLTCTGNSN NVGNQGAAWLQQHQGQPPKLLSYRN HNRPSGVSERFSPSRSGDTSSLTITGLQP EDEADYYCLAWDSSLRAFVFGTGTKLTV L SEQ ID NO. 32 |
| D1-2B | QVQLVQSGAEVKKPGASVKVSCKASGYTFTGY HMHWVRQAPGQGLEWMGIINPSGGSTSYAQ KFQGRVTMTRDTSTSTVYMELSSLRSEDTAVYY CATGGFGYWGEGTLVTVSS SEQ ID NO. 9 | QAVLTQPPSVSKGLRQTATLTCTGNSN NVGNQGAAWLQQHQGQPPKLLSYRN HNRPSGVSERFSPSRSGDTSSLTITGLQP EDEADYYCLAWDSSLRAFVFGTGTKLTV L SEQ ID NO. 32 |
| D1-3B | QVQLVQSGAEVKKPGASVKVSCKASGYTFTGY HMHWVRQAPGQGLEWMGWINPNSGVTKYA QKFQGRVTMTRDTSTSTVYMELSSLRSEDTAVY YCATGSGGGTMDVWGEGTLVTVSS SEQ ID NO. 10 | QAVLTQPPSVSKGLRQTATLTCTGNSN NVGNQGAAWLQQHQGQPPKLLSYRN HNRPSGVSERFSPSRSGDTSSLTITGLQP EDEADYYCLAWDSSLRAFVFGTGTKLTV L SEQ ID NO. 32 |
| D1-4B | QVQLVQSGAEVKKPGASVKVSCKASGYTFTGY YMHWVRQAPGQGLEWMGIINPSGGSTSYAQ KFQGRVTMTRDTSTSTVYMELSSLRSEDTAVYY CATGGFGYWGEGTLVTVSS SEQ ID NO. 11 | QAVLTQPPSVSKGLRQTATLTCTGNSN NVGNQGAAWLQQHQGQPPKLLSYRN HNRPSGVSERFSPSRSGDTSSLTITGLQP EDEADYYCLAWDSSLRAFVFGTGTKLTV L SEQ ID NO. 32 |
| D1-5B | QVQLVQSGAEVKKPGASVKVSCKASGYTFTGY HMHWVRQAPGQGLEWMGWINPNGGVTSY AQKFQGRVTMTRDTSTSTVYMELSSLRSEDTA VYYCATGGFGYWGEGTLVTVSS SEQ ID NO. 12 | QAVLTQPPSVSKGLRQTATLTCTGNSN NVGNQGAAWLQQHQGQPPKLLSYRN HNRPSGVSERFSPSRSGDTSSLTITGLQP EDEADYYCLAWDSSLRAFVFGTGTKLTV L SEQ ID NO. 32 |
| D1-6B | QVQLVQSGAEVKKPGASVKVSCKASGYTFTGY HMHWVRQAPGQGLEWMGIINPSSGSTKYAQ KFQGRVTMTRDTSTSTVYMELSSLRSEDTAVYY CATGGFGYWGEGTLVTVSS SEQ ID NO. 13 | QAVLTQPPSVSKGLRQTATLTCTGNSN NVGNQGAAWLQQHQGQPPKLLSYRN HNRPSGVSERFSPSRSGDTSSLTITGLQP EDEADYYCLAWDSSLRAFVFGTGTKLTV L SEQ ID NO. 32 |

-continued

Sequence Listing

| | Heavy chain variable domain region | Light chain variable domain region |
|---|---|---|
| D1-7B | QVQLVQSGAEVKKPGASVKVSCKASGYTFTGY YMHWVRQAPGQGLEWMGWINPNSGVTKYA QKFQGRVTMTRDTSTSTVYMELSSLRSEDTAVY YCATGSGGGTMDVWGEGTLVTVSS SEQ ID NO. 14 | QAVLTQPPSVSKGLRQTATLTCTGNSN NVGNQGAAWLQQHQGQPPKLLSYRN HNRPSGVSERFSPSRSGDTSSLTITGLQP EDEADYYCLAWDSSLRAFVFGTGTKLTV L SEQ ID NO. 32 |
| D1-8B | QVQLVQSGAEVKKPGASVKVSCKASGYTFTGY HMHWVRQAPGQGLEWMGIINPSGGSTSYAQ KFQGRVTMTRDTSTSTVYMELSSLRSEDTAVYY CATGSGGGTMDVWGEGTLVTVSS SEQ ID NO. 15 | QAVLTQPPSVSKGLRQTATLTCTGNSN NVGNQGAAWLQQHQGQPPKLLSYRN HNRPSGVSERFSPSRSGDTSSLTITGLQP EDEADYYCLAWDSSLRAFVFGTGTKLTV L SEQ ID NO. 32 |
| 42A0 | QVQLQQSGPGLVKPSQTLSLTCVISGDSVSSGS TAWNWIRQSPSRGLEWLGRTFYRSKWYNDYA ESVKSRITISADTSENQLSLHLNSVTAEDTAVYYC ARGSRGSGYDYWGQGTLVTVSS SEQ ID NO. 17 | QTVVTQPPSASGTPGQRVTISCSGSSSNI GSSNVNWYQQFPGKAPQLLIYTGDQRP SGVPDRFSGSKSGTSASLAITGLQPEDEA DYYCSAWDTNLSAWVFGGGTKLTVL SEQ ID NO. 18 |
| 42D4 | EVQLVESGGELVQPGGSLRLSCAASGFTFSSFA MHWVRQAPGKGLEYVSGISSNGGSTYYANSV KGRFTISRDNSKNTLSLQMGSLRPEDMAVYYC ARGGMDVWGQGTTVTVSS SEQ ID NO. 19 | QSVLTQPPSVSKGLRQTATLTCTGNSNN VGNQGAAWLQQHQGHPPKLLSYRNH NRPSGISERFSASTSGSTASLTIVGLQPED EADYYCLAWDTSLHAFVFGSGTKLTVL SEQ ID NO. 20 |
| 42E8 | QVQLVQSGAEVKKPGASVKVSCKAYGYTFTNY YLHWVRQAPGQGLEWMGIINPSGGNTNYAQ KFKGRVTMTRDTSTNTVYMEMSSLRSEDTAVY YCARGGGGAFDIWGQGTMVTVSS SEQ ID NO. 21 | DIVMTQSPLSSPVTLGQPASISCRSSQSL VHSDGNTYLSWLQQRPGQPPRLLIYRTS KRFSGVPDRFSGSGSGTDFTLKISRVEVE DVGVYYCMQATQFPRTFGQGTKVEIK SEQ ID NO. 22 |
| 42F1 | QLVESGGDLVQPGGFLRLSCAASGFTFSSYSMN WVRQAPGKGLEWVANIKQDGSEKYYVDSVKG RFTISRDNAKNSLYLQMNSLRAEDTAVYYCARA PGSYWGQGTLVTVSS SEQ ID NO. 23 | QSVVTQPPSVSAAPGQKVTIACSGSSSN IGTHYTSWYQQLPGAAPKLLIYGSSKRPS GIPDRFSGSKSGTSATLGITGLQTGDEAE YYCATWDSRLNVGVFGGGTKLTVL SEQ ID NO. 24 |
| 42G7 | QVQLVQSGAEVKKPGASVKVSCKASGYTFSSYY MHWVRQAPGQGLEWMGIINPSGGNTSYAQK FQGRVTMTRDTSTSTVYMELSSLRSEDTAVYYC ARGGYQLPHGRARAFDMWGQGTMVTVSS SEQ ID NO. 25 | AIRMTQSPLSLPVTLGQPASISCTSSQSL VYRDGTTYLNWFQQRPGQSPRRLIYKV SNRDSGVPDRFTGSGSGTTFTLTISRVEA EDVGIYYCMQGTHWPLTFGQGTKVEIK SEQ ID NO. 26 |
| 43D12 | EVQLVESGGGLVQPGGSLRLSCVASGFTFSDY WMSWVRQAPGKGLEWVANIKKDGSVNYYVD SVKGRFTISRDNAKNSLYLQMNSLRAEDTAVYY CTRFDYWGQGTLVTVSS SEQ ID NO. 27 | QAGLTQPPSVSKGLRQTATLTCTGNSN NVGNQGAAWLQQHQGHPPKLLFYRN NNRASGISERLSASRSGNTASLTITGLQP EDEADYYCLTWDSSLSVVVFGGGTKLTV L SEQ ID NO. 28 |
| 43F12 | QVQLVESGGGLVQPGRSLRLSCAASGFSFDDY AMHWVRQAPGKGLEWLSIYSGGKTYYADSV KGRFTISRDSSKNTLYLQMNTLRPEDTAVYYCA RNIGNWGQGTLVTVSS SEQ ID NO. 29 | QSVLTQPPSVSKDLRQTATLTCTGNSNN VGNQGAAWLQQHQGHPPKFLSDRYN NRPSGISERFSASRSGNTASLTITGVQPE DEADYYCSAWDTSLNALVFGGGTKLTV L SEQ ID NO. 30 |
| 45H8 | EVQLVQSGAEVKKPGASVKVSCKASGYTFTGYH MHWVRQAPGQGLEWMGWINPNSGVTKYAQ KFQGRVTMTRDTSINTAYMELSRLRFDDTDVYY CATGGFGYWGEGTLVTVSS SEQ ID NO. 31 | QAVLTQPPSVSKGLRQTATLTCTGNSN NVGNQGAAWLQQHQGQPPKLLSYRN HNRPSGVSERFSPSRSGDTSSLTITGLQP EDEADYYCLAWDSSLRAFVFGTGTKLTV L SEQ ID NO. 32 |
| 44A4 | QVQLVQSGAEVKKPGASVKVSCKASGYTFTNY YMHWVRQAPGQGLEWMGIINPSGSITTFAQN FQGRVTMTRDTSTSTLYMELSSLRSEDTAVYYC AREFRQDYYNGMDVWGQGTTVTVSS SEQ ID NO. 33 | QSVLTQPASVSGSPGQSITISCTGTSSDV GGYNYVSWYQQHPGKAPKLMIYDVSN RPSGVSNRFSGSKSGNTASLTISGLQAE DEADYYCSSYTSSIPLVFGGGTKLTVL SEQ ID NO. 34 |
| 45D7 | EVQLVESGGGVVRPGGSLRLSCAASGFTFGDY GMSWVRQAPGKGLEWVSGINWNGGSTGYA DSVKGRFTISRDNAKNSLYLQMSSLRADDTAVY YCARVTAGYWGQGTLVTVSS SEQ ID NO. 35 | QAGLTQPPSVSKDLRQTATLTCTGNSN NVGNQGAAWLQQHQGHPPKLLSYRN NNRPSGISERLSASRSGDTASLTITGLQP EDEADYYCSAWDTSLSAWVFGGGTKLT VL SEQ ID NO. 36 |
| 54A9 | QVQLVESGAEVKKPGASVKVSCKASGYTFSSHY MHWVRQAPGQGLEWMGIINPSGGSTIYAQKF | LPVLTQPASVSGSPGQSITISCTGTSSDV GGYNYVSWYQQHPGKAPKLMIYDVSN |

| | Heavy chain variable domain region | Light chain variable domain region |
|---|---|---|
| | QGRVTINADESTSTAYMELSSLGSDDTAVYYCA RAAGGAVAGHGARFDYWGQGTLVTVSS SEQ ID NO. 37 | RPSGVSNRFSGSKSGNTASLTISGLQAE DEADYYCSSYRRSSTLVFGGGTKLTVL SEQ ID NO. 38 |
| 54C1 | QITLKESGAEVKKPGASVKVSCKASGYTFTSYYM HWVRQAPGQGLEWMGIINPSGGSTSYAQKFQ GRVTMTRDTSTSTAYMELSSLRSEDTAMYYCA KNHPTATLDYWGQGTLVTVSS SEQ ID NO. 39 | QSVLTQPASVSGSPGQSITISCTGTSSDV GGYNYVSWYQQHPGKAPKLMIYDVSK RPSGVSNRFSGSKSANTASLTIFGLQAED EGDYYCSSYRSIRTVLFGGGTKLTVL SEQ ID NO. 40 |
| 55E4 | EVQLVESGAEVKKPGASVKVSCKASGYTFTSYY MHWVRQAPGRGLEWMGIINPSSGSTSYAQKF QGRVTMTRDTSTSTVYMELSSLRSEDTAVYYCA RGQGTAIRAFDIWGQGTMVTVSS SEQ ID NO. 41 | DIVMTQTPLSSPVTLGQPAAISCRSSQSL VNSDGNTYLSWLQQRPGQPPRVLINKV SNRLSGVPDRFSGSGAGTDFTLKISRVEA EDVGVYYCMQATEFPWTFGQGTRLEIK SEQ ID NO. 42 |
| 55F5 | EVQLVQSGAEVKKPGASVKVSCKASGYTFTSYY MHWVRQAPGRGLEWMGIINPSSGSTSYAQKF QGRVTMTRDTSTSTVYMELSSLRSEDTAVYYCA RGQGTAIRAFDIWGQGTMVTVSS SEQ ID NO. 43 | DVVMTQSPLSSPVTLGQPASISCKSSQT LVHNDGNSYLSWLHQRPGQPPRLLIYK VSNRFSGVPDRFSGSGAGTDFTLRIGRV EAEDVGVYYCMQATQFPYTFGQGTKLE IK SEQ ID NO. 44 |

We claim:

1. A recombinant fully human antibody of an IgG class that binds to a CC-Chemokine Receptor 2 (CCR2) epitope, wherein the antibody has a heavy chain variable domain sequence that is at least 95% identical to an amino acid sequence selected from the group consisting of SEQ ID NO. 1, SEQ ID NO. 25, and SEQ ID NO. 27, and has a light chain variable domain sequence that is at least 95% identical to an amino acid sequence selected from the group consisting of SEQ ID NO. 2, SEQ ID NO. 26, and SEQ ID NO. 28, and wherein the antibody has a heavy chain/light chain variable domain sequence pairing that is at least 95% identical to the amino acid sequences selected from the group consisting of SEQ ID NO. 1/SEQ ID NO. 2 SEQ ID NO. 25/SEQ ID NO. 26, and SEQ ID NO. 27/SEQ ID NO. 28.

2. A Fab fully human antibody fragment that binds to a CCR2 epitope, having a heavy chain variable domain and a light chain variable domain, wherein the antibody fragment has a heavy chain variable domain sequence that is at least 95% identical to an amino acid sequence selected from the group consisting of SEQ ID NO. 1, SEQ ID NO. 25, and SEQ ID NO. 27, and has a light chain variable domain sequence that is at least 95% identical to an amino acid sequence selected from the group consisting of SEQ ID NO. 2, SEQ ID NO. 26, and SEQ ID NO. 28, and wherein the antibody has a heavy chain/light chain variable domain sequence pairing that is at least 95% identical to an amino acid sequence pairing selected from the group consisting of SEQ ID NO. 1/SEQ ID NO. 2, SEQ ID NO. 25/SEQ ID NO. 26, and SEQ ID NO. 27/SEQ ID NO. 28.

3. A single chain human antibody that binds to a CCR2 epitope, having a heavy chain variable domain, a light chain variable domain, and a peptide linker connecting the heavy chain and light chain variable domains, wherein the heavy chain variable domain has a sequence that is at least 95% identical to an amino acid sequence selected from the group consisting of SEQ ID NO. 1, SEQ ID NO. 25, and SEQ ID NO. 27, and the light chain variable domain has a sequence that is at least 95% identical to an amino acid sequence selected from the group consisting of SEQ ID NO. 2, SEQ ID NO. 26, and SEQ ID NO. 28, and wherein the single chain antibody has a heavy chain/light chain variable domain sequence pairing that is at least 95% identical to an amino acid sequence pairing selected from the group consisting of SEQ ID NO. 1/SEQ ID NO. 2, SEQ ID NO. 25/SEQ ID NO. 26, and SEQ ID NO. 27/SEQ ID NO. 28.

4. An anti-CC-Chemokine Receptor 2 (anti-CCR2) recombinant antibody comprising a heavy chain variable domain having an amino acid sequence selected from the group consisting of SEQ ID NO. 1, SEQ ID NO. 25, SEQ ID NO. 27, SEQ ID NO. 29, and SEQ ID NO. 37, and comprising a light chain variable domain having an amino acid sequence selected from the group consisting of SEQ ID NO. 2, SEQ ID NO. 16, SEQ ID NO. 26, SEQ ID NO. 28, and SEQ ID NO. 32, wherein the antibody is an IgG.

5. The anti-CCR2 antibody of claim 4, wherein the heavy chain variable domain has an amino acid sequence as set forth in SEQ ID NO: 1, and the light chain variable domain has an amino acid sequence as set forth in SEQ ID NO: 2.

6. The anti-CCR2 antibody of claim 4, wherein the heavy chain variable domain has an amino acid sequence as set forth in SEQ ID NO: 25 and the light chain variable domain has an amino acid sequence as set forth in SEQ ID NO: 26.

7. The anti-CCR2 antibody of claim 4, wherein the heavy chain variable domain has an amino acid sequence as set forth in SEQ ID NO: 27, and the light chain variable domain has an amino acid sequence as set forth in SEQ ID NO: 28.

8. An anti-CC-Chemokine Receptor 2 (anti-CCR2) recombinant single chain antibody or an anti-CCR2 recombinant Fab fully human antibody fragment, comprising a heavy chain variable domain having an amino acid sequence selected from the group consisting of SEQ ID NO. 1, SEQ ID NO. 25, SEQ ID NO. 27, SEQ ID NO. 29, and SEQ ID NO. 37, and comprising a light chain variable domain having an amino acid sequence selected from the group consisting of SEQ ID NO. 2, SEQ ID NO. 16, SEQ ID NO. 26, SEQ ID NO. 28, and SEQ ID NO. 32.

* * * * *

SEQUENCE LISTING

<160> NUMBER OF SEQ ID NOS: 44

<210> SEQ ID NO 1
<211> LENGTH: 114
<212> TYPE: PRT
<213> ORGANISM: Homo sapians

<400> SEQUENCE: 1

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

His Met His Trp Val Arg Gln Ala Pro Gly Gln Gly Leu Glu Trp Met
        35                  40                  45

Gly Trp Ile Asn Pro Asn Ser Gly Val Thr Lys Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Phe Asp Asp Thr Asp Val Tyr Tyr Cys
                85                  90                  95

Ala Thr Gly Gly Phe Gly Tyr Trp Gly Glu Gly Thr Leu Val Thr Val
            100                 105                 110

Ser Ser
```

<210> SEQ ID NO 2
<211> LENGTH: 110
<212> TYPE: PRT
<213> ORGANISM: Homo sapians

<400> SEQUENCE: 2

```
Leu Pro Val Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly Gln Pro Pro Lys Leu Leu
```

```
                    35                  40                  45
Ser Tyr Arg Asn His Asn Arg Pro Ser Gly Val Ser Glu Arg Phe Ser
 50                  55                  60

Pro Ser Arg Ser Gly Asp Thr Ser Ser Leu Thr Ile Thr Gly Leu Gln
 65                  70                  75                  80

Pro Glu Asp Glu Ala Asp Tyr Tyr Cys Leu Ala Trp Asp Ser Ser Leu
                 85                  90                  95

Arg Ala Phe Val Phe Gly Thr Gly Thr Lys Leu Thr Val Leu
            100                 105                 110

<210> SEQ ID NO 3
<211> LENGTH: 118
<212> TYPE: PRT
<213> ORGANISM: Homo sapians

<400> SEQUENCE: 3

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Tyr Met His Trp Val Arg Gln Ala Pro Gly Gln Gly Leu Glu Trp Met
             35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Thr Gly Ser Gly Gly Gly Met Asp Val Trp Gly Gln Gly Thr
            100                 105                 110

Thr Val Thr Val Ser Ser
        115

<210> SEQ ID NO 4
<211> LENGTH: 117
<212> TYPE: PRT
<213> ORGANISM: Homo sapians

<400> SEQUENCE: 4

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Ala Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Lys Ala Glu Asp Thr Ala Val Tyr Tyr Cys
                 85                  90                  95

Ala Thr Ala Ala Ala Gly Pro Phe Asp Tyr Trp Gly Gln Gly Thr Thr
            100                 105                 110

Val Thr Val Ser Ser
        115
```

```
<210> SEQ ID NO 5
<211> LENGTH: 114
<212> TYPE: PRT
<213> ORGANISM: Homo sapians

<400> SEQUENCE: 5
```

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Ile Phe Thr Gly Tyr
            20                  25                  30

Tyr Ile His Trp Val Arg Gln Ala Pro Gly Gln Gly Leu Glu Trp Met
        35                  40                  45

Gly Trp Ile Asn Pro Asn Asn Gly Val Thr Lys Tyr Ala Glu Lys Phe
    50                  55                  60

Gln Gly Arg Val Thr Met Thr Arg Asp Thr Ser Ile Thr Thr Ala Tyr
65                  70                  75                  80

Met Asp Leu Ser Arg Leu Arg Ser Asp Asp Thr Ala Ile Tyr Tyr Cys
                85                  90                  95

Ala Thr Gly Gly Phe Glu Tyr Trp Gly Gln Gly Thr Leu Val Thr Val
            100                 105                 110

Ser Ser

```
<210> SEQ ID NO 6
<211> LENGTH: 128
<212> TYPE: PRT
<213> ORGANISM: Homo sapians

<400> SEQUENCE: 6
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala His Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly His Val Leu Arg Phe Leu Glu Trp Leu Gly Leu Glu
            100                 105                 110

Gly Pro Phe Asp Tyr Trp Gly Gln Gly Thr Leu Val Thr Val Ser Ser
        115                 120                 125

```
<210> SEQ ID NO 7
<211> LENGTH: 114
<212> TYPE: PRT
<213> ORGANISM: Homo sapians

<400> SEQUENCE: 7
```

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Asn Trp Val Arg Gln Ala Pro Gly Gln Gly Leu Glu Trp Met
        35                  40                  45

```
Gly Trp Ile Asn Pro Asn Ser Gly Gly Thr Lys Tyr Ala Gln Lys Phe
    50                  55                  60

Gln Gly Arg Val Thr Met Thr Ser Asp Thr Ser Ile Asn Thr Ala Tyr
65                  70                  75                  80

Met Glu Leu Ser Arg Leu Arg Tyr Asp Asp Thr Ala Val Tyr Tyr Cys
                85                  90                  95

Ala Thr Gly Gly Phe Gln His Trp Gly Gln Gly Thr Leu Val Thr Val
            100                 105                 110

Ser Ser
```

<210> SEQ ID NO 8
<211> LENGTH: 114
<212> TYPE: PRT
<213> ORGANISM: Homo sapians

<400> SEQUENCE: 8

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Val Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Gly Gly Phe Gly Tyr Trp Gly Glu Gly Thr Leu Val Thr Val
            100                 105                 110

Ser Ser
```

<210> SEQ ID NO 9
<211> LENGTH: 114
<212> TYPE: PRT
<213> ORGANISM: Homo sapians

<400> SEQUENCE: 9

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

His Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Gly Gly Phe Gly Tyr Trp Gly Glu Gly Thr Leu Val Thr Val
            100                 105                 110

Ser Ser
```

<210> SEQ ID NO 10
<211> LENGTH: 118

<212> TYPE: PRT
<213> ORGANISM: Homo sapians

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

His Met His Trp Val Arg Gln Ala Pro Gly Gln Gly Leu Glu Trp Met
        35                  40                  45

Gly Trp Ile Asn Pro Asn Ser Gly Val Thr Lys Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Gly Ser Gly Gly Gly Thr Met Asp Val Trp Gly Glu Gly Thr
            100                 105                 110

Leu Val Thr Val Ser Ser
            115
```

<210> SEQ ID NO 11
<211> LENGTH: 114
<212> TYPE: PRT
<213> ORGANISM: Homo sapians

<400> SEQUENCE: 11

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Gly Gly Phe Gly Tyr Trp Gly Glu Gly Thr Leu Val Thr Val
            100                 105                 110

Ser Ser
```

<210> SEQ ID NO 12
<211> LENGTH: 114
<212> TYPE: PRT
<213> ORGANISM: Homo sapians

<400> SEQUENCE: 12

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

His Met His Trp Val Arg Gln Ala Pro Gly Gln Gly Leu Glu Trp Met
        35                  40                  45

Gly Trp Ile Asn Pro Asn Gly Gly Val Thr Ser Tyr Ala Gln Lys Phe
    50                  55                  60
```

```
Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Gly Gly Phe Gly Tyr Trp Gly Glu Gly Thr Leu Val Thr Val
            100                 105                 110

Ser Ser
```

<210> SEQ ID NO 13
<211> LENGTH: 114
<212> TYPE: PRT
<213> ORGANISM: Homo sapians

<400> SEQUENCE: 13

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

His Met His Trp Val Arg Gln Ala Pro Gly Gln Gly Leu Glu Trp Met
            35                  40                  45

Gly Ile Ile Asn Pro Ser Ser Gly Ser Thr Lys Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Gly Gly Phe Gly Tyr Trp Gly Glu Gly Thr Leu Val Thr Val
            100                 105                 110

Ser Ser
```

<210> SEQ ID NO 14
<211> LENGTH: 118
<212> TYPE: PRT
<213> ORGANISM: Homo sapians

<400> SEQUENCE: 14

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Val Thr Lys Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Gly Ser Gly Gly Thr Met Asp Val Trp Gly Glu Gly Thr
            100                 105                 110

Leu Val Thr Val Ser Ser
        115
```

<210> SEQ ID NO 15
<211> LENGTH: 118
<212> TYPE: PRT

```
<213> ORGANISM: Homo sapians

<400> SEQUENCE: 15

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Gly Tyr
            20                  25                  30

His Met His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Gly Ser Gly Gly Gly Thr Met Asp Val Trp Gly Glu Gly Thr
            100                 105                 110

Leu Val Thr Val Ser Ser
            115

<210> SEQ ID NO 16
<211> LENGTH: 110
<212> TYPE: PRT
<213> ORGANISM: Homo sapians

<400> SEQUENCE: 16

Gln Ala Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Ser Tyr Arg Asn His Asn Arg Pro Ser Gly Ile Ser Glu Arg Phe Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Leu Ala Trp Asp Ser Ser Leu
                85                  90                  95

Arg Ala Phe Val Phe Gly Gly Gly Thr Gln Leu Thr Val Leu
            100                 105                 110

<210> SEQ ID NO 17
<211> LENGTH: 121
<212> TYPE: PRT
<213> ORGANISM: Homo sapians

<400> SEQUENCE: 17

Gln Val Gln Leu Gln Gln Ser Gly Pro Gly Leu Val Lys Pro Ser Gln
1               5                   10                  15

Thr Leu Ser Leu Thr Cys Val Ile Ser Gly Asp Ser Val Ser Ser Gly
            20                  25                  30

Ser Thr Ala Trp Asn Trp Ile Arg Gln Ser Pro Ser Arg Gly Leu Glu
        35                  40                  45

Trp Leu Gly Arg Thr Phe Tyr Arg Ser Lys Trp Tyr Asn Asp Tyr Ala
    50                  55                  60

Glu Ser Val Lys Ser Arg Ile Thr Ile Ser Ala Asp Thr Ser Glu Asn
65                  70                  75                  80
```

```
Gln Leu Ser Leu His Leu Asn Ser Val Thr Ala Glu Asp Thr Ala Val
                85                  90                  95

Tyr Tyr Cys Ala Arg Gly Ser Arg Gly Ser Gly Tyr Asp Tyr Trp Gly
            100                 105                 110

Gln Gly Thr Leu Val Thr Val Ser Ser
        115                 120

<210> SEQ ID NO 18
<211> LENGTH: 110
<212> TYPE: PRT
<213> ORGANISM: Homo sapians

<400> SEQUENCE: 18

Gln Thr Val Val Thr Gln Pro Pro Ser Ala Ser Gly Thr Pro Gly Gln
1               5                   10                  15

Arg Val Thr Ile Ser Cys Ser Gly Ser Ser Asn Ile Gly Ser Ser
            20                  25                  30

Asn Val Asn Trp Tyr Gln Gln Phe Pro Gly Lys Ala Pro Gln Leu Leu
            35                  40                  45

Ile Tyr Thr Gly Asp Gln Arg Pro Ser Gly Val Pro Asp Arg Phe Ser
        50                  55                  60

Gly Ser Lys Ser Gly Thr Ser Ala Ser Leu Ala Ile Thr Gly Leu Gln
65                  70                  75                  80

Pro Glu Asp Glu Ala Asp Tyr Tyr Cys Ser Ala Trp Asp Thr Asn Leu
                85                  90                  95

Ser Ala Trp Val Phe Gly Gly Gly Thr Lys Leu Thr Val Leu
            100                 105                 110

<210> SEQ ID NO 19
<211> LENGTH: 114
<212> TYPE: PRT
<213> ORGANISM: Homo sapians

<400> SEQUENCE: 19

Glu Val Gln Leu Val Glu Ser Gly Gly Glu Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met His Trp Val Arg Gln Ala Pro Gly Lys Gly Leu Glu Tyr Val
            35                  40                  45

Ser Gly Ile Ser Ser Asn Gly Gly Ser Thr Tyr Tyr Ala Asn Ser Val
        50                  55                  60

Lys Gly Arg Phe Thr Ile Ser Arg Asp Asn Ser Lys Asn Thr Leu Ser
65                  70                  75                  80

Leu Gln Met Gly Ser Leu Arg Pro Glu Asp Met Ala Val Tyr Tyr Cys
                85                  90                  95

Ala Arg Gly Gly Met Asp Val Trp Gly Gln Gly Thr Thr Val Thr Val
            100                 105                 110

Ser Ser

<210> SEQ ID NO 20
<211> LENGTH: 110
<212> TYPE: PRT
<213> ORGANISM: Homo sapians

<400> SEQUENCE: 20

Gln Ser Val Leu Thr Gln Pro Pro Ser Val Ser Lys Gly Leu Arg Gln
```

```
1               5                   10                  15
Thr Ala Thr Leu Thr Cys Thr Gly Asn Ser Asn Asn Val Gly Asn Gln
                20                  25                  30
Gly Ala Ala Trp Leu Gln Gln His Gln Gly His Pro Pro Lys Leu Leu
                35                  40                  45
Ser Tyr Arg Asn His Asn Arg Pro Ser Gly Ile Ser Glu Arg Phe Ser
    50                  55                  60
Ala Ser Thr Ser Gly Ser Thr Ala Ser Leu Thr Ile Val Gly Leu Gln
65                  70                  75                  80
Pro Glu Asp Glu Ala Asp Tyr Tyr Cys Leu Ala Trp Asp Thr Ser Leu
                85                  90                  95
His Ala Phe Val Phe Gly Ser Gly Thr Lys Leu Thr Val Leu
                100                 105                 110
```

<210> SEQ ID NO 21
<211> LENGTH: 117
<212> TYPE: PRT
<213> ORGANISM: Homo sapiens

<400> SEQUENCE: 21

```
Gln Val Gln Leu Val Gln Ser Gly Ala Glu Val Lys Lys Pro Gly Ala
1               5                   10                  15
Ser Val Lys Val Ser Cys Lys Ala Tyr Gly Tyr Thr Phe Thr Asn Tyr
                20                  25                  30
Tyr Leu His Trp Val Arg Gln Ala Pro Gly Gln Gly Leu Glu Trp Met
                35                  40                  45
Gly Ile Ile Asn Pro Ser Gly Gly Asn Thr Asn Tyr Ala Gln Lys Phe
                50                  55                  60
Lys Gly Arg Val Thr Met Thr Arg Asp Thr Ser Thr Asn Thr Val Tyr
65                  70                  75                  80
Met Glu Met Ser Ser Leu Arg Ser Glu Asp Thr Ala Val Tyr Tyr Cys
                85                  90                  95
Ala Arg Gly Gly Gly Ala Phe Asp Ile Trp Gly Gln Gly Thr Met
                100                 105                 110
Val Thr Val Ser Ser
        115
```

<210> SEQ ID NO 22
<211> LENGTH: 112
<212> TYPE: PRT
<213> ORGANISM: Homo sapiens

<400> SEQUENCE: 22

```
Asp Ile Val Met Thr Gln Ser Pro Leu Ser Ser Pro Val Thr Leu Gly
1               5                   10                  15
Gln Pro Ala Ser Ile Ser Cys Arg Ser Ser Gln Ser Leu Val His Ser
                20                  25                  30
Asp Gly Asn Thr Tyr Leu Ser Trp Leu Gln Gln Arg Pro Gly Gln Pro
                35                  40                  45
Pro Arg Leu Leu Ile Tyr Arg Thr Ser Lys Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Val Glu Asp Val Gly Val Tyr Tyr Cys Met Gln Ala
                85                  90                  95
Thr Gln Phe Pro Arg Thr Phe Gly Gln Gly Thr Lys Val Glu Ile Lys
```

<210> SEQ ID NO 23
<211> LENGTH: 112
<212> TYPE: PRT
<213> ORGANISM: Homo sapians

<400> SEQUENCE: 23

```
Gln Leu Val Glu Ser Gly Gly Asp Leu Val Gln Pro Gly Gly Phe Leu
  1               5                  10                  15
Arg Leu Ser Cys Ala Ala Ser Gly Phe Thr Phe Ser Ser Tyr Ser Met
             20                  25                  30
Asn Trp Val Arg Gln Ala Pro Gly Lys Gly Leu Glu Trp Val Ala Asn
         35                  40                  45
Ile Lys Gln Asp Gly Ser Glu Lys Tyr Tyr Val Asp Ser Val Lys Gly
 50                  55                  60
Arg Phe Thr Ile Ser Arg Asp Asn Ala Lys Asn Ser Leu Tyr Leu Gln
 65                  70                  75                  80
Met Asn Ser Leu Arg Ala Glu Asp Thr Ala Val Tyr Tyr Cys Ala Arg
                 85                  90                  95
Ala Pro Gly Ser Tyr Trp Gly Gln Gly Thr Leu Val Thr Val Ser Ser
            100                 105                 110
```

<210> SEQ ID NO 24
<211> LENGTH: 110
<212> TYPE: PRT
<213> ORGANISM: Homo sapians

<400> SEQUENCE: 24

```
Gln Ser Val Val Thr Gln Pro Pro Ser Val Ser Ala Ala Pro Gly Gln
  1               5                  10                  15
Lys Val Thr Ile Ala Cys Ser Gly Ser Ser Ser Asn Ile Gly Thr His
             20                  25                  30
Tyr Thr Ser Trp Tyr Gln Gln Leu Pro Gly Ala Ala Pro Lys Leu Leu
         35                  40                  45
Ile Tyr Gly Ser Ser Lys Arg Pro Ser Gly Ile Pro Asp Arg Phe Ser
 50                  55                  60
Gly Ser Lys Ser Gly Thr Ser Ala Thr Leu Gly Ile Thr Gly Leu Gln
 65                  70                  75                  80
Thr Gly Asp Glu Ala Glu Tyr Tyr Cys Ala Thr Trp Asp Ser Arg Leu
                 85                  90                  95
Asn Val Gly Val Phe Gly Gly Gly Thr Lys Leu Thr Val Leu
            100                 105                 110
```

<210> SEQ ID NO 25
<211> LENGTH: 124
<212> TYPE: PRT
<213> ORGANISM: Homo sapians

<400> SEQUENCE: 25

```
Gln Val Gln Leu Val Gln Ser Gly Ala Glu Val Lys Lys Pro Gly Ala
  1               5                  10                  15
Ser Val Lys Val Ser Cys Lys Ala Ser Gly Tyr Thr Phe Ser Ser Tyr
             20                  25                  30
Tyr Met His Trp Val Arg Gln Ala Pro Gly Gln Gly Leu Glu Trp Met
         35                  40                  45
Gly Ile Ile Asn Pro Ser Gly Gly Asn Thr Ser Tyr Ala Gln Lys Phe
 50                  55                  60
```

```
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Gly Tyr Gln Leu Pro His Gly Arg Ala Arg Ala Phe Asp
            100                 105                 110

Met Trp Gly Gln Gly Thr Met Val Thr Val Ser Ser
        115                 120
```

<210> SEQ ID NO 26
<211> LENGTH: 111
<212> TYPE: PRT
<213> ORGANISM: Homo sapians

<400> SEQUENCE: 26

```
Ala Ile Arg Met Thr Gln Ser Pro Leu Ser Leu Pro Val Thr Leu Gly
 1               5                  10                  15

Gln Pro Ala Ser Ile Ser Cys Thr Ser Ser Gln Ser Leu Val Tyr Arg
            20                  25                  30

Asp Gly Thr Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
 50                  55                  60

Asp Arg Phe Thr Gly Ser Gly Ser Gly Thr Thr Phe Thr Leu Thr Ile
 65                  70                  75                  80

Ser Arg Val Glu Ala Glu Asp Val Gly Ile Tyr Tyr Cys Met Gln Gly
                 85                  90                  95

Thr His Trp Pro Leu Thr Phe Gly Gln Gly Thr Lys Val Glu Ile
            100                 105                 110
```

<210> SEQ ID NO 27
<211> LENGTH: 112
<212> TYPE: PRT
<213> ORGANISM: Homo sapians

<400> SEQUENCE: 27

```
Glu Val Gln Leu Val Glu Ser Gly Gly Gly Leu Val Gln Pro Gly Gly
 1               5                  10                  15

Ser Leu Arg Leu Ser Cys Val Ala Ser Gly Phe Thr Phe Ser Asp Tyr
            20                  25                  30

Trp Met Ser Trp Val Arg Gln Ala Pro Gly Lys Gly Leu Glu Trp Val
        35                  40                  45

Ala Asn Ile Lys Lys Asp Gly Ser Val Asn Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Thr Arg Phe Asp Tyr Trp Gly Gln Gly Thr Leu Val Thr Val Ser Ser
            100                 105                 110
```

<210> SEQ ID NO 28
<211> LENGTH: 110
<212> TYPE: PRT
<213> ORGANISM: Homo sapians

<400> SEQUENCE: 28

```
Gln Ala Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Phe Tyr Arg Asn Asn Asn Arg Ala Ser Gly Ile Ser Glu Arg Leu Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Leu Thr Trp Asp Ser Ser Leu
                85                  90                  95

Ser Val Val Val Phe Gly Gly Gly Thr Lys Leu Thr Val Leu
            100                 105                 110

<210> SEQ ID NO 29
<211> LENGTH: 112
<212> TYPE: PRT
<213> ORGANISM: Homo sapians

<400> SEQUENCE: 29

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Ser Phe Asp Asp Tyr
            20                  25                  30

Ala Met His Trp Val Arg Gln Ala Pro Gly Lys Gly Leu Glu Trp Val
        35                  40                  45

Ser Leu Ile Tyr Ser Gly Gly Lys Thr Tyr Tyr Ala Asp Ser Val Lys
    50                  55                  60

Gly Arg Phe Thr Ile Ser Arg Asp Ser Ser Lys Asn Thr Leu Tyr Leu
65                  70                  75                  80

Gln Met Asn Thr Leu Arg Pro Glu Asp Thr Ala Val Tyr Tyr Cys Ala
                85                  90                  95

Arg Asn Ile Gly Asn Trp Gly Gln Gly Thr Leu Val Thr Val Ser Ser
            100                 105                 110

<210> SEQ ID NO 30
<211> LENGTH: 110
<212> TYPE: PRT
<213> ORGANISM: Homo sapians

<400> SEQUENCE: 30

Gln Ser Val Leu Thr Gln Pro Pro Ser Val Ser Lys Asp Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Phe Leu
        35                  40                  45

Ser Asp Arg Tyr Asn Asn Arg Pro Ser Gly Ile Ser Glu Arg Phe Ser
    50                  55                  60

Ala Ser Arg Ser Gly Asn Thr Ala Ser Leu Thr Ile Thr Gly Val Gln
65                  70                  75                  80

Pro Glu Asp Glu Ala Asp Tyr Tyr Cys Ser Ala Trp Asp Thr Ser Leu
                85                  90                  95

Asn Ala Leu Val Phe Gly Gly Gly Thr Lys Leu Thr Val Leu
            100                 105                 110
```

<210> SEQ ID NO 31
<211> LENGTH: 114
<212> TYPE: PRT
<213> ORGANISM: Homo sapians

<400> SEQUENCE: 31

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

His Met His Trp Val Arg Gln Ala Pro Gly Gln Gly Leu Glu Trp Met
            35                  40                  45

Gly Trp Ile Asn Pro Asn Ser Gly Val Thr Lys Tyr Ala Gln Lys Phe
        50                  55                  60

Gln Gly Arg Val Thr Met Thr Arg Asp Thr Ser Ile Asn Thr Ala Tyr
65                  70                  75                  80

Met Glu Leu Ser Arg Leu Arg Phe Asp Asp Thr Asp Val Tyr Tyr Cys
                85                  90                  95

Ala Thr Gly Gly Phe Gly Tyr Trp Gly Glu Gly Thr Leu Val Thr Val
                100                 105                 110

Ser Ser

<210> SEQ ID NO 32
<211> LENGTH: 110
<212> TYPE: PRT
<213> ORGANISM: Homo sapians

<400> SEQUENCE: 32

Gln Ala Val Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
                20                  25                  30

Gly Ala Ala Trp Leu Gln Gln His Gln Gly Gln Pro Pro Lys Leu Leu
            35                  40                  45

Ser Tyr Arg Asn His Asn Arg Pro Ser Gly Val Ser Glu Arg Phe Ser
        50                  55                  60

Pro Ser Arg Ser Gly Asp Thr Ser Ser Leu Thr Ile Thr Gly Leu Gln
65                  70                  75                  80

Pro Glu Asp Glu Ala Asp Tyr Tyr Cys Leu Ala Trp Asp Ser Ser Leu
                85                  90                  95

Arg Ala Phe Val Phe Gly Thr Gly Thr Lys Leu Thr Val Leu
                100                 105                 110

<210> SEQ ID NO 33
<211> LENGTH: 121
<212> TYPE: PRT
<213> ORGANISM: Homo sapians

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Ser Ile Thr Thr Phe Ala Gln Asn Phe
        50                  55                  60

```
Gln Gly Arg Val Thr Met Thr Arg Asp Thr Ser Ser Thr Leu Tyr
65                  70                  75                  80

Met Glu Leu Ser Ser Leu Arg Ser Glu Asp Thr Ala Val Tyr Tyr Cys
            85                  90                  95

Ala Arg Glu Phe Arg Gln Asp Tyr Tyr Asn Gly Met Asp Val Trp Gly
        100                 105                 110

Gln Gly Thr Thr Val Thr Val Ser Ser
        115                 120
```

<210> SEQ ID NO 34
<211> LENGTH: 110
<212> TYPE: PRT
<213> ORGANISM: Homo sapians

<400> SEQUENCE: 34

```
Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
            85                  90                  95

Ile Pro Leu Val Phe Gly Gly Gly Thr Lys Leu Thr Val Leu
        100                 105                 110
```

<210> SEQ ID NO 35
<211> LENGTH: 114
<212> TYPE: PRT
<213> ORGANISM: Homo sapians

<400> SEQUENCE: 35

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Gly Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Asp Asp Thr Ala Val Tyr Tyr Cys
            85                  90                  95

Ala Arg Val Thr Ala Gly Tyr Trp Gly Gln Gly Thr Leu Val Thr Val
        100                 105                 110

Ser Ser
```

<210> SEQ ID NO 36
<211> LENGTH: 110
<212> TYPE: PRT
<213> ORGANISM: Homo sapians

```
<400> SEQUENCE: 36

Gln Ala Gly Leu Thr Gln Pro Pro Ser Val Ser Lys Asp Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Leu Ser
    50                  55                  60

Ala Ser Arg Ser Gly Asp Thr Ala Ser Leu Thr Ile Thr Gly Leu Gln
65                  70                  75                  80

Pro Glu Asp Glu Ala Asp Tyr Tyr Cys Ser Ala Trp Asp Thr Ser Leu
                85                  90                  95

Ser Ala Trp Val Phe Gly Gly Gly Thr Lys Leu Thr Val Leu
            100                 105                 110

<210> SEQ ID NO 37
<211> LENGTH: 123
<212> TYPE: PRT
<213> ORGANISM: Homo sapians

<400> SEQUENCE: 37

Val Gln Leu Val Glu Ser Gly Ala Glu Val Lys Lys Pro Gly Ala Ser
1               5                   10                  15

Val Lys Val Ser Cys Lys Ala Ser Gly Tyr Thr Phe Ser Ser His Tyr
            20                  25                  30

Met His Trp Val Arg Gln Ala Pro Gly Gln Gly Leu Glu Trp Met Gly
        35                  40                  45

Ile Ile Asn Pro Ser Gly Gly Ser Thr Ile Tyr Ala Gln Lys Phe Gln
    50                  55                  60

Gly Arg Val Thr Ile Asn Ala Asp Glu Ser Thr Ser Thr Ala Tyr Met
65                  70                  75                  80

Glu Leu Ser Ser Leu Gly Ser Asp Asp Thr Ala Val Tyr Tyr Cys Ala
                85                  90                  95

Arg Ala Ala Gly Gly Ala Val Ala Gly His Gly Ala Arg Phe Asp Tyr
            100                 105                 110

Trp Gly Gln Gly Thr Leu Val Thr Val Ser Ser
        115                 120

<210> SEQ ID NO 38
<211> LENGTH: 110
<212> TYPE: PRT
<213> ORGANISM: Homo sapians

<400> SEQUENCE: 38

Leu Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Arg Arg Ser
```

```
                        85                  90                  95

Ser Thr Leu Val Phe Gly Gly Gly Thr Lys Leu Thr Val Leu
            100                 105                 110

<210> SEQ ID NO 39
<211> LENGTH: 118
<212> TYPE: PRT
<213> ORGANISM: Homo sapians

<400> SEQUENCE: 39

Gln Ile Thr Leu Lys Glu Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Ala Tyr
65                  70                  75                  80

Met Glu Leu Ser Ser Leu Arg Ser Glu Asp Thr Ala Met Tyr Tyr Cys
                85                  90                  95

Ala Lys Asn His Pro Thr Ala Thr Leu Asp Tyr Trp Gly Gln Gly Thr
            100                 105                 110

Leu Val Thr Val Ser Ser
        115

<210> SEQ ID NO 40
<211> LENGTH: 110
<212> TYPE: PRT
<213> ORGANISM: Homo sapians

<400> SEQUENCE: 40

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Ser Asn Arg Phe
        50                  55                  60

Ser Gly Ser Lys Ser Ala Asn Thr Ala Ser Leu Thr Ile Phe Gly Leu
65                  70                  75                  80

Gln Ala Glu Asp Glu Gly Asp Tyr Tyr Cys Ser Ser Tyr Arg Ser Ile
                85                  90                  95

Arg Thr Val Leu Phe Gly Gly Gly Thr Lys Leu Thr Val Leu
            100                 105                 110

<210> SEQ ID NO 41
<211> LENGTH: 120
<212> TYPE: PRT
<213> ORGANISM: Homo sapians

<400> SEQUENCE: 41

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

```
Tyr Met His Trp Val Arg Gln Ala Pro Gly Arg Gly Leu Glu Trp Met
            35                  40                  45

Gly Ile Ile Asn Pro Ser Ser Gly Ser Thr Ser Tyr Ala Gln Lys Phe
 50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gln Gly Thr Ala Ile Arg Ala Phe Asp Ile Trp Gly Gln
                100                 105                 110

Gly Thr Met Val Thr Val Ser Ser
                115                 120

<210> SEQ ID NO 42
<211> LENGTH: 112
<212> TYPE: PRT
<213> ORGANISM: Homo sapians

<400> SEQUENCE: 42

Asp Ile Val Met Thr Gln Thr Pro Leu Ser Ser Pro Val Thr Leu Gly
1               5                   10                  15

Gln Pro Ala Ala Ile Ser Cys Arg Ser Ser Gln Ser Leu Val Asn Ser
                20                  25                  30

Asp Gly Asn Thr Tyr Leu Ser Trp Leu Gln Gln Arg Pro Gly Gln Pro
            35                  40                  45

Pro Arg Val Leu Ile Asn Lys Val Ser Asn Arg Leu Ser Gly Val Pro
 50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Glu Phe Pro Trp Thr Phe Gly Gln Gly Thr Arg Leu Glu Ile Lys
                100                 105                 110

<210> SEQ ID NO 43
<211> LENGTH: 120
<212> TYPE: PRT
<213> ORGANISM: Homo sapians

<400> SEQUENCE: 43

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Arg Gly Leu Glu Trp Met
            35                  40                  45

Gly Ile Ile Asn Pro Ser Ser Gly Ser Thr Ser Tyr Ala Gln Lys Phe
 50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gln Gly Thr Ala Ile Arg Ala Phe Asp Ile Trp Gly Gln
                100                 105                 110

Gly Thr Met Val Thr Val Ser Ser
                115                 120
```

```
<210> SEQ ID NO 44
<211> LENGTH: 112
<212> TYPE: PRT
<213> ORGANISM: Homo sapiens

<400> SEQUENCE: 44

Asp Val Val Met Thr Gln Ser Pro Leu Ser Ser Pro Val Thr Leu Gly
1               5                   10                  15

Gln Pro Ala Ser Ile Ser Cys Lys Ser Ser Gln Thr Leu Val His Asn
            20                  25                  30

Asp Gly Asn Ser Tyr Leu Ser Trp Leu His Gln Arg Pro Gly Gln Pro
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Gly Arg Val Glu Ala Glu Asp Val Gly Val Tyr Tyr Cys Met Gln Ala
                85                  90                  95

Thr Gln Phe Pro Tyr Thr Phe Gly Gln Gly Thr Lys Leu Glu Ile Lys
                100                 105                 110
```